US011384135B2

(12) United States Patent
Dai et al.

(10) Patent No.: US 11,384,135 B2
(45) Date of Patent: Jul. 12, 2022

(54) RECOMBINANT YEAST STRAINS

(71) Applicant: MODERN MEADOW, INC., Nutley, NJ (US)

(72) Inventors: Lixin Dai, Livingston, NJ (US); Poonam Srivastava, Union City, NJ (US)

(73) Assignee: MODERN MEADOW, INC., Nutley, NJ (US)

( * ) Notice: Subject to any disclaimer, the term of this patent is extended or adjusted under 35 U.S.C. 154(b) by 0 days.

(21) Appl. No.: 16/125,320

(22) Filed: Sep. 7, 2018

(65) Prior Publication Data

US 2019/0092838 A1 Mar. 28, 2019

Related U.S. Application Data

(60) Provisional application No. 62/562,109, filed on Sep. 22, 2017.

(51) Int. Cl.

| | | |
|---|---|---|
| *C12P 1/00* | (2006.01) |
| *C07K 14/78* | (2006.01) |
| *D01F 4/00* | (2006.01) |
| *C07K 14/195* | (2006.01) |
| *C07K 14/245* | (2006.01) |
| *C12N 1/16* | (2006.01) |
| *C12N 9/02* | (2006.01) |
| *C12N 15/81* | (2006.01) |
| *C12N 9/04* | (2006.01) |
| *C12N 9/12* | (2006.01) |
| *C12N 9/18* | (2006.01) |
| *C12N 9/90* | (2006.01) |
| *D01F 1/02* | (2006.01) |
| *C12R 1/84* | (2006.01) |

(52) U.S. Cl.
CPC ............ *C07K 14/78* (2013.01); *C07K 14/195* (2013.01); *C07K 14/245* (2013.01); *C12N 1/165* (2021.05); *C12N 9/001* (2013.01); *C12N 9/0006* (2013.01); *C12N 9/0071* (2013.01); *C12N 9/1205* (2013.01); *C12N 9/1241* (2013.01); *C12N 9/18* (2013.01); *C12N 9/90* (2013.01); *C12N 15/815* (2013.01); *D01F 4/00* (2013.01); *C12R 2001/84* (2021.05); *C12Y 101/0102* (2013.01); *C12Y 101/01019* (2013.01); *C12Y 101/01022* (2013.01); *C12Y 103/03012* (2013.01); *C12Y 114/11004* (2013.01); *C12Y 207/01001* (2013.01); *C12Y 207/01043* (2013.01); *C12Y 207/07009* (2013.01); *C12Y 207/07044* (2013.01); *C12Y 207/07069* (2013.01); *C12Y 301/01017* (2013.01); *C12Y 301/01019* (2013.01); *C12Y 301/03025* (2013.01); *C12Y 501/03018* (2013.01); *C12Y 504/02002* (2013.01); *D01F 1/02* (2013.01)

(58) Field of Classification Search
None
See application file for complete search history.

(56) References Cited

U.S. PATENT DOCUMENTS

| | | | |
|---|---|---|---|
| 6,413,742 B1 | 7/2002 | Olsen et al. | |
| 6,428,978 B1 | 8/2002 | Olsen et al. | |
| 8,188,230 B2 | 5/2012 | Van Heerde et al. | |
| 9,157,088 B2 * | 10/2015 | Laing | C12N 9/1241 |
| 10,167,511 B2 * | 1/2019 | Brandon | C12Q 1/6883 |
| 10,190,169 B2 * | 1/2019 | Brandon | C12Q 1/689 |
| 10,370,504 B2 * | 8/2019 | Purcell | D06M 15/15 |
| 2002/0098578 A1 | 7/2002 | Prockop et al. | |
| 2012/0116053 A1 | 5/2012 | Mironchnitchenko | |
| 2015/0011733 A1 | 1/2015 | Viswanathan et al. | |
| 2017/0233536 A1 | 8/2017 | Purcell et al. | |
| 2017/0233537 A1 | 8/2017 | Purcell et al. | |
| 2017/0233834 A1 | 8/2017 | Purcell et al. | |
| 2017/0233837 A1 | 8/2017 | Purcell et al. | |
| 2017/0233838 A1 | 8/2017 | Purcell et al. | |
| 2017/0233943 A1 | 8/2017 | Purcell et al. | |
| 2017/0233944 A1 * | 8/2017 | Purcell | B32B 27/12 442/187 |
| 2017/0233945 A1 | 8/2017 | Purcell et al. | |

FOREIGN PATENT DOCUMENTS

| | | |
|---|---|---|
| CN | 102071154 A | 5/2011 |
| EP | 0 967 226 A2 | 12/1999 |
| EP | 1232182 B1 | 10/2007 |
| WO | WO 2002/10425 A2 | 2/2002 |
| WO | WO 02/103001 A1 | 12/2002 |
| WO | WO 2006/113147 A2 | 10/2006 |
| WO | WO 2006/134374 A2 | 12/2006 |

(Continued)

OTHER PUBLICATIONS

International Search Report and Written Opinion dated Jan. 29, 2019 in PCT/US18/52148, 18 pages.
Wang, T. et al. "Production of recombinant collagen: state of the art and challenges" The Institution of Engineering and Technology, vol. 1, No. 1, 2017, pp. 18-23.
Office Action dated Jun. 25, 2019 in Canadian Patent Application No. 3,017,458.
Chan, P., et al., "Assaying proline hydroxylation in recombinant collagen variants by liquid chromatography-mass spectrometry," BMC Biotechnology 12(51):1-7, Springer Nature, United Kingdom (Aug. 2012).

(Continued)

*Primary Examiner* — Hope A Robinson
(74) *Attorney, Agent, or Firm* — Sterne, Kessler, Goldstein & Fox P.L.L.C.

(57) ABSTRACT

This invention relates to genetically engineered strains of yeast and methods, for producing recombinant protein (e.g., collagen). Recombinant protein of the present invention is used to produce biofabricated leather or a material having leather-like properties containing recombinant or engineered collagen. The yeast strains are engineered to produce ascorbate and/or increased production of α ketoglutarate.

8 Claims, No Drawings
Specification includes a Sequence Listing.

(56) References Cited

FOREIGN PATENT DOCUMENTS

| WO | WO 2011/123811 A2 | 10/2011 |
|---|---|---|
| WO | WO 2012/170782 A2 | 12/2012 |
| WO | WO 2013/020064 A1 | 2/2013 |
| WO | WO 2017/142887 A1 | 8/2017 |

OTHER PUBLICATIONS

Gene ID: 281409, "PLOD1 procollagen-lysine,2-oxoglutarate 5-dioxygenase 1 [ *Bos taurus* (cattle)]," retrieved from: https://www.ncbi.nlm.nih.gov/gene/281409, retrieved on Mar. 11, 2020, 4 pages.

Gene ID: 27806257, "G369_RS0122905 MFS transporter [ Variovorax paradoxus 110B]," retrieved from: https://www.ncbi.nlm.nih.gov/gene/27806257, retrieved on Mar. 11, 2020, 7 pages.

Hausmann, E., "Cofactor requirements for the enzymatic hydroxylation of lysine in a polypeptide precursor of collagen," Biochim. Biophys. Acta 133:591-593, Elsevier, Netherlands (Apr. 1967).

NCBI Ref Sequence: NP_001029211.1, "collagen alpha-1(I) chain precursor [Bos taurus]," retrieved from: https://www.ncbi.nlm.nih.gov/protein/NP_001029211.1, retrieved on Mar. 11, 2020, 13 pages.

NCBI Ref Sequence: NP_001070299.1, "collagen alpha-1(III) chain precursor [Bos taurus]," retrieved from: https://www.ncbi.nlm.nih.gov/protein/NP_001070299.1, retrieved on Mar. 11, 2020, 3 pages.

OMIM 176710 "Procollagen-Proline, 2-Oxoglutarate-4-Dioxygenase, Alpha Subunit, Isoform 1; P4HA1 ," retrieved from: https://omim.org/entry/176710, retrieved on Mar. 11, 2020, 3 pages.

OMIM 176790 "Procollagen-Proline, 2-Oxoglutarate-4-Dioxygenase, Beta Subunit; P4HB," retrieved from: https://omim.org/entry/176790, retrieved on Mar. 11, 2020, 4 pages.

OMIM 610339 "Prolyl 3-Hydroxylase 1; P3H1," retrieved from: https://omim.org/entry/610339, retrieved on Mar. 11, 2020, 4 pages.

Pinkas, D.M., et al., "Tunable, post-translation hydroxylation of collagen domains in *Escherichia coli*," ACS Chem Biol 6(4):320-324, American Chemical Society, United States (Jan. 2011).

Razaghi, A., et al., "Is Pichia pastoris a realistic platform for industrial production of recombinant human interferon gamma," Biologicals 45:52-60, Elsevier, Netherlands (Jan. 2017).

Seol, W., et al., "Membrane topology model of *Escherichia coli* alpha-ketoglutarate permease by phoA fusion analysis," J. Bacteriol 175(2):565-567, American Society for Microbiology, United States (Jan. 1993).

Smirnoff, N., "L-Ascorbic Acid Biosynthesis," Vitamins and Hormones 61:241-246, Academic Press, England (2001).

Vazquez-Bermudez, M.F., et al., "Uptake of 2-oxoglutarate in Synechococcus strains transformed with the *Escherichia coli* kgtP gene," J. Bacteriol 182(1):211-215, American Society for Microbiology, United States (Jan. 2000).

Vranka, J.A., et al., "Prolyl 3-Hydroxylase 1, Enzyme Characterization and Identification of a Novel Family of Enzymes," Journal of Biological Chemistry 279(22):23615-23621, American Society for Biochemistry and Molecular Biology, United States (May 2004).

Vuorela, A., et al., "Assembly of human prolyl 4-hydroxylase and type III collagen in the yeast *Pichia pastoris*: formation of a stable enzyme tetramer requires coexpression with collagen and assembly of a stable collagen requires coexpression with prolyl 4-hydroxylase," EMBO 16(22):6702-6712, Oxford University Press, United Kingdom (Nov. 1997).

Yamauchi, M., et al., "Lysine Hydroxylation and Cross-linking of Collagen," Post-translation Modifications of Proteins 446: 95-108 Methods in Molecular Biology, Springer Link (Jun. 2019).

Extended European Search Report dated Dec. 13, 2018 in Patent Application No. 18195972.7, 9 pages.

Castegna, A. et al. "Identification and Functional Characterization of a Novel Mitochondrial Carrier for Citrate and Oxoglutarate in *Saccharomyces cerevisiae*" Journal of Biological Chemistry, vol. 285, No. 23, XP055528717, 2010, pp. 17359-17370.

Myllylä, R. et al. "The role of ascorbate in the prolyl hydroxylase reaction" Biochemical and Biophysical Research Communications, vol. 83, No. 2, XP024841419, 1978, pp. 441-448.

Branduardi P., et al., "Biosynthesis of Vitamin C by Yeast Leads to Increased Stress Resistance," PLoS One, 2(10): e1092, pp. 1-8, Public Library of Science, United States (2007).

Bremus C., et al., "The use of microorganisms in l-ascorbic acid Production," Journal of Biotechnology, 124(1):196-205, Elsevier, Netherlands (2006).

Hancock R. D., et al., "Biotechnological approaches for l-ascorbic acid Production," Trends In Biotechnology, 20(7):299-305, Cell Press, United States (2002).

Hancock R. D., et al., "Biosynthesis of L-ascorbic acid (vitamin C) by *Saccharomyces cerevisiae*," FEMS Microbiology Letters, 186(2):245-250, Elsevier, Netherlands (2000).

Nokelainen M., et al., "High-level production of human type I collagen in the yeast *Pichia pastoris*," Yeast, 18(9):797-806, Wiley-Blackwell, United States (2001).

Rosa J. C. C., et al., "Metabolic engineering of *Kluyveromyces lactis* for L-ascorbic acid (vitamin C) biosynthesis," Microbial Cell Factories, 12(59):1-13, BioMed Central, United Kingdom (2013).

Sauer M., et al., "Production of L-Ascorbic Acid by Metabolically Engineered *Saccharomyces cerevisiae* and *Zygosaccharomyces bailii*," Applied and Environmental Microbiology, 70(10):6086-6091, American Society for Microbiology, United States (2004).

Seol, W., and Shatkin, A. J., "*Escherichia coli* kgtP encodes an alpha-ketoglutarate transporter," Proc Natl Acad Sci USA 88(9):3802-3806, National Academy of Science, United States (May 1991).

\* cited by examiner

RECOMBINANT YEAST STRAINS

CROSS REFERENCE TO RELATED APPLICATIONS

This application is related to U.S. patent application Ser. No. 15/433,566 entitled Biofabricated Material Containing Collagen Fibrils, Ser. No. 15/433,650 entitled Method for Making a Biofabricated Material Containing Collagen Fibrils, 62/526,912 entitled Recombinant Yeast Strains, and 62/539,213 entitled Yeast Strains and Method for Controlling Hydroxylation of Recombinant Collagen, and claims priority to 62/562,109, filed Sep. 22, 2017, entitled Recombinant Yeast Strains. The entire contents of these applications are incorporated by reference.

FIELD OF THE INVENTION

This invention herein provides genetically engineered strains of yeast and methods for producing recombinant proteins and carbohydrates. In an embodiment, the invention herein provides genetically engineered strains of yeast and methods for producing recombinant collagen that can be used to produce biofabricated leather materials, articles comprising biofabricated materials, and/or a material having leather-like properties containing recombinant or engineered collagen. The yeast strains are engineered to produce increased amounts of hydroxylated protein (e.g., collagen) and carbohydrates by improving the hydroxylation reaction through the use of an a ketoglutarate transporter (kgtP) and/or one or more polypeptides that enable an ascorbate synthesis pathway to function such as, GDP-L-Gal phosphorylase, inositol-phosphate phosphatase, GDP-Mannose-3,5-epimerase and/or L-gulono-1,4-lactone oxidase, aldonolactonase, glucurono lactone reductase, D-glucuronate reductase, uronolactonase, D-glucurono kinase, glucuronate-1-phosphate uridylyltransferase, UDP-D-glucose dehydrogenase, UTP-glucose-1-phosphate uridylyltransferase, phosphoglucomutase, and/or hexokinase.

DESCRIPTION OF RELATED ART

Leather is used in a vast variety of applications, including furniture upholstery, clothing, shoes, luggage, handbag and accessories, and automotive applications. The estimated global trade value in leather is approximately US $100 billion per year (*Future Trends in the World Leather Products Industry and Trade*, United Nations Industrial Development Organization, Vienna, 2010) and there is a continuing and increasing demand for leather products. Traditional leather production is wasteful with respect to animal hide and chemicals. The ever increasing demand for animal hides to keep up with the continuing and increasing demand for leather products puts additional pressure on our increasingly strained food sources, while the chemical waste continues to contribute to our eroding environmental conditions. Thus, new ways to meet this demand are required in view of the economic, environmental and social costs of producing leather. To keep up with technological and aesthetic trends, producers and users of leather products seek new materials exhibiting superior strength, uniformity, processability and fashionable and appealing aesthetic properties that incorporate natural components.

Given population growth and the global environment, there will be a need for alternative materials that have leather-like aesthetics and improved functionalities. Leather is animal hide and consists almost entirely of collagen. There is a need for new sources of collagen that can be incorporated into biofabricated materials.

Production of biofabricated materials using recombinantly-expressed collagen faces a number of challenges including a need for a method for efficiently producing collagen in forms and quantity needed for diverse commercial applications. For some applications a softer and more permeable collagen component is desired; in others, a harder, more resistant and durable collagen component is needed.

The inventors sought to address these challenges by engineering recombinant yeasts with a kgtP gene which provides an a ketoglutarate transporter and/or with one or more genes that enable an ascorbate synthesis pathway to function such that the recombinant yeast cell produces ascorbate.

SUMMARY OF THE INVENTION

One aspect of the invention is directed to modified yeast cells which contain an a ketoglutarate transporter. Modification includes transforming a kgtP gene into the yeast which enables the yeast to make the a ketoglutarate transporter. The yeast cells may be further modified to express and/or overexpress a protein which hydroxylates proline and/or lysine residues to yield hydroxyproline, 3-hydroxyproline (Hyp) and hydroxylysine (Hyl), and glycosylation of the hydroxylysyl residues. In an embodiment of the present invention, the present invention provides a method for improving production of proteins such as hydroxylated protein (e.g., collagen) or carbohydrates in yeast. The method includes inserting (e.g., transforming or genomically integrating) a kgtP gene, DNA for a protein or carbohydrate and DNA for promoters, terminators, and markers into the yeast to enable the yeast to produce an a ketoglutarate transporter and the protein or carbohydrate. The method also includes inserting genes expressing a protein(s) which hydroxylates proline and/or lysine residues.

Another aspect of the invention is directed to modified yeast cells which produce ascorbate. Modification includes inserting genes which enable an ascorbate synthesis pathway to function. In an embodiment, the present invention provides a method for producing modified yeast cells which produce ascorbate. The method includes inserting genes necessary to complete a functioning ascorbate synthesis pathway. In this method, it is envisioned that it is only necessary to insert one or more of the genes encoding proteins for the portion of the ascorbate synthesis pathway downstream from the ascorbate pathway precursor fed to the yeast cells. In another embodiment, the present invention provides a method of producing intracellular ascorbate in a yeast cell including growing a modified yeast cell in media. In another embodiment, the present invention provides a modified yeast cell with a constant amount of intracellular ascorbate.

Yet another aspect of the invention is directed to modified yeast cells which contain an a ketoglutarate transporter and which produce ascorbate. The yeast cells may be further modified to express and/or overexpress a protein which hydroxylates proline and/or lysine residues to yield hydroxyproline, 3-hydroxyproline (Hyp) and hydroxylysine (Hyl), and glycosylation of the hydroxylysyl residues. The method includes inserting genes necessary to complete a functioning ascorbate synthesis pathway and an a ketoglutarate transporter into the yeast. The method may also include inserting genes expressing a protein(s) which hydroxylates proline and/or lysine residues. In another embodiment, the present invention provides a method of producing intracellular ascorbate in a yeast cell including growing a modified yeast cell in media. In an embodiment of the present invention, the present invention provides a method for improving production of proteins such as hydroxylated collagen or carbohydrates in yeast that contain an a ketoglutarate transporter and which produce ascorbate.

DETAILED DESCRIPTION OF THE INVENTION

As described and exemplified herein, yeast cells (e.g., *Pichia pastoris*) can be used to express recombinant Type III bovine collagen with different degrees of hydroxylation. Hydroxylation of recombinant collagen is accomplished by co-expression of bovine P4HA and bovine P4HB which respectively encode the alpha and beta subunits bovine prolyl-4-hydroxylase. However, the invention is not limited to products and expression of Type III collagen and may be practiced with other proteins or carbohydrates, polynucleotides encoding the subunits of other kinds of collagens as well as with enzymes that hydroxylate proline residues, lysine residues, or both proline and lysine residues. Type III tropocollagen is a homotrimer. However, in some embodiments a collagen will form a heterotrimer composed of different polypeptide chains, such as Type I collagen which is initially composed of two pro-$\alpha$1(I) chains and one pro-$\alpha$2(I) chain.

Collagen. Collagen is the main component of leather. Skin, or animal hide, contains significant amounts of collagen, a fibrous protein. Collagen is a generic term for a family of at least 28 distinct collagen types; animal skin is typically Type I collagen, although other types of collagen can be used in forming leather including type III collagen. The term "collagen" encompasses unprocessed (e.g., procollagens) as well as post-translationally modified and proteolysed collagens having a triple helical structure.

Collagens are characterized by a repeating triplet of amino acids, -(Gly-X-Y)n- and approximately one-third of the amino acid residues in collagen are glycine. X is often proline and Y is often hydroxyproline, though there may be up to 400 possible Gly-X-Y triplets. Different animals may produce different amino acid compositions of the collagen, which may result in different properties and in differences in the resulting leather.

The structure of collagen can consist of three intertwined peptide chains of differing lengths. Collagen triple helices (or monomers) may be produced from alpha-chains of about 1,050 amino acids long, so that the triple helix takes the form of a rod of about approximately 300 nm long, with a diameter of approximately 1.5 nm.

Collagen fibers may have a range of diameters depending on the type of animal hide. In addition to type I collagen, skin (hides) may include other types of collagen as well, including type III collagen (reticulin), type IV collagen, and type VII collagen. Various types of collagen exist throughout the mammalian body. For example, besides being the main component of skin and animal hide, Type I collagen also exists in cartilage, tendon, vascular ligature, organs, muscle, and the organic portion of bone. Successful efforts have been made to isolate collagen from various regions of the mammalian body in addition to the animal skin or hide. Decades ago, researchers found that at neutral pH, acid-solubilized collagen self-assembled into fibrils composed of the same cross-striated patterns observed in native tissue; Schmitt F. O. J. Cell. Comp Physiol. 1942; 20:11). This led to use of collagen in tissue engineering and a variety of biomedical applications. In more recent years, collagen has been harvested from bacteria and yeast using recombinant techniques.

Collagens are formed and stabilized through a combination of physical and chemical interactions including electrostatic interactions such as salt bridging, hydrogen bonding, Van der Waals interactions, dipole-dipole forces, polarization forces, hydrophobic interactions, and covalent bonding often catalyzed by enzymatic reactions. Various distinct collagen types have been identified in vertebrates including bovine, ovine, porcine, chicken, and human collagens.

Generally, the collagen types are numbered by Roman numerals, and the chains found in each collagen type are identified by Arabic numerals. Detailed descriptions of structure and biological functions of the various different types of naturally occurring collagens are available in the art; see, e.g., Ayad et al. (1998) The Extracellular Matrix Facts Book, Academic Press, San Diego, Calif.; Burgeson, R E., and Nimmi (1992) "Collagen types: Molecular Structure and Tissue Distribution" in Clin. Orthop. 282:250-272; Kielty, C. M. et al. (1993) "The Collagen Family: Structure, Assembly And Organization In The Extracellular Matrix," Connective Tissue And Its Heritable Disorders, Molecular Genetics, And Medical Aspects, Royce, P. M. and B. Steinmann eds., Wiley-Liss, NY, pp. 103-147; and Prockop, D. J- and K. I. Kivirikko (1995) "Collagens: Molecular Biology, Diseases, and Potentials for Therapy," Annu. Rev. Biochem., 64:403-434.)

Type I collagen is the major fibrillar collagen of bone and skin comprising approximately 80-90% of an organism's total collagen. Type I collagen is the major structural macromolecule present in the extracellular matrix of multicellular organisms and comprises approximately 20% of total protein mass. Type I collagen is a heterotrimeric molecule comprising two $\alpha$1 (I) chains and one $\alpha$2(I) chain, encoded by the COL1A1 and COL1A2 genes, respectively. In vivo, assembly of Type I collagen fibrils, fibers, and fiber bundles takes place during development and provides mechanical support to the tissue while allowing for cellular motility and nutrient transport. Other collagen types are less abundant than type I collagen and exhibit different distribution patterns. For example, type II collagen is the predominant collagen in cartilage and vitreous humor, while type III collagen is found at high levels in blood vessels and to a lesser extent in skin.

Type II collagen is a homotrimeric collagen comprising three identical a1(II) chains encoded by the COL2A1 gene. Purified type II collagen may be prepared from tissues by, methods known in the art, for example, by procedures described in Miller and Rhodes (1982) Methods In Enzymology 82:33-64.

Type III collagen is a major fibrillar collagen found in skin and vascular tissues. Type III collagen is a homotrimeric collagen comprising three identical $\alpha$1(III) chains encoded by the COL3A1 gene. The COL3A1 gene may be optimized for expression in the host cell, for example *Pichia pastoris* (SEQ ID NO: 10). Methods for purifying type III collagen from tissues can be found in, for example, Byers et al. (1974) Biochemistry 13:5243-5248; and Miller and Rhodes, supra.

Type IV collagen is found in basement membranes in the form of sheets rather than fibrils. Most commonly, type IV collagen contains two $\alpha$1(IV) chains and one $\alpha$2(IV) chain. The particular chains comprising type IV collagen are tissue-specific. Type IV collagen may be purified using, for example, the procedures described in Furuto and Miller (1987) Methods in Enzymology, 144:41-61, Academic Press.

Type V collagen is a fibrillar collagen found in, primarily, bones, tendon, cornea, skin, and blood vessels. Type V collagen exists in both homotrimeric and heterotrimeric forms. One form of type V collagen is a heterotrimer of two α1(V) chains and one α2(V) chain. Another form of type V collagen is a heterotrimer of α1(V), α2(V), and α3(V) chains. A further form of type V collagen is a homotrimer of α1(V). Methods for isolating type V collagen from natural sources can be found, for example, in Elstow and Weiss (1983) Collagen Rel. Res. 3:181-193, and Abedin et al. (1982) Biosci. Rep. 2:493-502.

Type VI collagen has a small triple helical region and two large non-collagenous remainder portions. Type VI collagen is a heterotrimer comprising α1(VI), α2(VI), and α3(VI) chains. Type VI collagen is found in many connective tissues. Descriptions of how to purify type VI collagen from natural sources can be found, for example, in Wu et al. (1987) Biochem. J. 248:373-381, and Kielty et al. (1991) J. Cell Sci. 99:797-807.

Type VII collagen is a fibrillar collagen found in particular epithelial tissues. Type VII collagen is a homotrimeric molecule of three α1(VII) chains. Descriptions of how to purify type VII collagen from tissue can be found in, for example, Lunstrum et al. (1986) J. Biol. Chem. 261:9042-9048, and Bentz et al. (1983) Proc. Natl. Acad. Sci. USA 80:3168-3172. Type VIII collagen can be found in Descemet's membrane in the cornea. Type VIII collagen is a heterotrimer comprising two α1(VIII) chains and one α2(VIII) chain, although other chain compositions have been reported. Methods for the purification of type VIII collagen from nature can be found, for example, in Benya and Padilla (1986) J. Biol. Chem. 261:4160-4169, and Kapoor et al. (1986) Biochemistry 25:3930-3937.

Type IX collagen is a fibril-associated collagen found in cartilage and vitreous humor. Type IX collagen is a heterotrimeric molecule comprising α1(IX), α2(IX), and α3(IX) chains. Type IX collagen has been classified as a FACIT (Fibril Associated Collagens with Interrupted Triple Helices) collagen, possessing several triple helical domains separated by non-triple helical domains. Procedures for purifying type IX collagen can be found, for example, in Duance, et al. (1984) Biochem. J. 221:885-889; Ayad et al. (1989) Biochem. J. 262:753-761; and Grant et al. (1988) The Control of Tissue Damage, Glauert, A. M., ed., Elsevier Science Publishers, Amsterdam, pp. 3-28.

Type X collagen is a homotrimeric compound of α1(X) chains. Type X collagen has been isolated from, for example, hypertrophic cartilage found in growth plates; see, e.g., Apte et al. (1992) Eur J Biochem 206 (1):217-24.

Type XI collagen can be found in cartilaginous tissues associated with type II and type IX collagens, and in other locations in the body. Type XI collagen is a heterotrimeric molecule comprising α1(XI), α2(XI), and α3(XI) chains. Methods for purifying type XI collagen can be found, for example, in Grant et al., supra.

Type XII collagen is a FACIT collagen found primarily in association with type I collagen. Type XII collagen is a homotrimeric molecule comprising three α1(XII) chains. Methods for purifying type XII collagen and variants thereof can be found, for example, in Dublet et al. (1989) J. Biol. Chem. 264:13150-13156; Lunstrum et al. (1992) J. Biol. Chem. 267:20087-20092; and Watt et al. (1992) J. Biol. Chem. 267:20093-20099. Type XIII is a non-fibrillar collagen found, for example, in skin, intestine, bone, cartilage, and striated muscle. A detailed description of type XIII collagen may be found, for example, in Juvonen et al. (1992) J. Biol. Chem. 267: 24700-24707.

Type XIV is a FACIT collagen characterized as a homotrimeric molecule comprising α1(XIV) chains. Methods for isolating type XIV collagen can be found, for example, in Aubert-Foucher et al. (1992) J. Biol. Chem. 267:15759-15764, and Watt et al., supra.

Type XV collagen is homologous in structure to type XVIII collagen. Information about the structure and isolation of natural type XV collagen can be found, for example, in Myers et al. (1992) Proc. Natl. Acad. Sci. USA 89:10144-10148; Huebner et al. (1992) Genomics 14:220-224; Kivirikko et al. (1994) J. Biol. Chem. 269:4773-4779; and Muragaki, J. (1994) Biol. Chem. 264:4042-4046.

Type XVI collagen is a fibril-associated collagen, found, for example, in skin, lung fibroblast, and keratinocytes. Information on the structure of type XVI collagen and the gene encoding type XVI collagen can be found, for example, in Pan et al. (1992) Proc. Natl. Acad. Sci. USA 89:6565-6569; and Yamaguchi et al. (1992) J. Biochem. 112:856-863.

Type XVII collagen is a hemidesmosal transmembrane collagen, also known at the bullous pemphigoid antigen. Information on the structure of type XVII collagen and the gene encoding type XVII collagen can be found, for example, in Li et al. (1993) J. Biol. Chem. 268(12):8825-8834; and McGrath et al. (1995) Nat. Genet. 11(1):83-86.

Type XVIII collagen is similar in structure to type XV collagen and can be isolated from the liver. Descriptions of the structures and isolation of type XVIII collagen from natural sources can be found, for example, in Rehn and Pihlajaniemi (1994) Proc. Natl. Acad. Sci USA 91:4234-4238; Oh et al. (1994) Proc. Natl. Acad. Sci USA 91:4229-4233; Rehn et al. (1994) J. Biol. Chem. 269:13924-13935; and Oh et al. (1994) Genomics 19:494-499.

Type XIX collagen is believed to be another member of the FACIT collagen family, and has been found in mRNA isolated from rhabdomyosarcoma cells. Descriptions of the structures and isolation of type XIX collagen can be found, for example, in Inoguchi et al. (1995) J. Biochem. 117:137-146; Yoshioka et al. (1992) Genomics 13:884-886; and Myers et al., J. Biol. Chem. 289:18549-18557 (1994).

Type XX collagen is a newly found member of the FACIT collagenous family, and has been identified in chick cornea. (See, e.g., Gordon et al. (1999) FASEB Journal 13:A1119; and Gordon et al. (1998), IOVS 39:S1128.)

The term "collagen" refers to any one of the known collagen types, including collagen types I through XX described above, as well as to any other collagens, whether natural, synthetic, semi-synthetic, or recombinant. It includes all of the collagens, modified collagens and collagen-like proteins described herein. The term also encompasses procollagens and collagen-like proteins or collagenous proteins comprising the motif (Gly-X-Y)n where n is an integer. It encompasses molecules of collagen and collagen-like proteins, trimers of collagen molecules, fibrils of collagen, and fibers of collagen fibrils. It also refers to chemically, enzymatically or recombinantly-modified collagens or collagen-like molecules that can be fibrillated as well as fragments of collagen, collagen-like molecules and collagenous molecules capable of assembling into a nanofiber. Recombinant collagen molecules whether native or engineered will generally comprise the repeated -(Gly-X-Y)n- sequence described herein.

The collagen in a collagen composition may homogenously contain a single type of collagen molecule, such as 100% bovine Type I collagen or 100% Type III bovine collagen, or may contain a mixture of different kinds of collagen molecules or collagen-like molecules, such as a mixture of bovine Type I and Type III molecules. Such mixtures may include >0%, 10, 20, 30, 40, 50, 60, 70, 80, 90, 95, 99 or <100% of the individual collagen or collagen-like protein components. This range includes all intermediate values. For example, a collagen composition may contain 30% Type I collagen and 70% Type III collagen, or may contain 33.3% of Type I collagen, 33.3% of Type II collagen, and 33.3% of Type III collagen, where the percentage of collagen is based on the total mass of collagen in the composition or on the molecular percentages of collagen molecules.

"Collagen fibrils" are nanofibers composed of tropocollagen (triple helices of collagen molecules). Tropocollagens also include tropocollagen-like structures exhibiting triple helical structures. The collagen fibrils of the invention may have diameters ranging from 1 nm and 1 µm. For example, the collagen fibrils of the invention may have an average or individual fibril diameter ranging from 1, 2, 3, 4, 5, 10, 15, 20, 30, 40, 50, 60, 70, 80, 90, 100, 200, 300, 400, 500, 600, 700, 800, 900, or 1,000 nm (1 µm). This range includes all intermediate values and subranges. In some of the embodiments of the invention collagen fibrils will form networks. Collagen fibrils can associate into fibrils exhibiting a banded patter and these fibrils can associate into larger aggregates of fibrils. In some embodiments the collagen or collagen-like fibrils will have diameters and orientations similar to those in the top grain or surface layer of a bovine or other conventional leather. In other embodiments, the collagen fibrils may have diameters comprising the top grain and those of a corium layer of a conventional leather.

A "collagen fiber" is composed of collagen fibrils that are tightly packed and exhibit a high degree of alignment in the direction of the fiber. It can vary in diameter from more than 1 µm to more than 10 µm, for example >1, 2, 3, 4, 5, 6, 7, 8, 9, 10, 11, 12 µm or more. Some embodiments of the network of collage fibrils of the invention do not contain substantial content of collagen fibers having diameters greater than 5 µm. The composition of the grain surface of a leather can differ from its more internal portions, such as the corium which contains coarser fiber bundles.

"Fibrillation" refers to a process of producing collagen fibrils. It may be performed by raising the pH or by adjusting the salt concentration of a collagen solution or suspension. In forming the fibrillated collagen, the collagen may be incubated to form the fibrils for any appropriate length of time, including between 1 min and 24 hrs and all intermediate values.

The fibrillated collagen described herein may generally be formed in any appropriate shape and/or thickness, including flat sheets, curved shapes/sheets, cylinders, threads, and complex shapes. These sheets and other forms may have virtually any linear dimensions including a thickness, width or height greater of 10, 20, 30, 40, 50, 60, 70, 80, 90 mm; 1, 2, 3, 4, 5, 6, 7, 8, 9, 10, 50, 100, 200, 500, 1,000, 1,500, 2,000 cm or more.

The fibrillated collagen may lack any or any substantial amount of higher order structure. In a preferred embodiment, the collagen fibrils will be unbundled and not form the large collagen fibers found in animal skin and provide a strong and uniform non-anisotropic structure to the biofabricated leather.

In other embodiments, some collagen fibrils can be bundled or aligned into higher order structures. Collagen fibrils in a biofabricated leather may exhibit an orientation index ranging from 0, >0, 0.1, 0.2, 0.3, 0.4, 0.5, 0.6, 0.7, 0.8, 0.9, <1.0, or 1.0, wherein an orientation index of 0 describes collagen fibrils that lack alignment with other fibrils and an orientation index of 1.0 describes collagen fibrils that are completely aligned. This range includes all intermediate values and subranges. Those of skill in the art are familiar with the orientation index which is also incorporated by reference to Sizeland, et al., J. Agric. Food Chem. 61: 887-892 (2013) or Basil-Jones, et al., J. Agric. Food Chem. 59: 9972-9979 (2011).

A biofabricated leather may be fibrillated and processed to contain collagen fibrils that resemble or mimic the properties of collagen fibrils produced by particular species or breeds of animals or by animals raised under particular conditions.

Alternatively, fibrillation and processing conditions can be selected to provide collagen fibrils distinct from those found in nature, such as by decreasing or increasing the fibril diameter, degree of alignment, or degree of crosslinking compared to fibrils in natural leather.

A crosslinked network of collagen, sometimes called a hydrogel, may be formed as the collagen is fibrillated, or it may form a network after fibrillation; in some variations, the process of fibrillating the collagen also forms gel-like network. Once formed, the fibrillated collagen network may be further stabilized by incorporating molecules with di-, tri-, or multifunctional reactive groups that include chromium, amines, carboxylic acids, sulfates, sulfites, sulfonates, aldehydes, hydrazides, sulfhydryls, diazarines, aryl-, azides, acrylates, epoxides, or phenols.

The fibrillated collagen network may also be polymerized with other agents (e.g. polymers that are capable of polymerizing or other suitable fibers), which could be used to further stabilize the matrix and provide the desired end structure. Hydrogels based upon acrylamides, acrylic acids, and their salts may be prepared using inverse suspension polymerization. Hydrogels described herein may be prepared from polar monomers. The hydrogels used may be natural polymer hydrogels, synthetic polymer hydrogels, or a combination of the two. The hydrogels used may be obtained using graft polymerization, crosslinking polymerization, networks formed of water soluble polymers, radiation crosslinking, and so on. A small amount of crosslinking agent may be added to the hydrogel composition to enhance polymerization.

Average or individual collagen fibril length may range from 100, 200, 300, 400, 500, 600, 700, 800, 900, 1,000 (1 µm); 5, 10, 20, 30, 40, 50, 60, 70, 80, 90, 100, 200, 300, 400, 500, 600, 700, 800, 900, 1,000 µm (1 mm) throughout the entire thickness of a biofabricated leather. These ranges include all intermediate values and subranges.

Fibrils may align with other fibrils over 50, 100, 200, 300, 400, 500 µm or more of their lengths or may exhibit little or no alignment. In other embodiments, some collagen fibrils can be bundled or aligned into higher order structures.

Collagen fibrils in a biofabricated leather may exhibit an orientation index ranging from 0, >0, 0.1, 0.2, 0.3, 0.4, 0.5, 0.6, 0.7, 0.8, 0.9, <1.0, or 1.0, wherein an orientation index of 0 describes collagen fibrils that lack alignment with other fibrils and an orientation index of 1.0 describes collagen fibrils that are completely aligned. This range includes all intermediate values and subranges. Those of skill in the art are familiar with the orientation index which is also incorporated by reference to Sizeland, et al., J. Agric. Food Chem. 61: 887-892 (2013) or Basil-Jones, et al., J. Agric. Food Chem. 59: 9972-9979 (2011).

Collagen fibril density of a biofabricated leather may range from about 1 to 1,000 mg/cc, preferably from 5 to 500 mg/cc including all intermediate values, such as 5, 10, 20, 30, 40, 50, 60, 70, 80, 90, 100, 150, 200, 250, 300, 350, 400, 450, 500, 600, 700, 800, 900 and 1,000 mg/cc.

The collagen fibrils in a biofabricated leather may exhibit a unimodal, bimodal, trimodal, or multimodal distribution, for example, a biofabricated leather may be composed of two different fibril preparations each having a different range of fibril diameters arranged around one of two different modes. Such mixtures may be selected to impart additive, synergistic or a balance of physical properties on a biofabricated leather conferred by fibrils having different diameters.

Natural leather products may contain 150-300 mg/cc collagen based on the weight of the leather product. A biofabricated leather may contain a similar content of collagen or collagen fibrils as conventional leather based on the weight of the biofabricated leather, such as a collagen concentration of 100, 150, 200, 250, 300 or 350 mg/cc.

The fibrillated collagen, sometimes called a hydrogel, may have a thickness selected based on its ultimate use. Thicker or more concentrated preparations of the fibrillated collagen generally produce thicker biofabricated leathers. The final thickness of a biofabricated leather may be only 10, 20, 30, 40, 50, 60, 70, 80 or 90% that of the fibril preparation prior to shrinkage caused by crosslinking, dehydration and lubrication.

"Crosslinking" refers to formation (or reformation) of chemical bonds within between collagen molecules. A crosslinking reaction stabilizes the collagen structure and in some cases forms a network between collagen molecules. Any suitable crosslinking agent known in the art can be used including, without limitation, mineral salts such as those based on chromium, formaldehyde, hexamethylene diisocyanate, glutaraldehyde, polyepoxy compounds, gamma irradiation, and ultraviolet irradiation with riboflavin. The crosslinking can be performed by any known method; see, e.g., Bailey et al., Radiat. Res. 22:606-621 (1964); Housley et al., Biochem. Biophys. Res. Commun. 67:824-830 (1975); Siegel, Proc. Natl. Acad. Sci. U.S.A. 71:4826-4830 (1974); Mechanic et al., Biochem. Biophys. Res. Commun. 45:644-653 (1971); Mechanic et al., Biochem. Biophys. Res. Commun. 41:1597-1604 (1970); and Shoshan et al., Biochim. Biophys. Acta 154:261-263 (1968) each of which is incorporated by reference.

Crosslinkers include isocyantes, carbodiimide, poly(aldehyde), poly(azyridine), mineral salts, poly(epoxies), enzymes, thiirane, phenolics, novolac, resole as well as other compounds that have chemistries that react with amino acid side chains such as lysine, arginine, aspartic acid, glutamic acid, hydroxylproline, or hydroxylysine.

A collagen or collagen-like protein may be chemically modified to promote chemical and/or physical crosslinking between the collagen fibrils. Chemical crosslinking may be possible because reactive groups such as lysine, glutamic acid, and hydroxyl groups on the collagen molecule project from collagen's rod-like fibril structure. Crosslinking that involve these groups prevent the collagen molecules from sliding past each other under stress and thus increases the mechanical strength of the collagen fibers. Examples of chemical crosslinking reactions include but are not limited to reactions with the ε-amino group of lysine, or reaction with carboxyl groups of the collagen molecule. Enzymes such as transglutaminase may also be used to generate crosslinks between glutamic acid and lysine to form a stable γ-glutamyl-lysine crosslink. Inducing crosslinking between functional groups of neighboring collagen molecules is known in the art. Crosslinking is another step that can be implemented here to adjust the physical properties obtained from the fibrillated collagen hydrogel-derived materials.

Still fibrillating or fibrillated collagen may be crosslinked or lubricated. Collagen fibrils can be treated with compounds containing chromium or at least one aldehyde group, or vegetable tannins prior to network formation, during network formation, or network gel formation. Crosslinking further stabilizes the fibrillated collagen leather. For example, collagen fibrils pre-treated with acrylic polymer followed by treatment with a vegetable tannin, such as Acacia *Mollissima*, can exhibit increased hydrothermal stability. In other embodiments, glyceraldehyde may be used as a cross-linking agent to increase the thermal stability, proteolytic resistance, and mechanical characteristics, such as Young's modulus and tensile stress, of the fibrillated collagen.

A biofabricated material containing a network of collagen fibrils may contain 0, >0, 1, 2, 3, 4, 5, 6, 7, 8, 9, 10, 15, 20% or more of a crosslinking agent including tanning agents used for conventional leather. The crosslinking agents may be covalently bound to the collagen fibrils or other components of a biofabricated material or non-covalently associated with them. Preferably, a biofabricated leather will contain no more than 1, 2, 3, 4, 5, 6, 7, 8, 9 or 10% of a crosslinking agent.

"Lubricating" describes a process of applying a lubricant, such as a fat or other hydrophobic compound or any material that modulates or controls fibril-fibril bonding during dehydration to leather or to biofabricated products comprising collagen. A desirable feature of the leather aesthetic is the stiffness or hand of the material. In order to achieve this property, water-mediated hydrogen bonding between fibrils and/or fibers is limited in leather through the use of lubricants. Examples of lubricants include fats, biological, mineral or synthetic oils, cod oil, sulfonated oil, polymers, organofunctional siloxanes, and other hydrophobic compounds or agents used for fatliquoring conventional leather as well as mixtures thereof. While lubricating is in some ways analogous to fatliquoring a natural leather, a biofabricated product can be more uniformly treated with a lubricant due to its method of manufacture, more homogenous composition and less complex composition.

Other lubricants include surfactants, anionic surfactants, cationic surfactants, cationic polymeric surfactants, anionic polymeric surfactants, amphiphilic polymers, fatty acids, modified fatty acids, nonionic hydrophilic polymers, nonionic hydrophobic polymers, poly acrylic acids, poly methacrylic, acrylics, natural rubbers, synthetic rubbers, resins, amphiphilic anionic polymer and copolymers, amphiphilic cationic polymer and copolymers and mixtures thereof as well as emulsions or suspensions of these in water, alcohol, ketones, and other solvents. Lubricants may be added to a biofabricated material containing collagen fibrils.

Lubricants may be incorporated in any amount that facilitates fibril movement or that confers leather-like properties such as flexibility, decrease in brittleness, durability, or water resistance. A lubricant content can range from about 0.1, 0.25, 0.5, 1, 2, 3, 4, 5, 6, 7, 8, 9, 10, 15, 20, 25, 30, 35, 40, 45, 50, 55, and 60% by weight of the biofabricated leather.

Other additives may be added to modify the properties of biofabricated leather or material. Suitable additives include but are not limited to dyes, pigments, fragrances, resins, and microparticles. Resins may be added to modify the stretchability, strength, and softness of the material. Suitable resins include but are not limited to elastomers, acrylic copolymers, polyurethane, and the like. Suitable elastomers include but are not limited to styrene, isoprene, butadiene copolymers such as KRAYTON® elastomers, Hycar® acrylic resins. Resins may be used at from about 5% to 200%, or from about 50% to 150% (based on the weight of collagen), these ranges including all values and subranges there between such as 10, 15, 20, 25, 30, 35, 40, 60, 70, 75, 80, 90, 100, 125, 140 etc.

"Dehydrating" or "dewatering" describes a process of removing water from a mixture containing collagen fibrils and water, such as an aqueous solution, suspension, gel, or hydrogel containing fibrillated collagen. Water may be removed by filtration, evaporation, freeze-drying, solvent exchange, vacuum-drying, convection-drying, heating, irradiating or microwaving, or by other known methods for removing water. In addition, chemical crosslinking of collagen is known to remove bound water from collagen by consuming hydrophilic amino acid residues such as lysine, arginine, and hydroxylysine among others. The inventors have found that acetone quickly dehydrates collagen fibrils and may also remove water bound to hydrated collagen molecules. Water content of a biofabricated material or leather after dehydration is preferably no more than 60% by weight, for example, no more than 5, 10, 15, 20, 30, 35, 40, 50 or 60% by weight of the biofabricated leather. This range includes all intermediate values. Water content is measured by equilibration at 65% relative humidity at 25° C. and 1 atm.

"Grain texture" describes a leather-like texture which is aesthetically or texturally the similar to the texture of a full grain leather, top grain leather, corrected grain leather (where an artificial grain has been applied), or coarser split grain leather texture. Advantageously, the biofabricated material of the invention can be tuned to provide a fine grain, resembling the surface grain of a leather.

The articles in the invention ma include foot wear, garments, gloves, furniture or vehicle upholstery and other leather goods and products. It includes but is not limited to clothing, such as overcoats, coats, jackets, shirts, trousers, pants, shorts, swimwear, undergarments, uniforms, emblems or letters, costumes, ties, skirts, dresses, blouses, leggings, gloves, mittens, shoes, shoe components such as sole, quarter, tongue, cuff, welt, and counter, dress shoes, athletic shoes, running shoes, casual shoes, athletic, running or casual shoe components such as toe cap, toe box, outsole, midsole, upper, laces, eyelets, collar, lining, Achilles notch, heel, and counter, fashion or women's shoes and their shoe components such as upper, outer sole, toe spring, toe box, decoration, vamp, lining, sock, insole, platform, counter, and heel or high heel, boots, sandals, buttons, sandals, hats, masks, headgear, headbands, head wraps, and belts; jewelry such as bracelets, watch bands, and necklaces; gloves, umbrellas, walking sticks, wallets, mobile phone or wearable computer coverings, purses, backpacks, suitcases, handbags, folios, folders, boxes, and other personal objects; athletic, sports, hunting or recreational gear such as harnesses, bridles, reins, bits, leashes, mitts, tennis rackets, golf clubs, polo, hockey, or lacrosse gear, chessboards and game boards, medicine balls, kick balls, baseballs, and other kinds of balls, and toys; book bindings, book covers, picture frames or artwork; furniture and home, office or other interior or exterior furnishings including chairs, sofas, doors, seats, ottomans, room dividers, coasters, mouse pads, desk blotters, or other pads, tables, beds, floor, wall or ceiling coverings, flooring; automobile, boat, aircraft and other vehicular products including seats, headrests, upholstery, paneling, steering wheel, joystick or control coverings and other wraps or coverings.

Physical Properties of a biofabricated network of collagen fibrils or a biofabricated leather may be selected or tuned by selecting the type of collagen, the amount of concentration of collagen fibrillated, the degree of fibrillation, crosslinking, dehydration and lubrication.

Many advantageous properties are associated with the network structure of the collagen fibrils which can provide strong, flexible and substantially uniform properties to the resulting biofabricated material or leather. Preferable physical properties of the biofabricated leather according to the invention include a tensile strength ranging from 1, 2, 3, 4, 5, 6, 7, 8, 9, 10, 11, 12, 13, 14, 15 or more MPa, a flexibility determined by elongation at break ranging from 1, 5, 10, 15, 20, 25, 30% or more, softness as determined by ISO 17235 of 4, 5, 6, 7, 8 mm or more, a thickness ranging from 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 mm or more, and a collagen density (collagen fibril density) of 10, 20, 30, 40, 50, 60, 70, 80, 90, 100, 200, 300, 400, 500, 600, 700, 800, 900, 1,000 mg/cc or more, preferably 100-500 mg/cc. The above ranges include all subranges and intermediate values.

Thickness. Depending on its ultimate application a biofabricated material or leather may have any thickness. Its thickness preferably ranges from about 0.05 mm to 20 mm as well as any intermediate value within this range, such as 0.05, 0.1, 0.2, 0.5, 1, 2, 3, 4, 5, 6, 7, 8, 9, 10, 11, 12, 13, 14, 15, 16, 17, 18, 19, 20, 25, 30, 40, 50 mm or more. The thickness of a biofabricated leather can be controlled by adjusting collagen content.

Elastic modulus. The elastic modulus (also known as Young's modulus) is a number that measures an object or substance's resistance to being deformed elastically (i.e., non-permanently) when a force is applied to it. The elastic modulus of an object is defined as the slope of its stress-strain curve in the elastic deformation region. A stiffer material will have a higher elastic modulus. The elastic modulus can be measured using a texture analyzer.

A biofabricated leather can have an elastic modulus of at least 100 kPa. It can range from 100 kPa to 1,000 MPa as well as any intermediate value in this range, such as 0.1, 0.2, 0.3, 0.4, 0.5, 0.6, 0.7, 0.8, 0.9, 1, 2, 3, 4, 5, 6, 7, 8, 9, 10, 50, 100, 200, 300, 400, 500, 600, 700, 800, 900, or 1,000 MPa. A biofabricated leather may be able to elongate up to 300% from its relaxed state length, for example, by >0, 1, 2, 3, 4, 5, 6, 7, 8, 9, 10, 20, 30, 40, 50, 60, 70, 80, 90, 100, 150, 200, 250, or 300% of its relaxed state length.

Tensile strength (also known as ultimate tensile strength) is the capacity of a material or structure to withstand loads tending to elongate, as opposed to compressive strength, which withstands loads tending to reduce size. Tensile strength resists tension or being pulled apart, whereas compressive strength resists compression or being pushed together.

A sample of a biofabricated material may be tested for tensile strength using an Instron machine. Clamps are attached to the ends of the sample and the sample is pulled in opposite directions until failure. Good strength is demonstrated when the sample has a tensile strength of at least 1 MPa. A biofabricated leather can have a tensile strength of at least 1 kPa. It can range from 1 kPa to 100 MPa as well as any intermediate value in this range, such as 1, 2, 3, 4, 5, 6, 7, 8, 9, 10, 50, 100, 200, 300, 400, 500 kPA; 0.5, 0.6, 0.7, 0.8, 0.9, 1.0, 1.1, 1.2, 1.3, 1.4, 1.5, 2, 3, 4, 5, 6, 7, 8, 9, 10, 20, 30, 40, 50, 60, 70, 80, 90, or 100 MPa.

Tear strength (also known as tear resistance) is a measure of how well a material can withstand the effects of tearing. More specifically however it is how well a material (normally rubber) resists the growth of any cuts when under tension, it is usually measured in kN/m. Tear resistance can be measured by the ASTM D 412 method (the same used to measure tensile strength, modulus and elongation). ASTM D 624 can be used to measure the resistance to the formation of a tear (tear initiation) and the resistance to the expansion of a tear (tear propagation). Regardless of which of these two is being measured, the sample is held between two holders and a uniform pulling force applied until the aforementioned deformation occurs. Tear resistance is then calculated by dividing the force applied by the thickness of the material. A biofabricated leather may exhibit tear resistance of at least 1, 2, 3, 4, 5, 6, 7, 8, 9, 10, 15, 20, 25, 30, 35, 40, 45, 50, 100, 150 or 200% more than that of a conventional top grain or other leather of the same thickness comprising the same type of collagen, e.g., bovine Type I or Type III collagen, processed using the same crosslinker(s) or lubricants. A biofabricated material may have a tear strength ranging from about 1 to 500 N, for example, 1, 2, 3, 4, 5, 6, 7, 8, 9, 10, 20, 30, 40, 50, 60, 70, 80, 90, 100, 125, 150, 175, 200, 225, 250, 275, 300, 325, 350, 375, 400, 425, 450, 475, or 500 as well as any intermediate tear strength within this range.

Softness. ISO 17235:2015 specifies a non-destructive method for determining the softness of leather. It is applicable to all non-rigid leathers, e.g. shoe upper leather, upholstery leather, leather goods leather, and apparel leather. A biofabricated leather may have a softness as determined by ISO 17235 of 2, 3, 4, 5, 6, 7, 8, 10, 11, 12 mm or more.

Grain. The top grain surface of leather is often regarded as the most desirable due to its soft texture and smooth surface. The top grain is a highly porous network of collagen fibrils. The strength and tear resistance of the grain is often a limitation for practical applications of the top grain alone and conventional leather products are often backed with corium having a much coarser grain. A biofabricated material as disclosed herein which can be produced with strong and uniform physical properties or increased thickness can be used to provide top grain like products without the requirement for corium backing.

Content of other components. In some embodiments, the collagen is free of other leather components such as elastin or non-structural animal proteins. However, in some embodiments the content of actin, keratin, elastin, fibrin, albumin, globulin, mucin, mucinoids, noncollagen structural proteins, and/or noncollagen nonstructural proteins in a biofabricated leather may range from 0, 1, 2, 3, 4, 5, 6, 7, 8, 9 to 10% by weight of the biofabricated leather. In other embodiments, a content of actin, keratin, elastin, fibrin, albumin, globulin, mucin, mucinoids, noncollagen structural proteins, and/or noncollagen nonstructural proteins may be incorporated into a biofabricated leather in amounts ranging from >0, 1, 2, 3, 4, 5, 6, 7, 8, 9, 10, 11, 12, 13, 14, 15, 16, 17, 18, 19, 20% or more by weight of a biofabricated leather. Such components may be introduced during or after fibrillation, cross-linking, dehydration or lubrication. Content of collagen. The biofabricated material or leather in accordance with the present invention contains an increased collagen content as compared to conventional leather. Within the present invention, the collagen content in the biofabricated material or leather ranges from 15%, 20%, 25%, 30%, 35%, 40%, 45%, 50%, 55%, 60%, 70%, 75%, 80% or more to 95%, 90%, 85%, 80%, 75%, 70%, 65%, 60%, 55%, 50%, 45%, 40%, 35%, 30%, 25% or less, including all ranges and sub-ranges bound by the recited lower and upper limits.

A "leather dye" refers to dyes which can be used to color leather or biofabricated leather. These include acidic dyes, direct dyes, lakes, sulfur dyes, basic dyes and reactive dyes. Dyes and pigments can also be incorporated into a precursor of a biofabricated leather, such as into a suspension or network gel comprising collagen fibrils during production of the biofabricated leather.

"Fillers". In some embodiments a biofabricated leather may comprise fillers, other than components of leather, such as microspheres. One way to control the organization of the dehydrated fibril network is to include filling materials that keep the fibrils spaced apart during dehydration. These filler materials include nanoparticles, microparticles, or various polymers such as syntans commonly used in the tanning industry. These filling materials could be part of the final dehydrated leather material, or the filling materials could be sacrificial, that is they are degraded or dissolved away leaving open space for a more porous fibril network. The shape and dimension of these fillers may also be used to control the orientation of the dehydrated fibril network.

In some embodiments a filler may comprise polymeric microsphere(s), bead(s), fiber(s), wire(s), or organic salt(s). Other materials may also be embedded or otherwise incorporated into a biofabricated leather or into a network of collagen fibrils according to the invention. These include, but are not limited to one fibers, including both woven and nonwoven fibers as well as cotton, wool, cashmere, angora, linen, bamboo, bast, hemp, soya, seacell, fibers produced from milk or milk proteins, silk, spider silk, other peptides or polypeptides including recombinantly produced peptides or polypeptides, chitosan, mycelium, cellulose including bacterial cellulose, wood including wood fibers, rayon, lyocell, vicose, antimicrobial yarn (A.M.Y.), Sorbtek, nylon, polyester, elastomers such as LYCRA®, spandex or elastane and other polyester-polyurethane copolymers, aramids, carbon including carbon fibers and fullerenes, glass including glass fibers and nonwovens, silicon and silicon-containing compounds, minerals, including mineral particles and mineral fibers, and metals or metal alloys, including those comprising iron, steel, lead, gold, silver, platinum, copper, zinc and titanium, which may be in the form of particles, fibers, wires or other forms suitable for incorporating into biofabricated leather. Such fillers may include an electrically conductive material, magnetic material, fluorescent material, bioluminescent material, phosphorescent material or other photoluminescent material, or combinations thereof. Mixtures or blends of these components may also be embedded or incorporated into a biofabricated leather, for example, to modify the chemical and physical properties disclosed herein.

Various forms of collagen are found throughout the animal kingdom. The collagen used herein may be obtained from animal sources, including both vertebrates and invertebrates, or from synthetic sources. Collagen may also be sourced from byproducts of existing animal processing. Collagen obtained from animal sources may be isolated using standard laboratory techniques known in the art, for example, Silva et. Al., Marine Origin Collagens and its Potential Applications, Mar. Drugs, 2014 December, 12(12); 5881-5901).

The collagen described herein also may be obtained by cell culture techniques including from cells grown in a bioreactor.

Collagen may also be obtained via recombinant DNA techniques. Constructs encoding non-human collagen may be introduced into yeast to produce non-human collagen. For instance, collagen may also be produced with yeast, such as *Hansenula polymorpha, Saccharomyces cerevisiae, Pichia pastoris* and the like as the host. Recombinant expression of collagen and collagen-like proteins has been reported by Bell, EP 1232182B1, Bovine collagen and method for producing recombinant gelatin; Olsen, et al., U.S. Pat. No. 6,428,978, Methods for the production of gelatin and full-length triple helical collagen in recombinant cells; VanHeerde, et al., U.S. Pat. No. 8,188,230, Method for recombinant microorganism expression and isolation of collagen-like polypeptides, the disclosures of which are hereby incorporated by reference. However, recombinant collagens have not been used to produce leather.

Materials that are useful in the present invention include but are not limited to biofabricated leather materials natural or synthetic woven fabrics, non-woven fabrics, knitted fabrics, mesh fabrics, and spacer fabrics.

Any material that retains the collagen fibrils can be useful in the present invention. In general, fabrics that are useful have a mesh ranging from 300 threads per square inch to 1 thread per square foot or a pore size greater than or equal to about 11 μm in diameter. Spun lace materials may also be useful. In some embodiments, water soluble fabrics are useful. When utilized, the portion of the fabric exposed to the solution of collagen dissolves forming a void or hole in the fabric, and the collagen fills the void or hole. Water soluble fabrics are typically formed from polyvinyl alcohol fibers and coated with a resin such as polyvinyl alcohol, polyethylene oxide, hydroxyalkylcellulose, carboxymethylcellulose, polyacrylamide, polyvinyl pyrrolidone, polyacrylate and starch. Alternatively, the void or hole may be covered with a secondary material such as, natural or synthetic woven fabrics, non-woven fabrics, knitted fabrics, mesh fabrics, and spacer fabrics.

Alternatively, biofabricated leather material may be used to plug a void or hole cut into fabric. The size of the void or hole may vary depending on the design to be imparted. The shape of the void or hole may vary depending on the design. Suitable dimensions of void or holes may range from about 0.1 inches to about 5 meters. Suitable shapes include but are not limited to circles, squares, rectangles, triangles, elliptical, ovals and brand logos.

Some materials lend themselves to pretreatment to improve bonding of biofabricated leather materials. Pretreatment may include collagen coating, resin coating, devore of the fabric (also known as burn-out method), chemical or combinations thereof. For example, a chemical pretreatment for materials made from cellulose fibers, may include periodate (an oxidant) solution treatment. Suitable cellulose fabrics are selected from the group consisting of viscose, acetate, lyocell, bamboo and combinations thereof. The oxidant opens sugar rings in the cellulose and enables the collagen to bind to the open rings. The concentration of the oxidant in the solution depends on the extent of oxidation desired. In general, higher the concentration of oxidant or longer the reaction time, higher degree of oxidation is achieved. In an embodiment of the present invention, the oxidation reaction may be carried out for a desired amount of time to achieve the desired level of oxidation. The oxidation reaction can be carried out at various temperatures, depending on the type of oxidant used. The inventors have preferred using controlled oxidation at room (20° C. to 25° C., preferably 23° C.) or ambient temperature over a time range of 15 minutes-24 hours. However, it is also envisioned that temperatures ranging from 17.5° C. to 30° C. may also be used. With respect to time, it is envisioned that it is possible that controlled oxidation may be from 5 minutes, 10 minutes, 15, minutes, 20, minutes, 25 minutes, 30 minutes, 45 minutes, 60 minutes, 2 hours, 3, hours, 4, hours, 5 hours, 6 hours, 12 hours to 36 hours, 30 hours, 24, hours, 20 hours, 18 hours, 15 hours, including all ranges and sub-ranges permissible herein. The amount of sodium periodate ranges from 25% to 100% offers on weight of the fabric. As used herein, offer means the amount of an additive based on the weight % of cellulose. Other chemical pretreatments are taught in Bioconjugate Techniques by Greg Hermanson, which is hereby incorporated by reference.

The biofabricated leather (e.g., bioleather) solution as described herein may include any appropriate non-human collagen source in addition to and in combination with the recombinant collagen produced by the present yeast strains as discussed herein.

As an initial step in the formation of the collagen materials described herein, the starting collagen material may be placed in solution and fibrillated. The collagen concentration may range from approximately 0.5 g/L to 10 g/L, for example 0.75 g/L to 8 g/L, or 1 g/L to 7 g/L, or 2 g/L to 6 g/L, or 2.5 g/L to 5 g/L, or 3 g/L to 4 g/L. Collagen fibrillation may be induced through the introduction of salts to the collagen solution. The addition of a salt or a combination of salts such as sodium phosphate, potassium phosphate, potassium chloride, and sodium chloride to the collagen solution may change the ionic strength of the collagen solution. Collagen fibrillation may occur as a result of increasing electrostatic interactions, through greater hydrogen bonding, Van der Waals interactions, and covalent bonding. Suitable salt concentrations may range, for example, from approximately 10 mM to 5M, for example 50 mM to 2.5 M, or 100 mM to 1 M, or 250 mM to 500 mM.

A collagen network may also be highly sensitive to pH. During the fibrillation step, the pH may be adjusted to control fibril dimensions such as diameter and length. Suitable pH may range from approximately 5.5 to 10, for example 6 to 9, or 7 to 8. After the fibrillation step prior to filtration, the pH of the solution is adjusted to a pH range from approximately 3.5 to 10, for example 3.5 to 7, or 3.5 to 5. The overall dimensions and organization of the collagen fibrils will affect the toughness, stretch-ability, and breathability of the resulting fibrillated collagen derived materials. This may be of use for fabricating fibrillated collagen derived leather for various uses that may require different toughness, flexibility, and breathability.

One way to control the organization of the dehydrated fibril network is to include filling materials that keep the fibrils spaced apart during drying. These filler materials could include nanoparticles, microparticles, microspheres, microfibers, or various polymers commonly used in the tanning industry. These filling materials could be part of the final dehydrated leather material, or the filling materials could be sacrificial, that is they are degraded or dissolved away leaving open space for a more porous fibril network.

The collagen or collagen-like proteins may be chemically modified to promote chemical and physical crosslinking between the collagen fibrils. Collagen-like proteins were taught in the United States patent application US 2012/0116053 A1, which is hereby incorporated by reference. Chemical crosslinking may be possible because reactive groups such as lysine, glutamic acid, and hydroxyl groups on the collagen molecule project from collagen's rod-like fibril structure. Crosslinking that involve these groups prevent the collagen molecules from sliding past each other under stress and thus increases the mechanical strength of the collagen fibers. Examples of chemical crosslinking reactions include but are not limited to reactions with the ε-amino group of lysine, or reaction with carboxyl groups of the collagen molecule.

Enzymes such as transglutaminase may also be used to generate crosslinks between glutamic acid and lysine to form a stable γ-glutamyl-lysine crosslink. Inducing crosslinking between functional groups of neighboring collagen molecules is known in the art. Crosslinking is another step that can be implemented here to adjust the physical properties obtained from the fibrillated collagen hydrogel-derived materials.

Once formed, the fibrillated collagen network may be further stabilized by incorporating molecules with di-, tri-, or multifunctional reactive groups that include chromium, amines, carboxylic acids, sulfates, sulfites, sulfonates, aldehydes, hydrazides, sulfhydryls, diazarines, aryl-, azides, acrylates, epoxides, or phenols.

The fibrillated collagen network may also be polymerized with other agents (e.g. polymers that are capable of polymerizing or other suitable fibers) that form a hydrogel or have fibrous qualities, which could be used to further stabilize the matrix and provide the desired end structure. Hydrogels based upon acrylamides, acrylic acids, and their salts may be prepared using inverse suspension polymerization. Hydrogels described herein may be prepared from polar monomers. The hydrogels used may be natural polymer hydrogels, synthetic polymer hydrogels, or a combination of the two. The hydrogels used may be obtained using graft polymerization, crosslinking polymerization, networks formed of water soluble polymers, radiation crosslinking, and so on. A small amount of crosslinking agent may be added to the hydrogel composition to enhance polymerization.

The viscosity of the collagen solution can range from 1 cP to 1000 cP at 20° C., including all values and ranges there between such as 10, 20, 30, 50, 75, 90, 100, 150, 225, 300, 400, 450, 500, 525, 575, 600, 650, 700, 800, 900 etc. The solutions can be poured, sprayed, painted, or applied to a surface. The viscosity may vary depending on how the final material is formed. Where a higher viscosity is desired, known thickening agents such as carboxymethylcellulose and the like can be added to the solution. Alternatively, the amount of collagen in the solution can be adjusted to vary the viscosity.

The flexibility in the collagen solution enables the production of new materials made entirely through the deposition of said collagen solution, for example the creation of biofabricated leather lace materials or 3-dimensional materials. In a sense, the collagen solution may function as a liquid leather to form, for example, biofabricated leather or bioleather. The liquid leather can be poured, pipetted, sprayed through a nozzle, or robotically applied or dip a secondary material into the liquid leather. A textured surface can be achieved through utilizing an apertured material in the formation process of the material. Liquid leather also enables the use of masking, stenciling and molding techniques. The application of the biofabricated leather solution also enables modifying the properties of the material to which it is applied. For example, the biofabricated leather solution can make the end material stronger, more supple, more rigid, more flexible, more elastic or softer.

As mentioned, a biofabricated leather material derived from the methods described above may have similar gross structural and physical characteristics as leathers produced from animal hides. In general, in addition to collagen produced by the present yeast cells, the biofabricated leather materials described herein may be derived from sources other than sheets or pieces of animal hide or skin, although animal hide or skin may be the source of the collagen used in preparing the fibrillated collagen. The source of the collagen or collagen-like proteins may be isolated from any animal (e.g. mammal, fish), or more particularly cell/tissue cultured, source (including in particular microorganism).

The biofabricated leather material may include agents that stabilize the fibril network contained therein or may contain agents that promote fibrillation. As mentioned in previous sections, cross-linking agents (to provide further stability), nucleating agents (to promote fibrillation), and additional polymerizing agents (for added stability) may be added to the collagen solution prior to fibrillation (or after) to obtain a fibrillated collagen material with desired characteristics (e.g. strength, bend, stretch, and so forth).

As mentioned, following dehydration or drying, the engineered biofabricated leather materials derived from the methods discussed above have a water content of 20% or less by weight, or 17.5% or less by weight, or 15% or less by weight, or 12.5% or less by weight, or 10% or less by weight. The water content of the engineered biofabricated leather materials may be fine-tuned in the finishing steps to obtain leather materials for differing purposes and desired characteristics.

As mentioned, any of these biofabricated leathers may be tanned (e.g., using a tanning agent including vegetable (tannins), chromium, alum, zirconium, titanium, iron salts, or a combination thereof, or any other appropriate tanning agent). Thus, in any of the resulting biofabricated leather materials described herein, the resulting material may include a percent (e.g., between 0.01% and 10%, or between 0.025% and 8%, or between 0.05% and 6%, or between 0.1% and 5%, or between 0.25% and 4%, or between 0.5% and 3%, or between 0.75% and 2.5%, or between 1% and 2%) of a residual tanning agent (e.g. tannin, chromium, etc.). Thus, the collagen fibrils in the resulting biofabricated leather material are modified to be tanned, e.g., cross-linked to resist degradation.

The biofabricated leather materials may be treated to provide surface textures. Suitable treatments include but are not limited to embossing, debossing, and vacuum forming with an apertured plate below the material. As is known in the art, the pressure and temperature at which the embossing and debossing are performed may vary depending on the desired texture and design. Surface coating and finishes known in the leather industry may be applied to the biofabricated leather materials.

As mentioned above, in any of the variations for making the biofabricated leathers described herein, the material could be tanned (cross-linked) as the collagen is fibrillated and/or separately after fibrillation has occurred, prior to dehydration. For example, tanning may include crosslinking using an aldehyde (e.g., Relugan GTW) and/or any other tanning agent. Thus in general a tanning agent includes any collagen fibril cross-linking agent such as aldehydes cross linkers, chromium, amine, carboxylic acid, sulfate, sulfite, sulfonate, aldehyde, hydrazide, sulfhydryl, diazirine, Some methods for making a material including a biofabricated leather material include providing a material, pretreating the material to make it suitable for bonding with collagen, applying collagen solution to the material and drying. Drying may include removing water through a vacuum, heated air drying, ambient air drying, heated pressing and pressure drying. Where pretreatment is required, the pretreatment is either cutting voids or holes into the material, chemically removing certain fibers and treating the material with a chemical or collagen solution. Other methods do not require a pretreatment of the material. Where pretreatment is not required, the material is either partially water soluble or retains collagen but allows water to pass through. Suitable mesh sizes range from 300 threads per square inch to 1 thread per square foot. As used herein, the term bonded or bonding to the fabric mean attached such that the biofabricated leather does not easily peel away from the fabric when pulled by hand. A suitable method for testing the efficacy of bonding is a peel strength test performed on an instrument such as an Instron material testing machine. Jaws of the machine are attached to the biofabricated leather material and the material which it was bonded to, and the jaws are pulled apart until the materials tear or separate. The force to tear is reported in N/mm. Suitable peel strengths range from about 0.5 N/mm N/cm$^2$ to 100 N/mm, including 0.75 N/mm to 75 N/mm, or 1 N/mm to 50 N/mm, 1.5 N/mm to 25 N/mm, including all ranges and sub-ranges defined by the recited upper and lower limits.

Hydroxylation of proline and lysine residues in a protein (e.g., collagen). The principal post-translational modifications of the polypeptides of proteins that contain proline and lysine, including collagen, are the hydroxylation of proline and lysine residues to yield 4-hydroxyproline, 3-hydroxyproline (Hyp) and hydroxylysine (Hyl), and glycosylation of the hydroxylysyl residues. These modifications are catalyzed by three hydroxylases—prolyl 4-hydroxylase, prolyl 3-hydroxylase, and lysyl hydroxylase—and two glycosyl transferases. In vivo these reactions occur until the polypeptides form the triple-helical collagen structure, which inhibits further modifications.

Prolyl-4-hydroxylase. This enzyme catalyzes hydroxylation of proline residues to (2S,4R)-4-hydroxyproline (Hyp). Gorres, et al., Critical Reviews in Biochemistry and Molecular Biology 45 (2): (2010) which is incorporated by reference. The Examples below employ tetrameric bovine prolyl-4-hydroxylase (2 alpha and 2 beta chains) encoded by P4HA (SEQ ID NO: 8 (optimized for *Pichia*) or SEQ ID NO: 15 (native)) and P4HB (SEQ ID NO: 9 (optimized for *Pichia*) or SEQ ID NO: 16 (native)), however, isoforms, orthologs, variants, fragments and prolyl-4-hydroxylase from non-bovine sources (e.g., human prolyl-4-hydroxylase) may also be used as long as they retain hydroxylase activity in a yeast host cell. Another example of P4HA1 is further described by www.omim.org/entry/176710 (Cytogenetic location: 10q22.1; Genomic coordinates (GRCh38): 10:73,007,216-73,096,973 (from NCBI)) and another example of P4HB1 is further described by www.omim.org/entry/176790 (Cytogenetic location: 17q25.3; Genomic coordinates (GRCh38): 17:81,843,157-81,860,667 (from NCBI)) both of which are incorporated by reference.

In the context of the present application a "variant" includes an amino acid sequence having at least 70%, 75%, 80%, 85%, 87.5%, 90%, 92.5%, 95%, 97.5%, 98%, or 99% sequence identity, or similarity to a reference amino acid, such as a P4HA and P4HB amino acid sequence, using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Other default settings for BLASTP are described by and incorporated by reference to the disclosure available at: blast.ncbi.nlm.nih.gov/Blast.cgi?PROGRAM=blastp&PAGE_TYPE=BlastSearch&LINK_LOC=blasthome (last accessed Aug. 14, 2017). Within the present invention, the "variant" retains prolyl-4-hydroxylase activity.

In an embodiment of the present invention, yeast cells are engineered to overproduce the prolyl-4-hydroxylase. A non-limiting example is the incorporation of a polynucleotide encoding the prolyl-4-hydroxylase, an isoform thereof, an ortholog thereof, a variant thereof, or a fragment thereof which expresses prolyl-4-hydroxylase activity into an expression vector. In an embodiment of the present invention, the expression vector containing the polynucleotide encoding the prolyl-4-hydroxylase, an isoform thereof, an ortholog thereof, a variant thereof, or a fragment thereof which expresses prolyl-4-hydroxylase activity is under the control of an inducible promoter. Suitable yeast cells, expression vectors, and promoters are described below.

Prolyl 3-hydroxylase. This enzyme catalyzes hydroxylation of proline residues. 3-hydroxylase 1 precursor [*Bos taurus*] is described by NCBI Reference Sequence: NP_001096761.1 (SEQ ID NO: 4) or by NM_001103291.1 (SEQ ID NO: 5). For further description see Vranka, et al., J. Biol. Chem. 279: 23615-23621 (2004) or www.omim.org/entry/610339 (last accessed Jul. 14, 2017) which is incorporated by reference. This enzyme may be used in its native form. However, isoforms, orthologs, variants, fragments and prolyl-3-hydroxylase from non-bovine sources may also be used as long as they retain hydroxylase activity in a yeast host cell.

In the context of the present application a "variant" includes an amino acid sequence having at least 70%, 75%, 80%, 85%, 87.5%, 90%, 92.5%, 95%, 97.5%, 98%, or 99% sequence identity, or similarity to a reference amino acid, such as a prolyl-3-hydroxylase amino acid sequence, using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Other default settings for BLASTP are described by and incorporated by reference to the disclosure available at: /blast.ncbi.nlm.nih.gov/Blast.cgi?PROGRAM=blastp&PAGE_TYPE=

BlastSearch&LINK_LOC=blasthome (last accessed Aug. 14, 2017). Within the present invention, the "variant" retains prolyl-4-hydroxylase activity.

In an embodiment of the present invention, yeast cells are engineered to overproduce the prolyl-3-hydroxylase. A non-limiting example is the incorporation of a polynucleotide encoding the prolyl-3-hydroxylase, an isoform thereof, an ortholog thereof, a variant thereof, or a fragment thereof which expresses prolyl-3-hydroxylase activity into an expression vector. In an embodiment of the present invention, the expression vector containing the polynucleotide encoding the prolyl-3-hydroxylase, an isoform thereof, an ortholog thereof, a variant thereof, or a fragment thereof which expresses prolyl-3-hydroxylase activity is under the control of an inducible promoter. Suitable yeast cells, expression vectors, and promoters are described below.

Lysyl hydroxylase. Lysyl hydroxylase (EC 1.14.11.4) catalyzes the formation of hydroxylysine by the hydroxylation of lysine residues in X-lys-gly sequences. The enzyme is a homodimer consisting of subunits with a molecular mass of about 85 kD. No significant homology has been found between the primary structures of lysyl hydroxylase and the 2 types of subunits of prolyl-4-hydroxylase (176710, 176790) despite the marked similarities in kinetic properties between these 2 collagen hydroxylases. The hydroxylysine residues formed in the lysyl hydroxylase reaction in, for example, collagen have 2 important functions: first, their hydroxy groups serve as sites of attachment for carbohydrate units, either the monosaccharide galactose or the disaccharide glucosylgalactose; and second, they stabilize intermolecular collagen crosslinks.

An exemplary lysyl hydroxylase is PLOD1 procollagen-lysine,2-oxoglutarate 5-dioxygenase 1 [Bos taurus (cattle)] is described by Gene ID: 281409 (SEQ ID NO: 6), updated on 25 May 2017 and incorporated by reference to www.ncbi.nlm.nih.gov/gene/281409 (last accessed Jul. 14, 2017). Another example is described by SEQ ID NO: 7 which describes Bos taurus lysyl oxidase (LOX). Yet another example is described in SEQ ID NO: 14, which is a Bos taurus bifunctional arginine demethylase and lysyl-hydroxylase JMJD6. The lysyl hydroxylase enzyme may be used in its native form. However, isoforms, orthologs, variants, fragments and lysyl hydroxylase from non-bovine sources may also be used as long as they retain hydroxylase activity in a yeast host cell.

In the context of the present application a "variant" includes an amino acid sequence having at least 70%, 75%, 80%, 85%, 87.5%, 90%, 92.5%, 95%, 97.5%, 98%, or 99% sequence identity, or similarity to a reference amino acid, such as a lysyl hydroxylase amino acid sequence, using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Other default settings for BLASTP are described by and incorporated by reference to the disclosure available at: blast.ncbi.nlm.nih.gov/Blast.cgi?PROGRAM=blastp&PAGE_TYPE=BlastSearch&LINK_LOC=blasthome (last accessed Aug. 14, 2017). Within the present invention, the "variant" retains prolyl-4-hydroxylase activity.

In an embodiment of the present invention, yeast cells are engineered to overproduce the lysyl hydroxylase. A non-limiting example is the incorporation of a polynucleotide encoding the lysyl hydroxylase, an isoform thereof, an ortholog thereof, a variant thereof, or a fragment thereof which expresses lysyl hydroxylase activity into an expression vector. In an embodiment of the present invention, the expression vector containing the polynucleotide encoding the lysyl hydroxylase, an isoform thereof, an ortholog thereof, a variant thereof, or a fragment thereof which expresses lysyl hydroxylase activity is under the control of an inducible promoter. Suitable yeast cells, expression vectors, and promoters are described below.

α ketoglutarate transporter. The kgtP gene exists in Escherichia coli and encodes an a ketoglutarate transporter which is responsible for uptake of α ketoglutarate across the boundary membrane and concomitant import of a cation (Membrane Topology Model of Escherichia coli oL-Ketoglutarate Permease by PhoA Fusion Analysis, WONGI SEOLt AND AARON J. SHATKIN, JOURNAL OF BACTERIOLOGY, January 1993, p. 565-567). The gene has been transformed into cyanobacteria (Uptake of 2-Oxoglutarate in Synechococcus Strains Transformed with the Escherichia coli kgtP Gene, MARÍA FÉLIX VÁZQUEZ-BERMÚ DEZ, ANTONIA HERRERO, AND ENRIQUE FLORES, JOURNAL OF BACTERIOLOGY, January 2000, p. 211-215).

The inventors have found that transforming the kgtP gene into yeast provides a healthier organism. Furthermore, if the yeast produces a protein such as collagen or a carbohydrate, the transformed yeast have increased protein or carbohydrate production and improved hydroxylation of the collagen by making more α ketoglutarate available at the endoplasmic reticulum, where proteins or carbohydrates are made and hydroxylation occurs.

An exemplary kgtP gene is set forth in SEQ ID NO: 2, while an exemplary a ketoglutarate transporter is set forth in SEQ ID NO: 1. This enzyme may be used in its native form. However, isoforms, orthologs, variants, fragments and α ketoglutarate transporter from non-E. coli sources may also be used as long as they retain α ketoglutarate transporter activity in a yeast host cell. Further, the kgtP gene may be optimized for expression in yeast. For example, an example of an optimized α ketoglutarate transporter gene (kgtP) for expression in Pichia is set forth in SEQ ID NO: 3.

In the context of the present application a "variant" includes an amino acid sequence having at least 70%, 75%, 80%, 85%, 87.5%, 90%, 92.5%, 95%, 97.5%, 98%, or 99% sequence identity, or similarity to a reference amino acid, such as a α ketoglutarate transporter amino acid sequence, using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Other default settings for BLASTP are described by and incorporated by reference to the disclosure available at: blast.ncbi.nlm.nih.gov/Blast.cgi?PROGRAM=blastp&PAGE_TYPE=BlastSearch&LINK_LOC=blasthome (last accessed Aug. 14, 2017). Within the present invention, the "variant" retains prolyl-4-hydroxylase activity.

In an embodiment of the present invention, yeast cells are engineered to overproduce the α ketoglutarate transporter. A non-limiting example is the incorporation of a polynucleotide encoding the α ketoglutarate transporter, an isoform thereof, an ortholog thereof, a variant thereof, or a fragment thereof which expresses α ketoglutarate transporter activity into an expression vector. In an embodiment of the present invention, the expression vector containing the polynucleotide encoding the α ketoglutarate transporter, an isoform thereof, an ortholog thereof, a variant thereof, or a fragment thereof which expresses α ketoglutarate transporter activity is under the control of an inducible promoter. Suitable yeast cells, expression vectors, and promoters are described below.

Polynucleotide(s) Encoding One or More Polypeptides that Enable an Ascorbate Synthesis Pathway to Function L-ascorbic acid, ascorbate biosynthetic pathway in yeast, plants and animals is described, e.g., in Smirnoff (2001) Vitamins & Hormones 61-241-266 and Vitamin C. Functions and biochemistry in animals and plants Asard et al (ed.). Garland Science/BIOS Scientific Publishers, 2004. Various genes, individually or in combination may be used to enable the ascorbate synthesis in yeast. Those include, for example, for a plant pathway, the genes or polynucleotides encoding GDP-L-Gal phosphorylase which converts GDP-L-Galactose to L-Galactose-1-P, Inositol-phosphate phosphatase which converts L-Galactose-1-P to L-Galactose, GDP-Mannose-3,5-epimerase which converts GDP-D-Mannose to GDP-L-Galactose may be transformed into the yeast. Pichia already has the other genes necessary to complete the pathway. Those genes provide the following enzymes: hexokinase, Glucose-6-phosphate-isomerase, Mannose-6-phosphate-isomerase, Phosphomannomutase and Mannose-1-phosphate-guanylyltransferase.

For an animal pathway, the following genes can be added: L-gulono-1,4-lactone oxidase which converts L-Gulono-1,4-lactone to L-Ascorbate, aldonolactonase which converts L-Gulonic acid to L-Gulono-1,4-lactone, glucurono lactone reductase which converts D-Glucuronic acid to D-Glucurono lactone, D-glucuronate reductase which converts D-Glucuronic acid to L-Gulonic acid, uronolactonase which converts D-Glucuronic acid to D-Glucurono lactone, D-glucurono kinase which converts D-Glucuronic acid-1-P to D-Glucuronic acid, glucuronate-1-phosphate uridylyltransferase which converts UDP-Glucuronic acid to D-Glucuronic acid-1-P, UDP-D-glucose dehydrogenase which converts UDP-D-Glucose to UDP-Glucuronic acid, UTP-glucose-1-phosphate uridylyltransferase which converts D-Glucose-1-P to UDP-D-Glucose, phosphoglucomutase which converts D-Glc-6-P to D-Glucose-1-P, and/or hexokinase which converts D-Glucose to D-Glc-6-P.

It is not necessary to transform all of the genes for all of the enzymes to enable the yeast to make ascorbate. Indeed, in the present invention, it is envisioned that it is only necessary to insert one or more of the genes encoding proteins for the portion of the ascorbate synthesis pathway downstream from the ascorbate pathway precursor fed to the yeast cells. For example, one can insert the gene for the enzyme Inositol-phosphate phosphatase which converts L-Galactose-1-P to L-Galactose in to the yeast and then feed L-Galactose-1-P to the yeast, which allows the yeast to produce L-ascorbate.

GDP-L-Gal phosphorylase may be provided from Arabidopsis thaliana and include all or a part of the nucleotide sequence of SEQ ID NO: 21.

A representative amino acid sequence of GDP-L-Gal phosphorylase is as set forth in SEQ ID NO: 22.

Inositol-phosphate phosphatase (EC 3.1.3.25) is a known class of enzymes and is a phosphatase acting on L-galactose 1-phosphate (L-Gal 1-P), D-myoinositol 3-phosphate (D-Ins 3-P) and D-myoinositol 1-phosphate (D-Ins 1-P). Can also use beta-glycerophosphate (glycerol 2-P) and, to a lesser extent, D-galactose 1-phosphate (D-Gal 1-P), alpha-D-glucose 1-phosphate (a-D-Glc 1-P), D-manitol 1-phosphate and adenosine 2'-monophosphate as substrates. No activity with D-fructose 1-phosphate (D-Fru 1-P), fructose 1,6-bisphosphate (Fru 1,6-bisP) D-glucose 6-phosphate (D-Glc 6-P). D-alpha-glycerophosphate (glycerol 3-P), D-sorbitol 6-phosphate and D-myoinositol 2-phosphate. The C1 phosphate position in a six-member ring substrate is important for catalysis. Amino acid positions from Arabidopsis thaliana at 71, 91, 93, 94, and 221 contribute to metal binding and amino acid positions 71 and 213 contribute to substrate binding. A representative nucleotide sequence is shown in SEQ ID NO: 23.

One isoform of Inositol-phosphate phosphatase is shown in SEQ ID NO: 24.

GDP-Mannose-3,5-epimerase (EC 5.1.3.18) is a known class of enzymes and catalyzes a reversible epimerization of GDP-D-mannose that precedes the committed step in the biosynthesis of vitamin C (L-ascorbate), resulting in the hydrolysis of the highly energetic glycosyl-pyrophosphoryl linkage. Able to catalyze 2 distinct epimerization reactions and can release both GDP-L-galactose and GDP-L-gulose from GDP-mannose. In Arabidopsis thaliana, regions 143-145, 216-21 and/or 241-243 are involved in substrate binding with one or more positions 145, 174, 178, 217 and/or 306 involved in enzymatic activity and one or more of positions 58, 78, 174, and/or 178 involved in NAI) binding, one or more of positions 103, 203, 225, 306 and/or 356 involved in substrate biding.

The polynucleotide used herein may encode all or a part of the amino acid sequence of SEQ ID NO: 25.

L-gulono-1,4-lactone oxidase (EC 1.1.3.8) is a known class of enzymes and is involved in the biosynthesis of ascorbic acid. In Arabidopsis thaliana, position 156 is involved in activity and preferably only contains amino acids 102 to 610 or a fragment thereof with amino acids 123-258 involved in FAD binding.

The polynucleotide used herein may encode all or a part of the amino acid sequence of at least one isoform, for example of SEQ ID NO: 26.

A second isoform from the above sequence at 494-512 in which the sequence is changed from KSPISPAFSTSED-DIFSWV (SEQ ID NO: 27) and WYNHVPPDSRPS-PEKGHHR (SEQ ID NO: 28) and is missing 513-610.

Glucurono lactone reductase (EC 1.1.1.20) is a known class of enzymes and catalyzes a reaction of L-gulono-1,4-lactone+NADP(+)<=>D-glucurono-3,6-lactone+NADPH and is known in the art, e.g., from a number of organisms as outlined below from the publically accessible UniProt database:

| UNIPROT | ENTRY NAME | ORGANISM | NO. OF AA | MOLECULAR WEIGHT [Da] |
|---|---|---|---|---|
| Q3KFB7 pBLAST | Q3KFB7_PSEPF | *Pseudomonas fluorescens* (strain P10-1) | 797 | 87565 |
| B4ECW4 pBLAST | B4ECW4_BURCJ | *Burkholderia cenocepacta* (strain ATCC BAA-245/DSM 16553/ LMG 16656/NCTC 13227/J2315/CF5610) | 533 | 57165 |
| J7QMF7 pBLAST | J7QMF7_ECOLX | *Escherichia coli* | 229 | 24313 |
| G8Q002 pBLAST | G8Q002_PSEFL | *Pseudomonas fluorescens* F113 | 799 | 87653 |
| Q0JZZ6 pBLAST | Q0JZZ6_CUPNH | *Cupriavidus necator* (strain ATCC 17699/H16/DSM 428/Stanier 337) | 177 | 18548 |
| Q63RE5 pBLAST | Q63RE5_BURPS | *Burkholderia pseudomallei* (strain K96243) | 787 | 84441 |
| Q3JPB6 pBLAST | Q3JPB6_BURP1 | *Burkholderia pseudomallei* (strain 1710b) | 505 | 54737 |
| B4ECW3 pBLAST | B4ECW3_BURCJ | *Burkholderia cenocepacta* (strain ATCC BAA-245/DSM 16553/ LMG 16656/NCTC 13227/J2315/CF5610) | 787 | 84879 |
| C3KN28 pBLAST | C3KN28_SINFN | *Sinorhizobium fredii* (strain NBRC 101917/NGR234) | 117 | 12377 |
| J7RQ89 pBLAST | J7RQ89_ECOLX | *Escherichia coli* chi7122 | 229 | 24313 |
| Q63RE4 pBLAST | Q63RE4_BURPS | *Burkholderia pseudomallei* (strain K96243) | 505 | 54737 |
| C9YHB1 pBLAST | C9YHB1_9BURK | Curvibacter putative symbiont of *Hydra magnipapillata* | 755 | 81539 |
| Q3JPB7 pBLAST | Q3JPB7_BURP1 | *Burkholderia pseudomallei* (strain 1710b) | 787 | 84441 |
| C3JZH5 pBLAST | C3JZH5_PSEFS | *Pseudomonas fluorescens* (strain SBW25) | 799 | 87677 |

Aldonolactonase is known in the art and in some instances is also called a a gluconolactonase (EC 3.1.1.17) and is known from a number of organisms as outlined below from the publically accessible UniProt database:

| Entry | Entry name | Gene names | Organism | Length |
|---|---|---|---|---|
| G8Q002 | G8Q002_PSEFL | PSF113_4031 | *Pseudomonas fluorescens* F113 | 799 |
| J7QMF7 | J7QMF7_ECOLX | yagT cutS, AA102_15875, ACN002_0308, ACN77_07560, ACN81_05350 | *Escherichia coli* | 229 |
| Q63RE4 | Q63RE4_BURPS | xdhA BPSL2728 | *Burkholderia pseudomallei* (strain K96243) | 505 |
| B4ECW4 | B4ECW4_BURCJ | xdhA BCAL3173 | *Burkholderia cenocepacia* (strain ATCC BAA-245/DSM 16553/LMG 16656/NCTC 13227/J2315/ CF5610) (*Burkholderia cepacia* (strain J2315)) | 533 |
| Q3JPB6 | Q3JPB6_BURP1 | xdhA BURPS1710b_3215 | *Burkholderia pseudomallei* (strain 1710b) | 505 |
| C9YHB1 | C9YHB1_9BURK | XDH Csp_B21610 | *Curvibacter putative symbiont of Hydra magnipapillata* | 755 |
| Q0JZZ6 | Q0JZZ6_CUPNH | xdhC2 H16_B1896 | *Cupriavidus necator* (strain ATCC 17699/ H16/DSM 428/ Stanier 337) (*Ralstonia eutropha*) | 177 |
| C3KN28 | C3KN28_SINFN | yagT NGR_b01350 | *Sinorhizobium fredii* (strain NBRC 101917/ NGR234) | 117 |

-continued

| Entry | Entry name | Gene names | Organism | Length |
|---|---|---|---|---|
| J7RQ89 | J7RQ89_ECOLX | yagT BN16_07581 | *Escherichia coli* chi7122 | 229 |
| Q63RE5 | Q63RE5_BURPS | xdhB BP5L2727 | *Burkholderia pseudomallei* (strain K96243) | 787 |
| B4ECW3 | B4ECW3_BURCJ | xdhB BCAL3172 | *Burkholderia cenocepacia* (strain ATCC BAA-245/DSM 16553/LMG 16656/NCTC 13227/J2315/ CF5610) (*Burkholderia cepacia* (strain J2315)) | 787 |
| Q3JPB7 | Q3JPB7_BURP1 | xdhB BURPS1710b_3213 | *Burkholderia pseudomallei* (strain 1710b) | 787 |
| Q3KFB7 | Q3KFB7_PSEPF | Pfl01_1796 | *Pseudomonas fluorescens* (strain Pf0-1) | 797 |
| C3JZH5 | C3JZH5_PSEFS | PFLU_4593 | *Pseudomonas fluorescens* (strain SBW25) | 799 |
| A0A1W1B2Y5 | A0A1W1B2Y5_9BURK | xdhA UA11_02398, UA12_02333 | *Burkholderia multivorans* | 531 |
| A0A1W0Z2H1 | A0A1W0Z2H1_9BURK | xdhA UA14_02405, UA16_02328 | *Burkholderia multivorans* | 531 |
| A0A1W1A395 | A0A1W1A395_9BURK | xdhA UA19_02501, UA21_02488 | *Burkholderia multivorans* | 531 |
| A0A1W0ZBE9 | A0A1W0ZBE9_9BURK | xdhA UA17_00017 | *Burkholderia multivorans* | 521 |
| A0A1W1A6N7 | A0A1W1A6N7_9BURK | xdhA UA18_02826 | *Burkholderia multivorans* | 531 |

D-glucuronate reductase (EC 1.1.1.19) is a known class of enzymes and, e.g., from a number of organisms as outlined below from the publically accessible UniProt database

| Entry | Entry name | Gene names | Organism | Length |
|---|---|---|---|---|
| P14550 | AK1A1_HUMAN | AKR1A1 ALDR1, ALR | *Homo sapiens* (Human) | 325 |
| Q9UGB7 | MIOX_HUMAN | MIOX ALDRL6, KSP32, RSOR | *Homo sapiens* (Human) | 285 |
| Q9QXN5 | MIOX_MOUSE | Miox Aldrl6, Rsor | *Mus musculus* (Mouse) | 285 |
| O35082 | KLOT_MOUSE | Kl | *Mus musculus* (Mouse) | 1,014 |
| Q8WN98 | MIOX_PIG | MIOX ALDRL6 | *Sus scrofa* (Pig) | 282 |
| Q9JII6 | AK1A1_MOUSE | Akr1a1 Akr1a4 | *Mus musculus* (Mouse) | 325 |
| P51635 | AK1A1_RAT | Akr1a1 Alr | *Rattus norvegicus* (Rat) | 325 |
| Q9QXN4 | MIOX_RAT | Miox Aldrl6, Ksp32, Rsor | *Rattus norvegicus* (Rat) | 285 |
| P37769 | KDUD_ECOLI | kduD yqeC, yqeD, b2842, JW2810 | *Escherichia coli* (strain K12) | 253 |
| Q3ZCJ2 | AK1A1_BOVIN | AKR1A1 | *Bos taurusi* (Bovine) | 325 |
| Q3ZFI7 | GAR1_HYPJE | gar1 | *Hypocrea jecorina* (*Trichoderma reesei*) | 309 |
| Q5REY9 | MIOX_PONAB | MIOX | *Pongo abelii* (Sumatran orangutan) (*Pongo pygmaeus abelii*) | 285 |
| P39160 | UXUB_ECOLI | uxuB b4323, JW4286 | *Escherichia coli* (strain K12) | 486 |
| H2PYX5 | H2PYX5_PANTR | AKR1A1 | *Pan troglodytes* (Chimpanzee) | 325 |
| Q540D7 | Q540D7_MOUSE | Akr1a1 Akr1a4 | *Mus musculus* (Mouse) | 325 |
| H0ZCF8 | H0ZCF8_TAEGU | AKR1A1 | *Taeniopygia guttata* (Zebra finch) (*Poephila guttata*) | 327 |
| K7FUR5 | K7FUR5_PELSI | AKR1A1 | *Pelodiscus sinensis* (Chinese softshell turtle) (*Trionyx sinensis*) | 327 |
| F1PK43 | F1PK43_CANLF | AKR1A1 | *Canis lupus familiaris* (Dog) (*Canis familiaris*) | 325 |
| M3VZ98 | M3VZ98_FELCA | AKR1A1 | *Felis catus* (Cat) (*Felis silvestris catus*) | 325 |
| H0WVS3 | H0WVS3_OTOGA | AKR1A1 | *Otolemur garnettii* (Small-eared galago) (Garnett's greater bushbaby) | 325 |

| Entry | Entry name | Gene names | Organism | Length |
|---|---|---|---|---|
| G1NT89 | G1NT89_MYOLU | AKR1A1 | *Myotis lucifugus* (Little brown bat) | 325 |
| I3ML55 | I3ML55_ICTTR | AKR1A1 | *Ictidomys tridecemlineatus* (Thirteen-lined ground squirrel) (*Spermophilus tridecemlineatus*) | 325 |
| H0VM25 | H0VM25_CAVPO | AKR1A1 | *Cavia porcellus* (Guinea pig) | 325 |
| M3YNR9 | M3YNR9_MUSPF | AKR1A1 | *Mustela putorius furo* (European domestic ferret) (*Mustela furo*) | 325 |
| G3W2S6 | G3W2S6_SARHA | AKR1A1 | *Sarcophilus harrisii* (Tasmanian devil) (*Sarcophilus laniarius*) | 325 |
| U3K4S3 | U3K4S3_FICAL | AKR1A1 | *Ficedula albicollis* (Collared flycatcher) (*Muscicapa albicollis*) | 327 |
| A0A0D9S7F8 | A0A0D9S7F8_CHLSB | AKR1A1 | *Chlorocebus sabaeus* (Green monkey) (*Cercopithecus sabaeus*) | 325 |
| G1M4Y1 | G1M4Y1_AILME | AKR1A1 | *Ailuropoda melanoleuca* (Giant panda) | 326 |
| F6XYQ0 | F6XYQ0_CALJA | AKR1A1 | *Callithrix jacchus* (White-tufted-ear marmoset) | 325 |
| W5NUN8 | W5NUN8_SHEEP | AKR1A1 | *Ovis aries* (Sheep) | 325 |
| A0A096N138 | A0A096N138_PAPAN | AKR1A1 | *Papio anubis* (Olive baboon) | 325 |
| H2N7K8 | H2N7K8_PONAB | AKR1A1 | *Pongo abelii* (Sumatran orangutan) (*Pongo pygmaeus abelii*) | 325 |
| F6R8L7 | F6R8L7_ORNAN | AKR1A1 | *Ornithorhynchus anatinus* (Duckbill platypus) | 327 |
| H9GLX5 | H9GLX5_ANOCA | AKR1A1 | *Anolis carolinensis* (Green anole) (American chameleon) | 358 |
| U3II47 | U3II47_ANAPL | AKR1A1 | *Anas platyrhynchos* (Mallard) (*Anas boschas*) | 328 |
| F7CBN0 | F7CBN0_HORSE | AKR1A1 | *Equus caballus* (Horse) | 324 |
| I3L929 | I3L929_PIG | AKR1A1 | *Sus scrofa* (Pig) | 326 |
| F7GDV9 | F7GDV9_MONDO | AKR1A1 | *Monodelphis domestica* (Gray short-tailed opossum) | 325 |
| G1NDE3 | G1NDE3_MELGA | AKR1A1 | *Meleagris gallopavo* (Common turkey) | 329 |
| G3RAF6 | G3RAF6_GORGO | AKR1A1 | *Gorilla gorilla gorilla* (Western lowland *gorilla*) | 298 |
| G3U0I8 | G3U0I8_LOXAF | AKR1A1 | *Loxodonta africana* (African elephant) | 325 |
| V9HWI0 | V9HWI0_HUMAN | HEL-S-165mP HEL-S-6 | *Homo sapiens* (Human) | 325 |
| A0A1V1TUJ3 | A0A1V1TUJ3_9FUNG | aguA ANO14919_141650 | fungal sp. No. 14919 | 838 |
| B1AXW3 | B1AXW3_MOUSE | Akr1a1 | *Mus musculus* (Mouse) | 203 |
| Q7CPT2 | Q7CPT2_SALTY | STM3136 | *Salmonella typhimurium* (strain LT2/SGSC1412/ATCC 700720) | 490 |

Uronolactonase is a known class of enzymes (EC 3.1.1.19) and catalyzes the reaction of D-glucurono-6,2-lactone+H(2)O<=>D-glucuronate and is also known as glucuronolactonase or D-glucurono-6,2-lactone lactonohydrolase and a number of enzymes associated with this enzymatic activity are known, see EC 3.1.1.19.

D-glucuronokinase (EC 2.7,1,43) is a known class of enzymes and for instance from *Arabidopsis thaliana* is involved in the biosynthesis of UDP-glucuronic acid (UDP-GlcA) with amino acids 126-136 involved in binding. The polynucleotide used herein may encode all or a part of the amino acid sequence of SEQ II) NO: 29.

Glucuronate-1-phosphate uridylyltransferase is a known class of enzymes (EC 2.7.7.44) that catalyzes the chemical reaction UTP+1-phospho-alpha-D-glucuronate to diphosphate+UDP-glucuronate and is known in the art, e.g., from a number of organisms as outlined below from the publically accessible UniProt database:

| Entry | Entry name | Gene names | Organism | Length |
|---|---|---|---|---|
| Q9C5I1 | USP_ARATH | USP At5g52560, F6N7.4 | *Arabidopsis thaliana* (Mouse-ear cress) | 614 |
| Q5Z8Y4 | USP_ORYSJ | USP Os06g0701200, LOC_Os06g48760, OsJ_021664, P0596H10.4 | *Oryza sativa* subsp. *japonica* (Rice) | 616 |
| A8HP64 | A8HP64_CHLRE | UAP2 CHLREDRAFT_32796 | *Chlamydomonas reinhardtii* (*Chlamydomonas smithii*) | 831 |

| Entry | Entry name | Gene names | Organism | Length |
|---|---|---|---|---|
| I1GWP2 | I1GWP2_BRADI | LOC100845164 | *Brachypodium distachyon* (Purple false brome) (*Trachynia distachya*) | 610 |
| B9GTZ2 | B9GTZ2_POPTR | POPTR_0002s07790g | *Populus trichocarpa* (Western balsam poplar) (*Populus balsamifera* subsp. *trichocarpa*) | 522 |
| E0CR04 | E0CR04_VITVI | VIT_18s0001g01640 | *Vitis vinifera* (Grape) | 644 |
| K4BT00 | K4BT00_SOLLC | | *Solanum lycopersicum* (Tomato) (*Lycopersicon esculentum*) | 617 |
| A9TMZ5 | A9TMZ5_PHYPA | PHYPADRAFT_196551 | *Physcomitrella patens* subsp. *patens* (Moss) | 617 |
| M1C415 | M1C415_SOLTU | | *Solanum tuberosum* (Potato) | 624 |
| J3MHA9 | J3MHA9_ORYBR | | *Oryza brachyantha* | 611 |
| W1NLN3 | W1NLN3_AMBTC | AMTR_s00202p00022860 | *Amborella trichopoda* | 626 |
| M5XAU8 | M5XAU8_PRUPE | PRUPE_ppa003010mg | *Prunus persica* (Peach) (*Amygdalus persica*) | 612 |
| D7MS64 | D7MS64_ARALL | ARALYDRAFT_495327 | *Arabidopsis lyrata* subsp. *lyrata* (Lyre-leaved rock-cress) | 614 |
| A0A0J8D623 | A0A0J8D623_BETVU | BVRB_1g010300 | *Beta vulgaris* subsp. *vulgaris* | 620 |
| B8B249 | B8B249_ORYSI | OsI_24356 | *Oryza sativa* subsp. *indica* (Rice) | 627 |
| M8BEG3 | M8BEG3_AEGTA | F775_26791 | *Aegilops tauschii* (Tausch's goatgrass) (*Aegilops squarrosa*) | 583 |
| I1Q4Z2 | I1Q4Z2_ORYGL | | *Oryza glaberrima* (African rice) | 616 |
| M7ZGA3 | M7ZGA3_TRIUA | TRIUR3_12743 | *Triticum urartu* (Red wild einkorn) (*Crithodium urartu*) | 592 |
| A0A0D3DVG6 | A0A0D3DVG6_BRAOL | | *Brassica oleracea* var. *oleracea* | 619 |
| M4CUA3 | M4CUA3_BRARP | | *Brassica rapa* subsp. *pekinensis* (Chinese cabbage) (*Brassica pekinensis*) | 618 |
| A0A0E0Q285 | A0A0E0Q285_ORYRU | | *Oryza rufipogon* (Brownbeard rice) (Asian wild rice) | 616 |
| A0A0E0HUY3 | A0A0E0HUY3_ORYNI | | *Oryza nivara* (Indian wild rice) | 616 |
| A0A061FHA6 | A0A061FHA6_THECC | TCM_035220 | *Theobroma cacao* (Cacao) (Cocoa) | 621 |
| W5I0D4 | W5I0D4_WHEAT | | *Triticum aestivum* (Wheat) | 625 |
| A0A0E0ADY6 | A0A0E0ADY6_9ORYZ | | *Oryza glumipatula* | 616 |
| A0A0D3GKG7 | A0A0D3GKG7_9ORYZ | | *Oryza barthii* | 616 |
| A0A0D9WTS5 | A0A0D9WTS5_9ORYZ | | *Leersia perrieri* | 624 |

UDP-D-glucose dehydrogenase (EC 1.1.1.22) is a known class of enzymes that hat catalyzes the chemical reaction UDP-glucose+2 $NAD^+$+$H_2O$ UDP-glucuronate+2 NADH+ $2H^+$ (EC. 1.1.1.22) and may include all or a part of SEQ ID NO: 30.

Other sequences from the UniProt publican); available database are:

O33952, UDG8_ECOLX; Q04872, UDG_ECO11; Q7DBF9, UDG_ECO57;
Q8FG45, UDG_ECOL6; P76373, UDG_ECOLI; O86422, UDG_PSEAE;
O54068, UDG_RHIME; Q1RKF8, UDG_RICBR; Q92GB1, UDG_RICCN;
Q4UK39, UDG_RICFE; O05973, UDG_RICPR; Q68VX0, UDG_RICTY;
Q04873, UDG_SALTY; P37791, UDG_SHIFL; Q57346, UDG_STREE;
P0COF5, UDG_STRP1; P0DG68, UDG_STRP3; Q5X9A8, UDG_STRP6;
Q8NKX0, UDG_STRP8; P0DG69, UDG_STRPQ; P0COF4, UDG_STRPY;
Q9FZE1, UGDH1_ARATH; Q75GS4, UGDH1_ORYSJ; Q96558, UGDH1_SOYBN;
Q9LIA8, UGDH2_ARATH; B7F958, UGDH2_ORYSJ; Q9LF33, UGDH3_ARATH;
Q9AUV6, UGDH3_ORYSJ; Q9FM01, UGDH4_ARATH; Q2QS14, UGDH4_ORYSJ;
Q2QS13, UGDH5_ORYSJ; P12378, UGDH_BOVIN; Q19905, UGDH_CAEEL;

-continued

| | | |
|---|---|---|
| O5F3T9, UGDH_CHICK; | O02373, UGDH_DROME; | O60701, UGDH_HUMAN; |
| O70475, UGDH_MOUSE; | Q5R7B3, UGDH_PONAB; | O70199, UGDH_RAT; |
| O34862, YTCA_BACSU; | P96718, YWQF_BACSU; | |

UTP-glucose-1-phosphate uridylyltransferase (EC 2.7.7.9) is a known class of enzymes and is also known as glucose-1-phosphate uridylyltransferase (or UDP-glucose pyrophosphorylase) is an enzyme involved in carbohydrate metabolism. It synthesizes UDP-glucose from glucose-1-phosphate and UTP. There are hundreds of known sequences from various species associated with this class in the art.

Phosphoglucomutase (EC 5.4.2.2) is a known class of enzymes and is an enzyme that transfers a phosphate group on an α-D-glucose monomer from the 1' to the 6' position in the forward direction or the 6' to the 1' position in the reverse direction. There are hundreds of known sequences from various species associated with this class in the art.

Hexokinase (EC 2.7.1.1) is a known class of enzymes that phosphorylates hexoses (six-carbon sugars), forming hexose phosphate. There are hundreds of known sequences from various species associated with this class in the art.

Assay of degree of hydroxylation of proline residues in recombinant protein (e.g., collagen). The degree of hydroxylation of proline residues in recombinant protein (e.g., collagen) produced in accordance with the present invention may be assayed by known methods, including by liquid chromatography-mass spectrometry as described by Chan, et al., BMC Biotechnology 12:51 (2012) which is incorporated by reference.

Assay of degree of hydroxylation of lysine residues in recombinant protein (e.g., collagen). Lysine hydroxylation and cross-linking of collagen is described by Yamauchi, et al., Methods in Molecular Biology, vol. 446, pages 95-108; Humana Press (2008) which is incorporated by reference. The degree of hydroxylation of lysine residues in recombinant protein (e.g., collagen) produced in accordance with the present invention may be assayed by known methods, including by the method described by Hausmann, Biochimica et Biophysica Acta (BBA)—Protein Structure 133(3): 591-593 (1967) which is incorporated by reference.

Degree of hydroxylation. The degree of hydroxylation of proline or lysine residues in protein (e.g., collagen) produced in accordance with the present invention is preferably at least 10%, 15%, 20%, 25%, 30%, 35%, 40%, 45%, 50%, 55%, 60%, 65%, 70%, 75%, 80%, 85%, 90%, or 100%. Also within the scope of the present invention the degree of hydroxylation of proline plus lysine residues is at least 10%, 15%, 20%, 25%, 30%, 35%, 40%, 45%, 50%, 55%, 60%, 65%, 70%, 75%, 80%, 85%, 90%, or 100%.

Collagen Melting Point. The degree of hydroxylation of proline, lysine or proline and lysine residues in collagen may be estimated by melting temperature of a hydrated collagen, such as a hydrogel compared to a control collagen having a known content of hydroxylated amino acid residues. Collagen melting temperatures can range from 25-40° C. with more highly hydroxylated collagens generally having higher melting temperatures. This range includes all intermediate subranges and values including subranges that are bound on the lower and upper end by a temperature selected from 25, 26, 28, 29, 30, 31, 32, 33, 34, 35, 36, 37, 38, 39 and 40° C.

Codon-modification. Within the scope of the present invention it is envisioned that the gene sequence introduced into the yeast host cell is modified from its native sequence. This process includes alteration of a polynucleotide sequence encoding the protein of interest (e.g. collagen, such as collagen DNA sequence found in nature), to modify the amount of recombinant protein (e.g., collagen) expressed by a yeast, such as Pichia pastoris, to modify the amount of recombinant protein (e.g., collagen) secreted by the recombinant yeast, to modify the speed of expression of recombinant protein (e.g., collagen) in the recombinant yeast, or to modify the degree of hydroxylation of lysine or proline residues in the recombinant protein (e.g., collagen). Codon modification may also be applied to other proteins such as hydroxylases for similar purposes or to target hydroxylases to particular intracellular or extracellular compartments, for example to target a proline hydroxylase to the same compartment, such as the endoplasmic reticulum, as recombinant protein (e.g., collagen) molecule. Codon selections may be made based on effect on RNA secondary structure, effect on transcription and gene expression, effect on the speed of translation elongation, and/or the effect on protein folding.

Codons encoding collagen or a hydroxylase may be modified to reduce or increase secondary structure in mRNA encoding recombinant collagen or the hydroxylase or may be modified to replace a redundant codon with a codon which, on average, is used most frequently by a yeast host cell based on all the protein-coding sequences in the yeast (e.g., codon sampling), is used least frequently by a yeast host cell based on all the protein-coding sequences in the yeast (e.g., codon sampling), or redundant codons that appear in proteins that are abundantly-expressed by yeast host cells or which appear in proteins that are secreted by yeast host cells (e.g., a codon selection based on a High Codon Adaptation Index that makes the gene "look like" a highly expressed gene or gene encoding a secretable protein from the expression host).

Codon-modification may be applied to all or part of a protein-coding sequence, for example, to at least one of the first, second, third, fourth, fifth, sixth, seventh, eighth, ninth or tenth 10% of a coding-sequence or combinations thereof. It may also be applied selectively to a codon encoding a particular amino acid or to codons encoding some but not all amino acids that are encoded by redundant codons. For example, only codons for leucine and phenylalanine may be codon-modified as described above. Amino acids encoded by more than one codon are described by the codon table, which is well-known in the art.

Codon-modification includes the so-called codon-optimization methods described by www.atum.bio/services/genegps (last accessed Jul. 13, 2017), by www.idtdna.com/CodonOpt or Villalobos, Alan et al. BMC Bioinformatics 7 (2006): 285. PMC. Web. 17 Aug. 2017, incorporated herein by reference.

Codon-modification also includes selection of codons so as to permit formation of mRNA secondary structure or to minimize or eliminate secondary structure. An example of this is making codon selections so as to eliminate, reduce or weaken secondary structure strong secondary structure at or around a ribosome-binding site or initiation codon.

In an embodiment of the present invention the α ketoglutarate transporter gene sequence is optimized for use in yeast, in particular *Pichia*. An example of a optimized α ketoglutarate transporter gene (kgtP) is set forth in SEQ ID NO: 3.

Collagen Fragments. A recombinant collagen molecule can comprise a fragment of the amino acid sequence of a native collagen molecule capable of forming tropocollagen (trimeric collagen) or a modified collagen molecule or truncated collagen molecule having an amino acid sequence at least 70, 80, 90, 95, 96, 97, 98, or 99% identical or similar to a native collagen amino acid sequence (or to a fibril forming region thereof or to a segment substantially comprising [Gly-X-Y]n), such as those of amino acid sequences of Col1A1, Col1A2, and Col3A1, described by Accession Nos. NP_001029211.1 (SEQ ID NO: 11) (www.ncbi.nlm.nih.gov/protein/77404252, last accessed Aug. 23, 2017), NP_776945.1 (SEQ ID NO: 12) (www.ncbi.nlm.nih.gov/protein/27806257last accessed Aug. 23, 2017) and NP_001070299.1 (SEQ ID NO: 13) (www.ncbi.nlm.nih.gov/protein/116003881 last accessed Feb. 9, 2017), respectively, which are incorporated by reference.

A gene encoding collagen or a hydroxylase may be truncated or otherwise modified to add or remove sequences. Such modifications may be made to customize the size of a polynucleotide or vector, to target the expressed protein to the endoplasmic reticulum or other cellular or extracellular compartment, or to control the length of an encoded protein. For example, the inventors found that constructs containing only the Pre sequence often work better than those containing the entire Pre-pro sequence. The Pre sequence was fused to P4HB to localize P4HB in the ER where collagen localizes as well.

Modified coding sequences for collagens and hydroxylases. A polynucleotide coding sequence for collagen or a hydroxylase, or other proteins, may be modified to encode a protein that is at least 70, 80, 90, 95, 96, 97, 98, or 100% identical or similar to a known amino acid sequence and which retains the essential properties of the unmodified molecule, for example, the ability to form tropocollagen or the ability to hydroxylase proline or lysine residues in collagen. Glycosylation sites in a collagen molecule may be removed or added. Modifications may be made to facilitate collagen yield or its secretion by a yeast host cell or to change its structural, functional, or aesthetic properties. A modified collagen or hydroxylase coding sequence may also be codon-modified as described herein.

BLASTN may be used to identify a polynucleotide sequence having at least 70%, 75%, 80%, 85%, 87.5%, 90%, 92.5%, 95%, 97.5%, 98%, 99% or <100% sequence identity to a reference polynucleotide such as a polynucleotide encoding a collagen, one or more hydroxylases described herein, or signal, leader or secretion peptides or any other proteins disclosed herein. A representative BLASTN setting modified to find highly similar sequences uses an Expect Threshold of 10 and a Wordsize of 28, max matches in query range of 0, match/mismatch scores of 1/−2, and linear gap cost. Low complexity regions may be filtered or masked. Default settings of a Standard Nucleotide BLAST are well-known in the art.

BLASTP can be used to identify an amino acid sequence having at least 70%, 75%, 80%, 85%, 87.5%, 90%, 92.5%, 95%, 97.5%, 98%, 99% or <100% sequence identity, or similarity to a reference amino acid, such as a collagen amino acid sequence, using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Other default settings for BLASTP are well known in the art.

The term "variant", "modified sequence" or "analog" as applied to the polypeptides disclosed herein, refers to a polypeptide comprising an amino acid sequence that is at least 70, 80, 90, 95, or 99% identical or similar to the amino acid sequence of a biologically active molecule. In some embodiments, the derivative comprises an amino acid sequence that is at least 75%, 80%, 85%, 86%, 87%, 88%, 89%, 90%, 91%, 92%, 93%, 94%, 95%, 96%, 97%, 98%, or 99% identical to the amino acid sequence of a native or previously engineered sequence. The derivative may comprise additions, deletions, substitutions, or a combination thereof to the amino acid sequence of a native or previously engineered molecule. For example, a derivative may incorporate or delete 1, 2, 3, 4, 5, 6, 7, 8, 9, 10 or more proline or lysine residues compared to a native collagen sequence. Such selections may be made to modify the looseness or tightness of a recombinant tropocollagen or fibrillated collagen.

A derivative may include a mutant polypeptide with 1, 2, 3, 4, 5, 6, 7, 8, 9, 10, 11-15, 16-20, 21-25, or 26-30 additions, substitutions, or deletions of amino acid residues. Additions or substitutions also include the use of non-naturally occurring amino acids or modified amino acids. A derivative may also include chemical modifications to a polypeptide, such as crosslinks between cysteine residues, or hydroxylated or glycosylated residues.

Yeast strains. The present invention utilizes yeast to produce collagen or other proteins or carbohydrates. In particular, the present invention utilizes modified yeast to produce collagen or other carbohydrates with an increased degree of hydroxylation. The yeast may be engineered to produce or overproduce α ketoglutarate and/or ascorbic acid by inserting one or more of a gene expression a kgtP gene, a gene expressing a hydroxylase, or gene(s) necessary to complete a functioning ascorbate synthesis pathway.

Suitable yeast includes, but is not limited to, those of the genus *Pichia, Candida, Komatagaella, Hansenula, Cryptococcus, Saccharomyces* and combinations thereof. The yeast may be modified or hybridized. Hybridized yeast is mixed breeding of different strains of the same species, different species of the same genus or strains of different genera. Examples of yeast strains that may be used according to the invention include *Pichia pastoris, Pichia membranifaciens, Pichia deserticola, Pichia cephalocereana, Pichia eremophila, Pichia myanmarensis, Pichia anomala, Pichia nakasei, Pichia siamensis, Pichia heedii, Pichia barkeri, Pichia norvegensis, Pichia thermomethanolica, Pichia stipites,*

*Pichia subpelliculosa, Pichia exigua, Pichia occidentalis, Pichia cactophila, Saccharomyces cerevisiae, Saccharomyces pombe,* and the like.

*Pichia pastoris* is a yeast species that has been used to recombinantly express biotherapeutic proteins, such as human interferon gamma, see Razaghi, et al., Biologicals 45: 52-60 (2017). It has been used to express type III collagen and prolyl-4-hydroxylase, see Vuorela, et al., EMBO J. 16:6702-6712 (1997). Collagen and prolyl-4-hydroxylase have also been expressed in *Escherichia coli* to produce a collagenous material, see Pinkas, et al., ACS Chem. Biol. 6(4):320-324 (2011).

In one embodiment, the invention is directed to *Pichia pastoris* strains that have been engineered to express codon-optimized collagen, hydroxylase(s), α ketoglutarate transporter, and/or gene(s) necessary to complete a functioning ascorbate synthesis pathway. Useful *Pichia pastoris* host strains include, but are not limited to, wild type (Strain PPS-9010); aox1Δ (MutS)(Strain PPS-9011) which is a slow methanol utilization derivative of PPS-9010; and pep4Δ, prb1Δ (Strain PPS-9016) which is protease deficient. These strains are publically available and may be obtained from ATUM at https://www.atum.bio/products/cell-strains.

Polypeptide secretion sequences for yeast. In some embodiments, a polypeptide encoded by a yeast host cell is fused to a polypeptide sequence that facilitates its secretion from the yeast. For example, a vector may encode a chimeric gene comprising a coding sequence for collagen fused to a sequence encoding a secretion peptide. Secretion sequences which may be used for this purpose include *Saccharomyces* alpha mating factor Prepro sequence, *Saccharomyces* alpha mating factor Pre sequence, PHO1 secretion signal, α-amylase signal sequence from *Aspergillus niger*, Glucoamylase signal sequence from *Aspergillus awamori*, Serum albumin signal sequence from *Homo sapiens*, Inulinase signal sequence from *Kluyveromcyes maxianus*, Invertase signal sequence from *Saccharomyces cerevisiae*, Killer protein signal sequence from *Saccharomyces cerevisiae* and Lysozyme signal sequence from *Gallus gallus*. Other secretion sequences known in the art may also be used.

Yeast promoters and terminators. In some embodiments one or more of the following yeast promoters may be incorporated into a vector to promoter transcription of mRNA encoding the protein of interest (e.g., collagen), hydroxylase(s), α ketoglutarate transporter, and/or gene(s) necessary to complete a functioning ascorbate synthesis pathway. Promoters are known in the art and include pAOX1, pDas1, pDas2, pPMP20, pCAT, pDF, pGAP, pFDH1, pFLD1, pTAL1, pFBA2, pAOX2, pRKI1, pRPE2, pPEX5, pDAK1, pFGH1, pADH2, pTPI1, pFBP1, pTAL1, pPFK1, pGPM1, and pGCW14.

In some embodiments a yeast terminator sequence is incorporated into a vector to terminate transcription of mRNA encoding the protein of interest (e.g., collagen), hydroxylase(s), α ketoglutarate transporter, and/or gene(s) necessary to complete a functioning ascorbate synthesis pathway. Terminators include but are not limited to AOX1 TT, Das1 TT, Das2 TT, AOD TT, PMP TT, Cat1 TT, TPI TT, FDH1 TT, TEF1 TT, FLD1 TT, GCW14 TT, FBA2 TT, ADH2 TT, FBP1 TT, and GAP TT.

Peptidases other than pepsin. Pepsin may be used to process collagen into tropollagen by removing N-terminal and C-terminal sequences. Other proteases, including but not limited to collagenase, trypsin, chymotrypsin, papain, ficain, and bromelain, may also be used for this purpose. As used herein, "stable collagen" means that after being exposed to a particular concentration of pepsin or another protease that at least 20, 30, 40, 50, 60, 75, 80, 85, 90, 95 or 100% of the initial concentration of collagen is still present. Preferably, at least 75% of a stable collagen will remain after treatment with pepsin or another protease as compared to an unstable collagen treated under the same conditions for the same amount of time. Prior to post-translational modification, collagen is non-hydroxylated and degrades in the presence of a high pepsin concentration (e.g., a pepsin:protein ratio of 1:200 or more).

Once post-translationally modified a collagen may be contacted with pepsin or another protease to cleave the N-terminal and the C-terminal propeptides of collagen, thus enabling collagen fibrillation. Hydroxylated collagen has better thermostability compared to non-hydroxylated collagen and is resistant to high concentration pepsin digestion, for example at a pepsin:total protein ratio of 1:25 to 1:1. Therefore, to avoid premature proteolysis of recombinant collagen it is useful to provide hydroxylated collagen.

Alternative expression systems. Collagen and other proteins can be expressed in other kinds of yeast cells besides *Pichia pastoris*, for example, in may be expressed in another yeast, methylotrophic yeast or other organism. *Saccharomyces cerevisiae* can be used with any of a large number of expression vectors. Commonly employed expression vectors are shuttle vectors containing the 2P origin of replication for propagation in yeast and the Col E1 origin for *E. coli*, for efficient transcription of the foreign gene. A typical example of such vectors based on 2P plasmids is pWYG4, which has the 2P ORI-STB elements, the GAL1-10 promoter, and the 2P D gene terminator. In this vector, an NcoI cloning site is used to insert the gene for the polypeptide to be expressed and to provide an ATG start codon. Another expression vector is pWYG7L, which has intact 2αORI, STB, REP1 and REP2, and the GAL1-10 promoter, and uses the FLP terminator. In this vector, the encoding polynucleotide is inserted in the polylinker with its 5' ends at a BamHI or NcoI site. The vector containing the inserted polynucleotide is transformed into *S. cerevisiae* either after removal of the cell wall to produce spheroplasts that take up DNA on treatment with calcium and polyethylene glycol or by treatment of intact cells with lithium ions.

Alternatively, DNA can be introduced by electroporation. Transformants can be selected, for example, using host yeast cells that are auxotrophic for leucine, tryptophan, uracil, or histidine together with selectable marker genes such as LEU2, TRP1, URA3, HIS3, or LEU2-D.

There are a number of methanol responsive genes in methylotrophic yeasts such as *Pichia pastoris*, the expression of each being controlled by methanol responsive regulatory regions, also referred to as promoters. Any of such methanol responsive promoters are suitable for use in the practice of the present invention. Examples of specific regulatory regions include the AOX1 promoter, the AOX2 promoter, the dihydroxyacetone synthase (DAS), the P40 promoter, and the promoter for the catalase gene from *P. pastoris*, etc.

The methylotrophic yeast *Hansenula polymorpha* is also mentioned. Growth on methanol results in the induction of key enzymes of the methanol metabolism, such as MOX (methanol oxidase), DAS (dihydroxyacetone synthase), and FMHD (formate dehydrogenase). These enzymes can constitute up to 30-40% of the total cell protein. The genes encoding MOX, DAS, and FMDH production are controlled by strong promoters induced by growth on methanol and repressed by growth on glucose. Any or all three of these promoters may be used to obtain high-level expression of heterologous genes in *H. polymorpha*. Therefore, in one aspect, a polynucleotide encoding animal collagen or fragments or variants thereof is cloned into an expression vector under the control of an inducible *H. polymorpha* promoter. If secretion of the product is desired, a polynucleotide encoding a signal sequence for secretion in yeast is fused in frame with the polynucleotide. In a further embodiment, the expression vector preferably contains an auxotrophic marker gene, such as URA3 or LEU2, which may be used to complement the deficiency of an auxotrophic host.

The expression vector is then used to transform *H. polymorpha* host cells using techniques known to those of skill in the art. A useful feature of *H. polymorpha* transformation is the spontaneous integration of up to 100 copies of the expression vector into the genome. In most cases, the integrated polynucleotide forms multimers exhibiting a head-to-tail arrangement. The integrated foreign polynucleotide has been shown to be mitotically stable in several recombinant strains, even under non-selective conditions. This phenomena of high copy integration further ads to the high productivity potential of the system.

Foreign DNA is inserted into the yeast genome or maintained episomally to produce collagen. The DNA sequence for the collagen is introduced into the yeast via a vector. Foreign DNAs are any non-yeast host DNA and include for example, but not limited to, mammalian, *Caenorhabditis elegans* and bacteria. Suitable mammalian DNA for collagen production in yeast include, but is not limited to, bovine, porcine, kangaroo, alligator, crocodile, elephant, giraffe, zebra, llama, alpaca, lamb, dinosaur and combinations thereof.

The DNA for enabling the production of ascorbate can also be inserted on a single or multiple vectors. For a plant pathway the DNA for the genes GDP-L-Gal phosphorylase, Inositol-phosphate phosphatase, GDP-Mannose-3,5-epimerase are inserted via a vector into the yeast cell. *Pichia* is already known to contain the remaining genes in the pathway for producing ascorbate from glucose transformed via a vector into the yeast cell.

The DNA for the ascorbic pathway may be inserted by itself or combined with DNA for proteins. The ascorbic pathway enables the production of healthy yeast strains that are suitable for producing most proteins.

The DNA for enabling the production of the α ketoglutarate transporter can also be inserted on a single vector. The yeast optimized kgtP gene is transformed via a vector into the yeast cell.

The DNA for the α ketoglutarate transporter may be inserted by itself or combined with DNA for proteins or carbohydrates. The α ketoglutarate transporter enables healthy, fast growing yeast strains that are suitable for producing most proteins and carbohydrates. The transporter also enables increased production of hydroxylated collagen.

DNA can be inserted into a vector. Vectors useful for expressing proteins in yeasts are known, see Ausubel et al., supra, Vol. 2, Chapter 13; Grant et al. (1987) Expression and Secretion Vectors for Yeast, in Methods in Enzymology, Ed. Wu & Grossman, Acad. Press, N.Y. 153:516-544; Glover (1986) DNA Cloning, Vol. II, IRL Press, Wash., D.C., Ch. 3; Bitter (1987) Heterologous Gene Expression in Yeast, in Methods in Enzymology, Eds. Berger & Kimmel, Acad. Press, N.Y. 152:673-684; and The Molecular Biology of the Yeast *Saccharomyces*, Eds. Strathern et al., Cold Spring Harbor Press, Vols. I and II (1982), the disclosures of which are hereby incorporated by reference. Other suitable vectors include, but are not limited to, pHTX1-BiDi-P4HA-Pre-P4HB hygro, pHTX1-BiDi-P4HA-PHO1-P4HB hygro, pGCW14-pGAP1-BiDi-P4HA-Prepro-P4HB G418, pGCW14-pGAP1-BiDi-P4HA-PHO1-P4HB Hygro, pDF-Col3A1 modified Zeocin, pCAT-Col3A1 modified Zeocin, pDF-Col3A1 modified Zeocin with AOX1 landing pad, pHTX1-BiDi-P4HA-Pre-Pro-P4HB hygro. The vectors typically included at least one restriction site for linearization of DNA.

A select promoter may improve the production of a recombinant protein and may be included in a vector comprising sequences encoding the protein of interest (e.g., collagen) or hydroxylases. Suitable promoters for use in the present invention include, but are not limited to, AOX1 methanol induced promoter, pDF de-repressed promoter, pCAT de-repressed promoter, Das1-Das2 methanol induced bi-directional promoter, pHTX1 constitutive Bi-directional promoter, pGCW14-pGAP1 constitutive Bi-directional promoter and combinations thereof. Suitable methanol induced promoters include but are not limited to AOX2, Das 1, Das 2, pDF, pCAT, pPMP20, pFDH1, pFLD1, pTAL2, pFBA2, pPEX5, pDAK1, pFGH1, pRKI1, pREP2 and combinations thereof.

In accordance with the foregoing, it is also envisioned that a vector can be engineered to be an all-in-one vector which contains each of the genes selected from at least one of, including any combination or sub-combination of the same or the entirety of all, collagen, hydroxylase(s), α ketoglutarate transporter, and/or gene(s) necessary to complete a functioning ascorbate synthesis pathway.

In the vectors according to the invention, including the all-in-one vector, a terminator may be placed at the end of each open reading frame utilized in the vectors incorporated into the yeast. The DNA sequence for the terminator is inserted into the vector. For replicating vectors, an origin of replication is necessary to initiate replication. The DNA sequence for the origin of replication is inserted into the vector. One or more DNA sequences containing homology to the yeast genome may be incorporated into the vector to facilitate recombination and incorporation into the yeast genome or to stabilize the vector once transformed into the yeast cell.

A vector according to the invention will also generally include at least one selective marker that is used to select yeast cells that have been successfully transformed. The markers sometimes are related to antibiotic resistance and markers may also be related to the ability to grow with or without certain amino acids (auxotrophic markers). Suitable auxotrophic markers included, but are not limited to ADE, HIS, URA, LEU, LYS, TRP and combinations thereof. To provide for selection of yeast cells containing a recombinant vector, at least one DNA sequence for a selection marker is incorporated into the vector.

In some embodiments of the invention, amino acid residues, such as lysine and proline, in a recombinant yeast-expressed protein, including collagen or collagen-like protein, may lack hydroxylation or may have a lesser or greater degree of hydroxylation than a corresponding natural or unmodified protein, e.g., collagen or collagen-like protein. In other embodiments, amino acid residues in a recombinant yeast-expressed protein, including collagen or collagen-like protein, may lack glycosylation or may have a lesser or greater degree of glycosylation than a corresponding natural or unmodified protein, e.g., collagen or collagen-like protein.

Hydroxylated collagen, for example, has a higher melting temperature (>37° C.) than under hydroxylated collagen (<32° C.) and also fibrillates better than under hydroxylated collagen and form stronger structure for material purpose. The melting temperature of a collagen preparation may be used to estimate its degree of hydroxylation and can range, for example, from 25 to 40° C., as well as all intermediate values such as 25, 26, 27, 28, 29, 30, 31, 32, 33, 34, 35, 36, 37, 38, 39, and 40° C., as well as subranges that are bound on the lower and upper end by a temperature selected from the forgoing values can be used to select a population of collagen for use.

Under hydroxylated collagen may only form a jello-like material not suitable for durable items such as shoes or bags but which can be formulated into softer or more absorbent products. By increasing the degree of hydroxylation, it is possible to improve thermal stability of collagen and may also improve strength of the biofabricated material produced from the same. These biofabricated materials may be more suitable for items requiring greater durability including shoes, bags, seats, etc. As a means to modulate the degree of hydroxylation it is envisioned that the number of copies or expression of the respective enzymes may be increased, also envisioned is modification of the temperature, pH, and carbon source of cell culture.

The engineered yeast cells described above can be utilized as hosts to produce collagen or other proteins or carbohydrates. In order to do so, the cells are placed in media within a fermentation chamber and fed dissolved oxygen and a source of carbon, under controlled pH conditions for a period of time ranging from twelve hours to 1 week. Suitable media include but are not limited to buffered glycerol complex media (BMGY), buffered methanol complex media (BMMY), and yeast extract peptone dextrose (YPD). Due to the fact that protein is produced in the yeast cell and using collagen as an example, in order to isolate the collagen, one must either use a secretory strain of yeast or lyse the yeast cells to release the collagen. The collagen may then be purified through conventional techniques such as centrifugation, precipitation, filtration, chromatography, and the like.

EXAMPLES

The following non-limiting Examples are illustrative of the present invention. The scope of the invention is not limited to the details described in these Examples.

Example 1

Modification of yeast to enable a functional plant synthesis pathway for ascorbate. *Pichia pastoris* strain BG10 (wild type) was obtained from ATUM (formerly DNA 2.0). A vector containing DNA sequences of GDP-L-Gal phosphorylase (SEQ ID NO: 19), Inositol-phosphate phosphatase (SEQ ID NO: 20) and GDP-Mannose-3,5-epimerase (SEQ ID NO: 18) was inserted into wild type *Pichia pastoris* to generate a modified strain. The DNA was digested by Pme I and transformed into PP1 (Wild Type *Pichia pastoris* strain). This was suitable as a host strain.

Example 2

The host strain from example 1 is modified as described below: DNA encoding native Type III bovine collagen is sequenced and the sequence is amplified by polymerase chain reaction "PCR" protocol to create a linear DNA sequence.

DNA encoding P4HA/B enzymes is sequenced (SEQ ID NO: 8 and SEQ ID NO: 9) and the sequence is amplified by polymerase chain reaction "PCR" protocol to create a linear DNA sequence.

The DNA is transformed into the strain from example 1 using a *Pichia* Electroporation Protocol (Bio-Rad Gene Pulser XCELL™ Total System #1652660). Yeast cells are transformed with P4HA/B co-expression plasmid and transformants selected on Hygro plate (200 ug/ml).

A single colony of the resulting strain from example 1 is inoculated in 100 ml YPD medium and grown at 30 degrees overnight with shaking at 215 rpm. The next day when the culture reaches an OD600~3.5 (~3-5×10$^7$ cells/OD600) it is diluted with fresh YPD to OD600~1.7 and grown for another hour at 30 degree with shaking at 215 rpm.

Cells are spun down at 3,500 g for 5 min; washed once with water and resuspend in 10 ml 10 mM Tris-HCl (pH 7.5), 100 mM LiAc, 10 mM DTT (added fresh), and 0.6 M Sorbitol.

For each transformation, 8×10$^8$ cells are aliquoted into 8 ml 10 mM Tris-HCl (pH 7.5), 100 mM LiAc, 10 mM DTT, 0.6 M Sorbitol and allowed to incubate at room temperature for 30 min.

Cells are spun down at 5000 g for 5 mins and washed with ice cold 1.5 ml 1M Sorbitol 3 times and resuspend in 80 ul ice cold 1M Sorbitol.

Various amounts (about 5 ug) of linearized DNA are added to the cells and mixed by pipetting.

Cells and DNA mixture (80-100 ul) are added into a 0.2 cm electroporation cuvette and pulsed using *Pichia*—protocol (1500 v, 25 uF, 200Ω).

The cells are immediately transferred into 1 ml mixture of YPD and 1M Sorbitol (1:1) and incubated at 30 degree for >2 hour.

These cells are plated at different densities and incubated at 30° C. for 2 days.

Single colonies that appeared on the plate after two days are inoculated into 2 mL BMGY media in a 24 deep well plate and grown out for at least 48 hours at 30 degree Celsius with shaking at 900 rpm. The resulting cells are tested for collagen using cell lysis, SDS-page and pepsin assay following the procedure below.

Yeast cells are lysed in 1× lysis buffer using a Qiagen Tissue Lyser at a speed of 30 Hz continuously for 14 mins. Lysis buffer is made from 2.5 ml 1 M HEPES (final concentration 50 mM); 438.3 mg NaCl; final concentration 150 mM; 5 ml Glycerol; final concentration 10%; 0.5 ml TRITON™ X-100; final concentration 1%; and 42 ml Millipure water.

The lysed cells are centrifuged at 2,500 rpm at 4° C. for 15 mins on a tabletop centrifuge. The supernatant is retained and pellet discarded.

SDS-PAGE in the presence of 2-mercaptoethanol is performed on the supernatant, molecular weight markers, negative control and positive control. After electrophoresis the gel is removed and stained with Commassie Blue and then destained in water.

A pepsin assay is performed with the following procedure:

Before pepsin treatment perform BCA assay to obtain the total protein of each sample per Thermo Scientific protocol. Normalize the total protein to the lowest concentration for all samples. (Note: if lowest total protein concentration is less than 0.5 mg/mL do not use that concentration for normalization).

Put 100 uL of lysate in a microcentrifuge tube. Create a master mix containing the following: 37% HCl (0.6 μL of acid per 100 μL) and pepsin (stock is 1 mg/mL in deionized water, and final addition of pepsin should be at a 1:25 ratio pepsin:total protein (weight:weight). After addition of pepsin, mix 3× with pipet and allow the samples to incubate for an hour at room temperature for the pepsin reaction to take place. After an hour, add 1:1 volume of LDS loading buffer containing β-mercaptoethanol to each sample and allow to incubate for 7 minutes at 70° C. (In this situation 100 uL of LDS should be added). Then spin at 14,000 rpm for 1 minute to remove the turbidity.

Add 18 uL from the top of sample onto 3-8% TAE buffer and run gel for 1 hr 10 minutes at 150V.

Example 3

Yeast Producing Ascorbate

Cells from Example 1 are inoculated into glucose containing medium and grown at 30 degrees C. with shaking. Samples are collected at different time points (for example 24, 48, 72, etc hours) and analyzed for ascorbic acid for both intracellular and extracellular by using a commercially available kit. The amount of ascorbic acid is constant over time.

Example 4

Yeast Producing Ascorbate and Hydroxylated Collagen

Cells from Example 2 are inoculated into glucose containing medium and grown at 30 degrees C. with shaking. Samples are collected at different time points (for example 24, 48, 72, etc hours) and analyzed for ascorbic acid for both intracellular and extracellular by using a commercially available kit. Collagen expression level and hydroxylation are also analyzed by known methods.

Example 5

Modification of yeast to include an α ketoglutarate transporter. *Pichia pastoris* strain (wild type) was obtained from ATUM (formerly DNA 2.0).

A vector containing DNA sequences of kgtP (SEQ ID NO: 3) was inserted into wild type *Pichia pastoris* to generate a modified strain. The DNA was digested by Bam HI and transformed into PP1 (Wild Type *Pichia pastoris* strain). This is suitable as a host strain.

The kgtP gene was tagged with HA tag. The recombinant gene was detected by Western Blot using anti HA antibody. The band shown on the blot had the expected molecular weight for the kgtP gene.

Example 6

Modification of yeast to express α ketoglutarate transporter and to produce hydroxylated collagen.

The host strain from example 5 is modified as described below:

DNA encoding native Type III bovine collagen is sequenced (SEQ ID NO: 10) and the sequence is amplified by polymerase chain reaction "PCR" protocol to create a linear DNA sequence.

DNA encoding P4HA/B enzymes is sequenced (SEQ ID NO: 8 and 9 (*Pichia* optimized) or SEQ ID NO: 15 and 16 (native)) and the sequence is amplified by polymerase chain reaction "PCR" protocol to create a linear DNA sequence.

The linear DNA containing the collagen sequence is inserted into a *Pichia* genome and the linear DNA containing the P4HA/B sequences are inserted into the *Pichia* genome.

The DNA is transformed into the strain from example 5 using a *Pichia* Electroporation Protocol (Bio-Rad Gene Pulser XCELL' Total System #1652660). Yeast cells are transformed with P4HA/B co-expression plasmid and transformants selected on Hygro plate (200 µg/ml).

A single colony of the resulting strain from example 1 is inoculated in 100 ml YPD medium and grown at 30 degrees overnight with shaking at 215 rpm. The next day when the culture reaches an OD600~3.5 (~3-5×10$^7$ cells/OD600) it is diluted with fresh YPD to OD600~1.7 and grown for another hour at 30 degree with shaking at 215 rpm.

Spin down the cells at 3,500 g for 5 min; wash once with water and resuspend in 10 ml 10 mM Tris-HCl (pH 7.5), 100 mM LiAc, 10 mM DTT (add fresh), 0.6 M Sorbitol For each transformation, aliquot 8×10$^8$ cells into 8 ml 10 mM Tris-HCl (pH 7.5), 100 mM LiAc, 10 mM DTT, 0.6 M Sorbitol and incubate at room temperature for 30 min.

Spin down the cells at 5000 g for 5 mins and wash with ice cold 1.5 ml 1M Sorbitol 3 times and resuspend in 80 µl ice cold 1M Sorbitol Add various amount (about 5 µg) of linearized DNA to the cells and mix by pipetting.

Add cells and DNA mixture (80-100 µl) into 0.2 cm cuvette and pulse using *Pichia*—protocol (1500 v, 25 uF, 200Ω)

Immediately transfer the cells into 1 ml mixture of YPD and 1M Sorbitol (1:1) and incubate at 30 degree for >2 hour Plate the cells at different densities.

Inoculate single colonies into 2 mL BMGY media in a 24 deep well plate and grew out for at least 48 hours at 30 degree Celsius with shaking at 900 rpm. The resulting cells are tested for collagen using cell lysis, SDS-page and pepsin assay following the procedure below.

Yeast cells are lysed in 1× lysis buffer using a Qiagen TissueLyser at a speed of 30 Hz continuously for 14 mins. Lysis buffer was made from 2.5 ml 1 M HEPES (final concentration 50 mM); 438.3 mg NaCl; final concentration 150 mM; 5 ml Glycerol; final concentration 10%; 0.5 ml TRITON™ X-100; final concentration 1%; and 42 ml Millipure water.

The lysed cells are centrifuged at 2,500 rpm at 4° C. for 15 mins on a tabletop centrifuge. The supernatant is retained and pellet discarded.

SDS-PAGE in the presence of 2-mercaptoethanol is performed on the supernatant, molecular weight markers, negative control and positive control. After electrophoresis the gel is removed and stained with Commassie Blue and then destained in water.

A pepsin assay is performed with the following procedure:

Before pepsin treatment perform BCA assay to obtain the total protein of each sample per Thermo Scientific protocol. Normalize the total protein to the lowest concentration for all samples. (Note: if lowest total protein concentration is less than 0.5 mg/mL do not use that concentration for normalization)

Put 100 µL of lysate in a microcentrifuge tube. Create a master mix containing the following: 37% HC 1 (0.6 µL of acid per 100 µL) and pepsin (stock is 1 mg/mL in deionized water, and final addition of pepsin should be at a 1:25 ratio pepsin:total protein (weight:weight). After addition of pepsin, mix 3× with pipet and allow the samples to incubate for an hour at room temperature for the pepsin reaction to take place. After an hour, add 1:1 volume of LDS loading buffer containing β-mercaptoethanol to each sample and allow to incubate for 7 minutes at 70° C. (In this situation 100 µL of LDS should be added). Then spin at 14,000 rpm for 1 minute to remove the turbidity.

Add 18 µL from the top of sample onto a 3-8% TAE and run gel for 1 hr 10 minutes at 150V. Amino acid analysis was performed to determine the percentage of hydroxylation. Expression of kgtP enables transport of alpha ketoglutarate into the endoplasmic reticulum which results in increased collagen and hydroxylated collagen level.

Example 7

The yeast from Example 1 with the ascorbate pathway are modified with procedure of Example 5 to transform the transporter into the yeast providing *Pichia* with both the ascorbate pathway and the kgtP transporter.

Example 8

The yeast from Example 7 with the ascorbate pathway and the transporter for kgtP are modified with the procedure of Example 2 to provide *Pichia* with the ascorbate pathway, the transporter for kgtP and hydroxylated collagen.

Example 9

The gene for L-gulono-1,4-lactone oxidase (purchased from Eurofins Genomics) was codon optimized for expression in *Pichia* (SEQ ID NO 17). The gene was cloned under the constitutive promoter pDF and the antibiotic marker used was zeocin. The plasmid was transformed into *Pichia* cells using the same electroporation method as in Example 2 and plated on YPD plates with 50 μg/ml of zeocin. The plates were incubated at 30° C. for 2 days or until the transformants started to appear on the plate.

Six transformants from the plate were picked and grown in 2 ml of BMGY media in 24 well plates for 18 hours with constant shaking at 30° C. After 18 hours, varied concentration of the substrate (L-gulono-1,4-lactone) was added to the growing culture (0, 0.1 and 1 g/L final concentration). Wild type *Pichia* cells were used as a control for the experiment and the substrate was also added to the control culture. The cultures were harvested after 20 hours after the addition of the substrate. The optical density was normalized and the cells were lysed in water by mechanical shearing. Two methods were used to quantify ascorbic acid concentration in the cell lysate. In the first method, an abcam kit (Cat #ab65356) was used, where fluorescence intensity of the reaction mix was measured. The second method is known as the Sullivan and Clarke method, where absorbance for different cell lysate samples was recorded as the measure of the ascorbic acid production. Cells lysates of the transformants having L-gulono-1,4-lactone oxidase gene showed higher fluorescence intensity and higher absorbance than the controls (wild type *Pichia* and Transformants grown without the substrate). Preliminary data indicated that ascorbic acid was made when 1 g/L of the substrate was added to the cells and ~10 nmol of ascorbic acid was produced at later time points (36 hours post addition of the substrate).

---

We claim:

1. A recombinant yeast cell, comprising an exogenous polynucleotide that encodes GDP-L-Gal phosphorylase,
   wherein the recombinant yeast cell is *Pichia pastoris*,
   wherein the recombinant yeast cell further comprises a polynucleotide encoding bovine collagen, and
   wherein the exogenous polynucleotide is SEQ ID NO: 18 and the polynucleotide encoding bovine collagen is SEQ ID NO: 11.

2. The recombinant yeast cell of claim 1, wherein the exogenous polynucleotide is recombined into the genome of the yeast cell.

3. The recombinant yeast cell of claim 1, wherein the collagen is hydroxylated on at least one proline or lysine residue.

4. The recombinant yeast cell of claim 1, further comprising at least one polynucleotide encoding an enzyme selected from the group consisting of prolyl-4-hydroxylase, prolyl 3-hydroxylase, and lysyl hydroxylase.

5. The recombinant yeast cell of claim 1, wherein the collagen is glycosylated on at least one hydroxylysyl residue.

6. A method for producing the recombinant yeast cell of claim 1, the method comprising transforming the yeast cell with the exogenous polynucleotide which is operably linked to one or more transcriptional control elements that enable the production of mRNA encoding an exogenous polypeptide in the yeast cell.

7. The recombinant yeast cell of claim 1, wherein the recombinant yeast cell further comprises a polynucleotide encoding an α-ketoglutarate transporter.

8. The method of claim 6, wherein the method further comprises transforming the yeast cell with a polynucleotide encoding an α-ketoglutarate transporter.

* * * * *

SEQUENCE LISTING

```
<160> NUMBER OF SEQ ID NOS: 30

<210> SEQ ID NO 1
<211> LENGTH: 432
<212> TYPE: PRT
<213> ORGANISM: Artificial Sequence
<220> FEATURE:
<223> OTHER INFORMATION: Synthetic peptide: kgtP gene, AKG transporter
      from E. coli

<400> SEQUENCE: 1

Met Ala Glu Ser Thr Val Thr Ala Asp Ser Lys Leu Thr Ser Ser Asp
1               5                   10                  15

Thr Arg Arg Arg Ile Trp Ala Ile Val Gly Ala Ser Ser Gly Asn Leu
            20                  25                  30

Val Glu Trp Phe Asp Phe Tyr Val Tyr Ser Phe Cys Ser Leu Tyr Phe
        35                  40                  45

Ala His Ile Phe Phe Pro Ser Gly Asn Thr Thr Thr Gln Leu Leu Gln
    50                  55                  60

Thr Ala Gly Val Phe Ala Ala Gly Phe Leu Met Arg Pro Ile Gly Gly
65                  70                  75                  80

Trp Leu Phe Gly Arg Ile Ala Asp Lys His Gly Arg Lys Lys Ser Met
                85                  90                  95

Leu Leu Ser Val Cys Met Met Cys Phe Gly Ser Leu Val Ile Ala Cys
            100                 105                 110

Leu Pro Gly Tyr Glu Thr Ile Gly Thr Trp Ala Pro Ala Leu Leu Leu
        115                 120                 125

Leu Ala Arg Leu Phe Gln Gly Leu Ser Val Gly Gly Glu Tyr Gly Thr
    130                 135                 140

Ser Ala Thr Tyr Met Ser Glu Val Ala Val Glu Gly Arg Lys Gly Phe
145                 150                 155                 160

Tyr Ala Ser Phe Gln Tyr Val Thr Leu Ile Gly Gly Gln Leu Leu Ala
```

```
                165                 170                 175
Leu Leu Val Val Val Leu Gln His Thr Met Glu Asp Ala Ala Leu
            180                 185                 190

Arg Glu Trp Gly Trp Arg Ile Pro Phe Ala Leu Gly Ala Val Leu Ala
        195                 200                 205

Val Val Ala Leu Trp Leu Arg Arg Gln Leu Asp Glu Thr Ser Gln Gln
    210                 215                 220

Glu Thr Arg Ala Leu Lys Glu Ala Gly Ser Leu Lys Gly Leu Trp Arg
225                 230                 235                 240

Asn Arg Arg Ala Phe Ile Met Val Leu Gly Phe Thr Ala Ala Gly Ser
                245                 250                 255

Leu Cys Phe Tyr Thr Phe Thr Thr Tyr Met Gln Lys Tyr Leu Val Asn
            260                 265                 270

Thr Ala Gly Met His Ala Asn Val Ala Ser Gly Ile Met Thr Ala Ala
        275                 280                 285

Leu Phe Val Phe Met Leu Ile Gln Pro Leu Ile Gly Ala Leu Ser Asp
    290                 295                 300

Lys Ile Gly Arg Arg Thr Ser Met Leu Cys Phe Gly Ser Leu Ala Ala
305                 310                 315                 320

Ile Phe Thr Val Pro Ile Leu Ser Ala Leu Gln Asn Val Ser Ser Pro
                325                 330                 335

Tyr Ala Ala Phe Gly Leu Val Met Cys Ala Leu Leu Ile Val Ser Phe
            340                 345                 350

Tyr Thr Ser Ile Ser Gly Ile Leu Lys Ala Glu Met Phe Pro Ala Gln
        355                 360                 365

Val Arg Ala Leu Gly Val Gly Leu Ser Tyr Ala Val Ala Asn Ala Ile
    370                 375                 380

Phe Gly Gly Ser Ala Glu Tyr Val Ala Leu Ser Leu Lys Ser Ile Gly
385                 390                 395                 400

Met Glu Thr Ala Phe Phe Trp Tyr Val Thr Leu Met Ala Val Val Ala
                405                 410                 415

Phe Leu Val Ser Leu Met Leu His Arg Lys Gly Lys Gly Met Arg Leu
            420                 425                 430

<210> SEQ ID NO 2
<211> LENGTH: 1299
<212> TYPE: DNA
<213> ORGANISM: Artificial Sequence
<220> FEATURE:
<223> OTHER INFORMATION: Synthetic nucleotide: kgtP gene, AKG
      transporter from E. coli, native (unoptimized)

<400> SEQUENCE: 2
atggctgaaa gtactgtaac ggcagacagc aaactgacaa gtagtgatac tcgtcgccgc      60
atttgggcga ttgtgggggc ctcttcaggt aatctggtcg agtggttcga tttctatgtc     120
tactcgttct gttcactcta ctttgcccac atcttcttcc cttccgggaa cacgacgact     180
caactactac aaacagcagg tgttttttgct gcgggattcc tgatgcgccc aataggcggt     240
tggctatttg ccgcatagc cgataaacat ggtcgcaaaa aatcgatgct gttatcggtg     300
tgtatgatgt gtttcggatc gctggttatc gcctgcctcc caggttatga aactataggt     360
acgtgggctc cggcattatt gcttctcgct cgtttatttc agggattatc tgttggcgga     420
gaatatggca ccagcgccac ctatatgagt gaagttgccg ttgaagggcg caaaggtttt     480
tacgcatcat ttcagtatgt gacgttgatc ggcggacaac tgctagccct actggttgtc     540
```

| | |
|---|---|
| gtggttttac aacacaccat ggaagacgct gcactcagag agtggggatg gcgtattcct | 600 |
| ttcgcgttag gagctgtgtt agctgttgtg gcgttgtggt tacgtcgtca gttagatgaa | 660 |
| acttcgcaac aagaaacgcg cgctttaaaa gaagctggat ctctgaaagg attatggcgc | 720 |
| aatcgccgtg cattcatcat ggttctcggt tttaccgctg cgggctccct ttgtttctat | 780 |
| accttcacta cttatatgca gaagtatctg gtaaatactg cgggaatgca tgccaacgtg | 840 |
| gcgagtggca ttatgactgc cgcattgttt gtattcatgc ttattcaacc actcattggc | 900 |
| gcgctgtcgg ataagattgg tcgccgtacc tcaatgttat gtttcggttc gctggcagcc | 960 |
| attttttaccg ttcctattct ctcagcattg caaaacgttt cctcgcctta tgccgctttt | 1020 |
| ggtctggtga tgtgtgccct gctgatagtg agttttttata catcaatcag tggaatactg | 1080 |
| aaggctgaga tgttcccggc acaggttcgc gcattaggcg ttggtctgtc atatgcggtc | 1140 |
| gctaatgcta tatttggtgg ttcggcggag tacgtagcgt tgtcgctgaa atcaatagga | 1200 |
| atggaaacag ccttcttctg gtatgtgacc ttgatggccg tggtggcgtt tctggttttct | 1260 |
| ttgatgctac atcgcaaagg gaagggggatg cgtctttag | 1299 |

<210> SEQ ID NO 3
<211> LENGTH: 1299
<212> TYPE: DNA
<213> ORGANISM: Artificial Sequence
<220> FEATURE:
<223> OTHER INFORMATION: Synthetic nucleotide: kgtP gene, AKG
      transporter from E. coli, codon optimized for Pichia

<400> SEQUENCE: 3

| | |
|---|---|
| atggcagaat caactgtgac ggcagacagt aagctgacct catcagatac tagaaggaga | 60 |
| atctgggcaa tagttggagc ctcttccgga aatcttgtag agtggtttga cttttatgtt | 120 |
| tattcattct gcagtctgta ttttgcacat attttctttc catctggcaa caccaccaca | 180 |
| caactgttac agaccgccgg cgtgttcgct gccggatttc ttatgaggcc cattggtgga | 240 |
| tggttgtttg gtagaatagc tgacaagcat ggtcgtaaga agtctatgtt gttgtctgtc | 300 |
| tgtatgatgt gcttcggatc actggtaatt gcatgtcttc caggttacga gaccattgga | 360 |
| acatgggctc ccgctttgct tctacttgcc aggctatttc agggtttatc agtcggtggc | 420 |
| gaatacggca cttctgcaac gtacatgtct gaggtagcag tcgagggtag aaaaggattc | 480 |
| tacgcctcct tcaatacgt tacactgata ggaggtcaac ttcttgcctt gctagtggtc | 540 |
| gttgtcctac aacacacgat ggaggacgct gctctgaggg aatggggatg gcgtataccc | 600 |
| ttcgctttag gtgccgtcct ggccgttgtc gcattgtggt tgaggaggca gctagatgaa | 660 |
| acttcccagc aagagacaag agcattgaaa gaggccggtt cacttaaagg tctgtggcgt | 720 |
| aaccgtcgtg ccttttattat ggtgcttggc ttcacggctg ctggctccct ttgcttctat | 780 |
| actttcacca cttatatgca gaaatatttg gtgaatactg caggtatgca cgctaacgtc | 840 |
| gcttccggaa ttatgacggc tgcattgttt gtctttatgc taattcaacc attgataggc | 900 |
| gctctatctg ataagatagg ccgtaggact tcaatgctat gtttcggctc cttggctgca | 960 |
| attttttaccg tgcctattct atctgcccta caaaatgtgt cttctccata cgctgctttt | 1020 |
| ggtctggtaa tgtgcgcttt actaattgtg tcttttttaca cgtcaatttc cggaatacta | 1080 |
| aaagccgaga tgttcccgc ccaggtacgt gccttaggtg ttggcctttc ttacgcagtc | 1140 |
| gcaaacgcta ttttcggtgg aagtgccgag tatgtagctt tgtctcttaa aagtatcgga | 1200 |
| atggagacgg cctttttctg gtatgtaact ttgatggccg tcgttgcatt cctagtttcc | 1260 | cttatgttac acaggaaagg caaaggtatg aggttataa                                  1299

<210> SEQ ID NO 4
<211> LENGTH: 736
<212> TYPE: PRT
<213> ORGANISM: Artificial Sequence
<220> FEATURE:
<223> OTHER INFORMATION: Synthetic peptide: prolyl 3-hydroxylase 1
      precursor (Bos taurus), NCBI reference sequence NP_001096761.1

<400> SEQUENCE: 4

Met Ala Ala Arg Ala Leu Arg Leu Leu Thr Ile Leu Leu Ala Val Ala
1               5                   10                  15

Ala Thr Ala Ser Gln Ala Glu Ala Ser Glu Ala Gly Trp Asp Leu
            20                  25                  30

Thr Ala Pro Asp Leu Leu Phe Ala Glu Gly Thr Ala Ala Tyr Ala Arg
        35                  40                  45

Gly Asp Trp Ala Gly Val Val Leu Ser Met Glu Arg Ala Leu Arg Ser
    50                  55                  60

Arg Ala Ala Leu Arg Ala Leu Arg Leu Arg Cys Arg Thr Arg Cys Ala
65                  70                  75                  80

Ala Asp Leu Pro Trp Glu Val Asp Pro Asp Ser Pro Pro Ser Leu Ala
                85                  90                  95

Gln Ala Ser Gly Ala Ser Ala Leu His Asp Leu Arg Phe Phe Gly Gly
            100                 105                 110

Leu Leu Arg Arg Ala Ala Cys Leu Arg Arg Cys Leu Gly Pro Ser Thr
        115                 120                 125

Ala His Ser Leu Ser Glu Glu Leu Glu Leu Glu Phe Arg Lys Arg Ser
    130                 135                 140

Pro Tyr Asn Tyr Leu Gln Val Ala Tyr Phe Lys Ile Asn Lys Leu Glu
145                 150                 155                 160

Lys Ala Val Ala Ala Ala His Thr Phe Phe Val Gly Asn Pro Glu His
                165                 170                 175

Met Glu Met Arg Gln Asn Leu Asp Tyr Tyr Gln Thr Met Ser Gly Val
            180                 185                 190

Lys Glu Ala Asp Phe Lys Asp Leu Glu Ala Lys Pro His Met His Glu
        195                 200                 205

Phe Arg Leu Gly Val Arg Leu Tyr Ser Glu Glu Gln Pro Gln Glu Ala
    210                 215                 220

Val Pro His Leu Glu Ala Ala Leu Arg Glu Tyr Phe Val Ala Ala Glu
225                 230                 235                 240

Glu Cys Arg Ala Leu Cys Glu Gly Pro Tyr Asp Tyr Asp Gly Tyr Asn
                245                 250                 255

Tyr Leu Glu Tyr Asn Ala Asp Leu Phe Gln Ala Ile Thr Asp His Tyr
            260                 265                 270

Ile Gln Val Leu Ser Cys Lys Gln Asn Cys Val Thr Glu Leu Ala Ser
        275                 280                 285

His Pro Ser Arg Glu Lys Pro Phe Glu Asp Phe Leu Pro Ser His Tyr
    290                 295                 300

Asn Tyr Leu Gln Phe Ala Tyr Tyr Asn Ile Gly Asn Tyr Thr Gln Ala
305                 310                 315                 320

Ile Glu Cys Ala Lys Thr Tyr Leu Leu Phe Phe Pro Asn Asp Glu Val
                325                 330                 335

Met Ser Gln Asn Leu Ala Tyr Tyr Thr Ala Met Leu Gly Glu Glu Gln
            340                 345                 350

```
Ala Arg Ser Ile Gly Pro Arg Glu Ser Ala Gln Glu Tyr Arg Gln Arg
        355                 360                 365

Ser Leu Leu Glu Lys Glu Leu Leu Phe Phe Ala Tyr Asp Val Phe Gly
    370                 375                 380

Ile Pro Phe Val Asp Pro Asp Ser Trp Thr Pro Val Glu Val Ile Pro
385                 390                 395                 400

Lys Arg Leu Gln Glu Lys Gln Lys Ser Glu Arg Glu Thr Ala Ala Arg
                405                 410                 415

Ile Ser Gln Glu Ile Gly Asn Leu Met Lys Glu Ile Glu Thr Leu Val
                420                 425                 430

Glu Glu Lys Thr Lys Glu Ser Leu Asp Val Ser Arg Leu Thr Arg Glu
            435                 440                 445

Gly Gly Pro Leu Leu Tyr Asp Gly Ile Arg Leu Thr Met Asn Ser Lys
        450                 455                 460

Val Leu Asn Gly Ser Gln Arg Val Val Met Asp Gly Val Ile Ser Asp
465                 470                 475                 480

Glu Glu Cys Gln Glu Leu Gln Arg Leu Thr Asn Ala Ala Ala Thr Ser
                485                 490                 495

Gly Asp Gly Tyr Arg Gly Gln Thr Ser Pro His Thr Pro Ser Glu Lys
                500                 505                 510

Phe Tyr Gly Val Thr Val Phe Lys Ala Leu Lys Leu Gly Gln Glu Gly
            515                 520                 525

Lys Val Pro Leu Gln Ser Ala His Leu Tyr Tyr Asn Val Thr Glu Lys
        530                 535                 540

Val Arg Arg Val Met Glu Ser Tyr Phe Arg Leu Asp Thr Pro Leu Tyr
545                 550                 555                 560

Phe Ser Tyr Ser His Leu Val Cys Arg Thr Ala Ile Glu Glu Ala Gln
                565                 570                 575

Ala Glu Arg Lys Asp Gly Ser His Pro Val His Val Asp Asn Cys Ile
                580                 585                 590

Leu Asn Ala Glu Ala Leu Val Cys Ile Lys Glu Pro Pro Ala Tyr Thr
            595                 600                 605

Phe Arg Asp Phe Ser Ala Ile Leu Tyr Leu Asn Glu Asp Phe Asp Gly
        610                 615                 620

Gly Asn Phe Tyr Phe Thr Glu Leu Asp Ala Lys Thr Val Thr Ala Glu
625                 630                 635                 640

Val Gln Pro Gln Cys Gly Arg Ala Val Gly Phe Ser Ser Gly Thr Glu
                645                 650                 655

Asn Pro His Gly Val Lys Ala Val Thr Arg Gly Gln Arg Cys Ala Ile
                660                 665                 670

Ala Leu Trp Phe Thr Leu Asp Ala Arg His Ser Glu Arg Glu Arg Val
            675                 680                 685

Gln Ala Asp Asp Leu Val Lys Met Leu Phe Ser Pro Glu Glu Met Asp
        690                 695                 700

Leu Pro His Glu Gln Pro Gln Glu Ala Gln Glu Gly Thr Pro Glu Pro
705                 710                 715                 720

Leu Gln Glu Pro Val Ser Ser Ser Glu Ser Gly His Lys Asp Glu Leu
                725                 730                 735

<210> SEQ ID NO 5
<211> LENGTH: 2580
<212> TYPE: DNA
<213> ORGANISM: Artificial Sequence
<220> FEATURE:
<223> OTHER INFORMATION: Synthetic nucleotide: Bos taurus prolyl
```

3-hydroxylase 1 (P3H1), NCBI reference sequence NM_001103291.1

<400> SEQUENCE: 5

```
caagggtccc gttaggtctg agcggccatg gcggcacgcg ctttaaggct gctgaccata      60
ttgctggccg tcgccgccac tgcctcccag gctgaggccg agtccgaggc gggatgggac     120
ctgacggcgc ctgatctgct gttcgcggag gggacggcgg cctatgctcg cggggactgg     180
gccggtgtgg ttctgagcat ggagcgggcg ctccgctcgc gggccgccct gcgcgccctc     240
cgtctgcgct gccgcactcg gtgtgccgcc gacctcccat gggaagtgga cccagactcg     300
cccccaagct tggcgcaggc ttcaggtgcc tccgccctgc acgacctgcg gttcttcgga     360
ggcttgctgc gccgcgccgc ttgcctgcgc cgctgcctcg ggccgtcgac cgcccactcg     420
ctcagcgagg agctggagtt ggagttccgc aagcggagcc cctacaacta cctgcaggtc     480
gcctacttca agataaacaa gttggagaaa gctgtagcag cagcccatac cttcttcgtg     540
ggcaaccctg agcacatgga gatgcgacag aacctggact attaccagac catgtctggg     600
gtgaaggagg ctgacttcaa ggatcttgag gccaaacccc atatgcacga atttcggctg     660
ggagtgcgcc tctactccga ggagcagccg caggaagccg tgccccacct ggaggcggcg     720
ctgcgggagt acttcgtggc ggccgaggag tgccgcgcgc tctgcgaagg gccctatgac     780
tacgacggct acaactacct ggagtacaat gccgacctct tccaggccat cacagatcat     840
tacatccagg tcctcagctg taagcagaac tgtgtcacgg agcttgcttc ccacccaagt     900
cgagagaagc cctttgaaga cttcctgcca tctcattata attatctgca gtttgcctac     960
tataacattg gaattacaca caggccatt gaatgtgcca agacctatct cctcttcttt    1020
cccaatgatg aggtgatgag ccagaatctg gcctactata cagccatgct ggagaagag    1080
caagccagat ccattggccc ccgtgagagt gcccaggagt accgccagcg gagcctgctg    1140
gagaaggaac tgcttttctt cgcctatgac gttttttggaa ttcccttttgt tgatccggat    1200
tcatggactc cagtggaggt gattcctaag agactgcaag agaaacagaa gtcagaacgg    1260
gaaacagctg cccgcatctc ccaggaaatc gggaacctta tgaaggagat cgagaccctc    1320
gtggaggaga agaccaagga gtcactggac gtgagcaggc tgacccggga aggtggcccc    1380
ctgctgtatg atggcatcag actcaccatg aactccaaag tcctgaatgg ttcccagcgg    1440
gtggtgatgg atggcgtcat ctctgacgag gagtgccagg agctgcagag actgaccaat    1500
gcagcagcaa cttcaggaga tggctaccgg ggtcagacct ccccacacac ccccagcgag    1560
aagttctacg tgtcaccgt cttcaaggcc ctcaagctgg ggcaggaagg gaaggttcct    1620
ctgcagagcg cccacctgta ctacaacgtg acggagaagg tgcgccgcgt catggagtcg    1680
tacttccgcc tggatacccc gctctacttc tcctactccc acctggtgtg ccgcaccgcc    1740
atcgaagagg cacaggctga gaggaaggac ggtagccacc ccgtccacgt ggacaactgc    1800
atcctgaatg ccgaggccct cgtgtgcatc aaggagcccc ctgcctacac tttccgggac    1860
ttcagcgcca ttctttatct gaacgaagac ttcgatggag gaaacttta tttcactgaa    1920
ctagatgcca agaccgtgac ggcagaggtg cagccccagt gcggaagggc tgtgggattc    1980
tcttccggca cggaaaaccc gcatggagta aaggccgtca ccagagggca gcgctgtgcc    2040
attgccctct ggttcactt ggatgctcga cacagcgaga gggagcgagt gcaggcggac    2100
gacctggtaa agatgctctt tagcccagaa gagatggacc tccccacga gcagccccaa    2160
gaagcccagg aggggacccc cgagccccta caggagcccg tctccagcag tgagtcaggg    2220
cacaaggatg agctctgaca actcccgtgg atggtgatca gacccacacg agggactctg    2280
```

-continued

```
tcctgcagcc tggactggcc agccccgggc gaggagcagt gggaacccag gcctgccgcc    2340
cagctgaggg ggctctgctc acggccgtcc gcatggtgct gctgctcttg gagtggacat    2400
ggcgagatgg ccctctcccc tctgggcctg actgagggct caggacgcag gcccagagcc    2460
actctggggg cccacacagg cagccacgtg acagcaatac agtatttaag tgcctgtgta    2520
gacaaccaaa gaataaatga ttcgtggttt ttttaaaaa aaaaaaaaa aaaaaaaaa       2580
```

<210> SEQ ID NO 6
<211> LENGTH: 726
<212> TYPE: PRT
<213> ORGANISM: Artificial Sequence
<220> FEATURE:
<223> OTHER INFORMATION: Synthetic peptide: procollagen-lysine 2-oxoglutarate 5-dioxygenase 1 precursor, Bos taurus, NCBI reference sequence NP_776573.1

<400> SEQUENCE: 6

```
Met Arg Leu Leu Leu Leu Ala Pro Leu Gly Trp Leu Leu Ala
1               5                   10                  15

Glu Thr Lys Gly Asp Ala Lys Pro Glu Asp Asn Leu Leu Val Leu Thr
            20                  25                  30

Val Ala Thr Lys Glu Thr Glu Gly Phe Arg Arg Phe Lys Arg Ser Ala
        35                  40                  45

Gln Phe Phe Asn Tyr Lys Ile Gln Ala Leu Gly Leu Gly Glu Asp Trp
    50                  55                  60

Pro Gly Glu Ala Met Leu Ala Gly Gly Gly Leu Lys Val Arg Leu Leu
65                  70                  75                  80

Lys Lys Ala Leu Glu Lys His Ala Asp Lys Glu Asn Leu Val Ile Leu
                85                  90                  95

Phe Thr Asp Ser Tyr Asp Val Val Phe Ala Ser Gly Pro Arg Glu Leu
            100                 105                 110

Leu Lys Lys Phe Arg Gln Ala Arg Ser Gln Val Val Phe Ser Ala Glu
        115                 120                 125

Glu Leu Ile Tyr Pro Asp Arg Arg Leu Glu Ala Asn Tyr Pro Val Val
    130                 135                 140

Ser Asp Gly Lys Arg Phe Leu Gly Ser Gly Gly Phe Ile Gly Tyr Ala
145                 150                 155                 160

Pro Asn Leu Ile Lys Leu Val Ala Glu Trp Glu Gly Gln Asp Ser Asp
                165                 170                 175

Ser Asp Gln Leu Phe Tyr Thr Lys Ile Phe Leu Asp Pro Glu Lys Arg
            180                 185                 190

Glu Gln Ile Asn Ile Thr Leu Asp His Arg Cys Arg Ile Phe Gln Asn
        195                 200                 205

Phe His Gly Ala Leu Asp Glu Val Val Leu Lys Phe Glu Met Gly Gln
    210                 215                 220

Val Arg Ala Arg Asn Leu Ala Tyr Asp Thr Leu Pro Val Leu Ile His
225                 230                 235                 240

Gly Asn Gly Pro Thr Lys Leu Gln Leu Asn Tyr Leu Gly Asn Tyr Ile
                245                 250                 255

Pro Arg Phe Trp Thr Phe Glu Thr Gly Cys Ala Val Cys Asp Glu Gly
            260                 265                 270

Leu Arg Ser Leu Lys Gly Ile Gly Asp Glu Ala Leu Pro Ala Val Leu
        275                 280                 285

Val Gly Val Phe Ile Glu Gln Pro Thr Pro Phe Leu Ser Leu Phe Phe
    290                 295                 300
```

```
Gln Arg Leu Leu Leu His Tyr Pro Gln Lys Arg Phe Arg Leu Phe
305                 310                 315                 320

Ile His Asn His Glu Gln His His Lys Ala Gln Val Glu Gln Phe Leu
            325                 330                 335

Ala Glu His Gly Asp Glu Tyr Gln Ser Val Lys Leu Val Gly Pro Glu
            340                 345                 350

Val Arg Val Ala Asn Ala Asp Ala Arg Asn Met Gly Ala Asp Leu Cys
            355                 360                 365

Arg Gln Asp Arg Gly Cys Thr Tyr Tyr Phe Ser Val Asp Ala Asp Val
            370                 375                 380

Ala Leu Thr Glu Pro Lys Thr Leu Arg Leu Leu Ile Glu Gln Asn Lys
385                 390                 395                 400

Asn Val Ile Thr Pro Leu Met Thr Arg His Gly Arg Leu Trp Ser Asn
                405                 410                 415

Phe Trp Gly Ala Leu Ser Ala Asp Gly Tyr Tyr Ala Arg Ser Glu Asp
            420                 425                 430

Tyr Val Asp Ile Val Gln Gly Arg Val Gly Val Trp Asn Val Pro
            435                 440                 445

Tyr Ile Ser Asn Ile Tyr Leu Ile Lys Gly Ser Ala Leu Arg Ala Glu
450                 455                 460

Leu Gln Glu Thr Asp Leu Phe His His Ser Lys Leu Asp Pro Asp Met
465                 470                 475                 480

Ala Phe Cys Ala Asn Ile Arg Gln Gln Asp Val Phe Met Phe Leu Thr
            485                 490                 495

Asn Arg His Ser Phe Gly His Leu Leu Ser Leu Asp Ser Tyr Gln Thr
            500                 505                 510

Thr His Leu His Asn Asp Leu Trp Glu Val Phe Ser Asn Pro Glu Asp
        515                 520                 525

Trp Lys Glu Lys Tyr Ile His Glu Asn Tyr Thr Lys Ala Leu Ala Gly
    530                 535                 540

Lys Met Val Glu Met Pro Cys Pro Asp Val Tyr Trp Phe Pro Ile Phe
545                 550                 555                 560

Thr Glu Thr Ala Cys Asp Glu Leu Val Glu Met Glu His Tyr Gly
            565                 570                 575

Gln Trp Ser Leu Gly Asp Asn Lys Asp Asn Arg Ile Gln Gly Gly Tyr
            580                 585                 590

Glu Asn Val Pro Thr Ile Asp Ile His Met Asn Gln Ile Asn Tyr Glu
            595                 600                 605

Arg Glu Trp His Lys Phe Leu Val Glu Tyr Ile Ala Pro Met Thr Glu
            610                 615                 620

Lys Leu Tyr Pro Gly Tyr Tyr Thr Arg Ala Gln Phe Asp Leu Ala Phe
625                 630                 635                 640

Val Val Arg Tyr Lys Pro Asp Glu Gln Pro Ser Leu Val Pro His His
                645                 650                 655

Asp Ala Ser Thr Phe Thr Ile Asn Ile Gly Leu Asn Arg Val Gly Val
            660                 665                 670

Asp Tyr Glu Gly Gly Gly Cys Arg Phe Leu Arg Tyr Asn Cys Ser Ile
            675                 680                 685

Arg Ala Pro Arg Lys Gly Trp Thr Leu Met His Pro Gly Arg Leu Thr
            690                 695                 700

His Tyr His Glu Gly Val Pro Thr Thr Lys Gly Thr Arg Tyr Ile Ala
705                 710                 715                 720
```

```
Val Ser Phe Val Asp Pro
                725
```

<210> SEQ ID NO 7
<211> LENGTH: 418
<212> TYPE: PRT
<213> ORGANISM: Artificial Sequence
<220> FEATURE:
<223> OTHER INFORMATION: Synthetic peptide: lysyl oxidase, Bos taurus,
      GenBank AAL13313.1
<220> FEATURE:
<221> NAME/KEY: misc_feature
<222> LOCATION: (253)..(253)
<223> OTHER INFORMATION: Xaa can be any naturally occurring amino acid

<400> SEQUENCE: 7

```
Met Arg Phe Ala Trp Thr Ala Leu Leu Gly Ser Leu Gln Leu Cys Ala
1               5                   10                  15

Leu Val Arg Cys Ala Pro Pro Ala Ala Ser His Arg Gln Pro Pro Arg
                20                  25                  30

Glu Gln Ala Ala Ala Pro Gly Ala Trp Arg Gln Lys Ile Gln Trp Glu
            35                  40                  45

Asn Asn Gly Gln Val Phe Ser Leu Leu Ser Leu Gly Ser Gln Tyr Gln
50                  55                  60

Pro Gln Arg Arg Arg Asp Pro Gly Ala Thr Ala Pro Gly Ala Ala Asn
65                  70                  75                  80

Ala Thr Ala Pro Gln Met Arg Thr Pro Ile Leu Leu Leu Arg Asn Asn
                85                  90                  95

Arg Thr Ala Ala Ala Arg Val Arg Thr Ala Gly Pro Ser Ala Ala Ala
            100                 105                 110

Ala Gly Arg Pro Arg Pro Ala Ala Arg His Trp Phe Gln Ala Gly Tyr
        115                 120                 125

Ser Thr Ser Gly Ala His Asp Ala Gly Thr Ser Arg Ala Asp Asn Gln
130                 135                 140

Thr Ala Pro Gly Glu Val Pro Thr Leu Ser Asn Leu Arg Pro Pro Asn
145                 150                 155                 160

Arg Val Glu Val Asp Gly Met Val Gly Asp Asp Pro Tyr Asn Pro Tyr
                165                 170                 175

Lys Tyr Thr Asp Asp Asn Pro Tyr Tyr Asn Tyr Tyr Asp Thr Tyr Glu
            180                 185                 190

Arg Pro Arg Pro Gly Ser Arg Tyr Arg Pro Gly Tyr Gly Thr Gly Tyr
        195                 200                 205

Phe Gln Tyr Gly Leu Pro Asp Leu Val Pro Asp Pro Tyr Tyr Ile Gln
    210                 215                 220

Ala Ser Thr Tyr Val Gln Lys Met Ala Met Tyr Asn Leu Arg Cys Ala
225                 230                 235                 240

Ala Glu Glu Asn Cys Leu Ala Ser Ser Ala Tyr Arg Xaa Asp Val Arg
                245                 250                 255

Asp Tyr Asp His Arg Val Leu Leu Arg Phe Pro Gln Arg Val Lys Asn
            260                 265                 270

Gln Gly Thr Ser Asp Phe Leu Pro Ser Arg Pro Arg Tyr Ser Trp Glu
        275                 280                 285

Trp His Ser Cys His Gln His Tyr His Ser Met Asp Glu Phe Ser His
    290                 295                 300

Tyr Asp Leu Leu Asp Ala Ser Thr Gln Arg Arg Val Ala Glu Gly His
305                 310                 315                 320

Lys Ala Ser Phe Cys Leu Glu Asp Thr Ser Cys Asp Tyr Gly Tyr His
```

|     |     |     | 325 |     |     |     | 330 |     |     |     | 335 |     |
| --- | --- | --- | --- | --- | --- | --- | --- | --- | --- | --- | --- | --- |
| Arg | Arg | Phe | Ala | Cys | Thr | Ala | His | Thr | Gln | Gly | Leu | Ser | Pro | Gly | Cys |
|     |     |     | 340 |     |     |     | 345 |     |     |     | 350 |     |

Tyr Asp Thr Tyr Asn Ala Asp Ile Asp Cys Gln Trp Ile Asp Ile Thr
            355                 360                 365

Asp Val Lys Pro Gly Asn Tyr Ile Leu Lys Val Ser Val Asn Pro Ser
        370                 375                 380

Tyr Leu Val Pro Glu Ser Asp Tyr Ser Asn Asn Val Val Arg Cys Glu
385                 390                 395                 400

Ile Arg Tyr Thr Gly His His Ala Tyr Ala Ser Gly Cys Thr Ile Ser
                405                 410                 415

Pro Tyr

<210> SEQ ID NO 8
<211> LENGTH: 1612
<212> TYPE: DNA
<213> ORGANISM: Artificial Sequence
<220> FEATURE:
<223> OTHER INFORMATION: Synthetic nucleotide: bovine P4HA cDNA
      optimized

<400> SEQUENCE: 8
atgatttggt atatcctagt cgttggtatt ttgttgccac agtcactggc tcacccaggc      60
ttcttcactt ctataggaca gatgactgat ttgattcaca cagaaaaaga cctagttaca     120
agccttaaag actatatcaa agctgaagag ataagttgg agcaaatcaa aaagtgggca     180
gagaaactcg atagattgac tagtactgca acaaaagatc ctgagggttt tgtgggtcac     240
ccagtgaatg ctttcaagct gatgaagaga cttaatacag agtggtcaga attggaaaac     300
ttggtactta agatatgag tgatggattc atttctaact taacaattca agacaaatac     360
tttccaaacg atgaggacca gtaggagca gcaaaagctt tgttgcgatt gcaggacaca     420
tacaatttgg acaccgacac gatatcgaag ggtgatttac ctggtgtgaa gcataagtcc     480
ttcctcactg tggaagattg ttttgaattg ggaaaagtcg catatacaga agccgactac     540
tatcacacag aattatggat ggagcaagct ctgcgtcagt tggacgaagg tgaagtttct     600
accgttgata aggtttcagt tttggattac ttatcatacg ctgtttacca gcaaggtgat     660
ctggacaaag tctactttt aactaaaaag ttgttggagc tggaccccga gcatcaaaga     720
gctaacggta atctgaaata ctttgaatac atcatggcta aggaaaagga cgcaaataag     780
tcctcgtccg atgaccaatc cgatcaaaag accactctga aaaaaaaagg tgcagctgtt     840
gactacctcc cagagagaca aaagtatgaa atgctgtgta gaggagaggg tatcaagatg     900
actccaagga gacagaaaaa gctgttctgt agatatcatg atgggaaccg taacccaaaa     960
ttcattcttg ctccagcgaa acaggaagat gaatgggaca agcctagaat cattcgtttt    1020
catgacatca tctccgatgc agaaatagag gttgtgaaag acttggccaa accaagattg    1080
agtagggcta ccgtccatga ccctgagact ggaaaattga ctaccgcaca atatcgtgtc    1140
tctaaatcag catggttgtc cggttacgag aatcccgtgg tcagccgtat caatatgcgt    1200
attcaagatt tgactggtct tgacgtaagc actgctgagg aactacaagt tgccaactat    1260
ggtgtgggcg gtcagtatga acccccacttt gatttcgcca aaaggacga gcctgatgct    1320
tttaaggagc taggtactgg aaatagaatc gcaacgtggt tgttctatat gtccgatgtg    1380
cttgctggag gagccacagt tttccctgag gtaggtgctc tgtttggcc taaaaagggc    1440
acggccgtat tttggtacaa tctgtttgca tctggagaag gtgattacag cactagacat    1500

| | |
|---|---|
| gctgcttgtc ccgtcttagt cggtaataag tgggtttcca ataagtggct gcatgagaga | 1560 |
| ggtcaagagt ttaggaggcc atgcacattg tcagaattag aatgataatt tt | 1612 |

<210> SEQ ID NO 9
<211> LENGTH: 1747
<212> TYPE: DNA
<213> ORGANISM: Artificial Sequence
<220> FEATURE:
<223> OTHER INFORMATION: Synthetic nucleotide: bovine P4HB (PDI)
      sequence, with Alpha pre-pro signal sequence, cDNA optimized

<400> SEQUENCE: 9

| | |
|---|---|
| atgagattcc catctatttt caccgctgtc ttgttcgctg cctcctctgc attggctgcc | 60 |
| cctgttaaca ctaccactga agacgagact gctcaaattc cagctgaagc agttatcggt | 120 |
| tactctgacc ttgagggtga tttcgacgtc gctgttttgc ctttctctaa ctccactaac | 180 |
| aacggtttgt tgttcattaa caccactatc gcttccattg ctgctaagga gagggtgtc | 240 |
| tctctcgaga aagagaggc cgaagctgca cccgatgagg aagatcatgt tttagtattg | 300 |
| cataaaggaa atttcgatga agctttggcc gctcacaaat atctgctcgt cgagttttac | 360 |
| gctccctggt gcggtcattg taaggccctt gcaccagagt acgccaaggc agctggtaag | 420 |
| ttaaaggccg aaggttcaga gatcagatta gcaaaagttg atgctacaga gagtccgat | 480 |
| cttgctcaac aatacgggt tcaggatac ccaacaatta gttttttcaa aaatggtgat | 540 |
| actgcttccc caaggaata tactgctggt agagaggcag acgacatagt caactggctc | 600 |
| aaaaagagaa cgggcccagc tgcgtctaca ttaagcgacg gagcagcagc cgaagctctt | 660 |
| gtggaatcta gtgaagttgc tgtaatcggt ttctttaagg acatggaatc tgattcagct | 720 |
| aaacagttcc ttttagcagc tgaagcaatc gatgacatcc ctttcggaat cacctcaaat | 780 |
| agtgacgtgt tcagcaagta ccaacttgac aaagatggag tggtcttgtt caaaaagttt | 840 |
| gacgaaggca gaaacaattt cgagggtgag gttacaaagg agaaactgct tgatttcatt | 900 |
| aaacataacc aactacccct agttatcgaa ttcactgaac aaactgctcc taagattttc | 960 |
| ggtggagaaa tcaaaacaca tatcttgttg ttttgccaa gtccgtatc ggattatgaa | 1020 |
| ggtaaactct ccaatttcaa aaaggccgct gagagcttta agggcaagat tttgttcatc | 1080 |
| tttattgact cagaccacac agacaatcag aggattttgg agtttttcgg tttgaaaaag | 1140 |
| gaggaatgtc cagcagtccg tttgatcacc ttggaggagg agatgaccaa atacaaacca | 1200 |
| gagtcggatg agttgactgc cgagaagata acagaattt gtcacagatt ctgggaaggt | 1260 |
| aagatcaagc ctcatcttat gtctcaagag ttgcctgatg actgggataa gcaaccagtt | 1320 |
| aaagtattgg tgggtaaaaa ctttgaggaa gtggccttcg acgagaaaaa aaatgtcttt | 1380 |
| gttgaattct atgctccgtg gtgtggtcac tgtaagcagc tggcaccaat tgggataaa | 1440 |
| ctgggtgaaa cttacaaaga tcacgaaaac attgttattg caaagatgga cagtactgct | 1500 |
| aacgaagtgg aggctgtgaa agttcactcc ttccctacgc tgaagttctt tcctgcatct | 1560 |
| gctgacagaa ctgttatcga ctataatgga gagaggacat ggatggtttt aaaaagttt | 1620 |
| cttgaatccg gaggtcaaga cggagctggt gacgacgatg attttggaaga tctggaggag | 1680 |
| gctgaggaac ctgatcttga ggaggatgac gaccagaagg cagtcaaaga tgaactgtga | 1740 |
| taagggg | 1747 |

<210> SEQ ID NO 10
<211> LENGTH: 4404

```
<212> TYPE: DNA
<213> ORGANISM: Artificial Sequence
<220> FEATURE:
<223> OTHER INFORMATION: Synthetic nucleotide: Col3A1 cDNA optimized

<400> SEQUENCE: 10
atgatgtctt ttgtccaaaa gggtacttgg ttacttttg ctctgttgca cccaactgtt      60
attctcgcac aacaggaagc agtagatggt ggttgctcac atttaggtca atcttacgca     120
gatagagatg tatggaaacc tgaaccatgt caaatttgcg tgtgtgactc aggttcagtg     180
ctctgcgacg atatcatatg tgacgaccag gaattggact gtccaaaccc agagatacca     240
ttcggtgaat gttgtgctgt ttgtccacag ccaccaactg ctcctacaag acctccaaac     300
ggtcaaggtc cacaaggtcc taaaggtgat ccgggtccac ctggtattcc tggtagaaat     360
ggtgaccctg gacctcccgg ttccccaggt agcccaggat cacctgggcc tcctggaata     420
tgtgaatcct gcccaactgg tggtcagaac tatagcccac aatacgaggc ctacgacgtc     480
aaatctggtg ttgctggagg aggtattgca ggctaccctg gtcccgcagg gcccccaggt     540
ccgccgggtc cgcccggaac atcaggtcat cccggagccc tggtgcacc aggttatcag      600
ggaccgcccg gagagcctgg acaagctggt cccgctggac cccctggtcc accaggtgct     660
attggaccaa gtggtcctgc cggaaaagac ggtgaatccg gtagacctgg tagacccggc     720
gaaaggggtt tcccaggtcc tcccggaatg aaggtccag ccggtatgcc cggtttttcct     780
gggatgaagg gtcacagagg atttgatggt agaaacggag agaaggcga aaccggtgct      840
cccggactga agggtgaaaa cggtgtccct ggtgagaacg gcgctcctgg acctatgggt     900
ccacgtggtg ctccaggaga agaggcaga ccaggattgc ctggtgcagc tggtgctaga     960
ggtaacgatg gtgcccgtgg ttccgatgga caacccgggc cacccggccc tccaggtacc    1020
gctggatttc ctggaagccc tggtgctaag gggaggttg tccggctgg tagtcccgga      1080
agtagcggtg cccaggtca aagaggcgaa ccaggccctc agggtcacgc aggagcacct    1140
ggaccgcctg gtcctcctgg ttcgaatggt tcgcctggag aaaaggtga atgggggccc     1200
gcaggaatcc ccggtgcgcc tggtctatt ggtgccaggg gtcctccagg cccgccaggt     1260
acaaatggtg tacccggaca gcgaggagca gctggtgaac ctggtaaaaa cggtgccaaa    1320
ggagatccag gtcctcgtgg agagcgtggt gaagctggct ctcccggtat cgccggtcca    1380
aaaggtgagg acgtaagga cggttcccct ggtgagccag gtgcgaacgg actgccaggt    1440
gcagccggag agcgaggagt cccaggattc aggggaccag ccggtgctaa cggcttgcct    1500
ggtgaaaaag gccccctgg tgatagggga ggacccggtc cagcaggccc tcgtggagtt     1560
gctggtgagc ctggacgtga cggtttacca ggagggccag gtttgagggg tattcccggg    1620
tccccctggcg gtcctggatc ggatggaaaa ccagggccac caggttcgca gggtgaaaca    1680
ggacgtccag gcccacccgg ctcacctggt ccaaggggtc agcctggtgt catgggtttc    1740
cccggtccaa agggtaatga cggagcaccg gtaaaaatg gtgaacgtgg tgcccaggt      1800
ggtccaggac cccaaggtcc agctggaaaa acggtgaga caggtcctca aggacctcca    1860
ggacctaccg gtcctagcgg agataaggga gatacgggac cgccaggacc tcaaggattg    1920
caaggtttgc ctggtacatc tggccctccc ggagaaaatg gtaagcctgg agagccagga    1980
ccaaaaggcg aagctggagc cccaggtatc cccggaggta agggagactc aggtgctccg    2040
ggtgagcgtg gtcctccggg tgccggtggt ccacctggac ctagaggtgg tgccgggccg    2100
ccaggtcctg aaggtggtaa aggtgctgct ggtccaccgg gaccgcctgg ctctgctggt    2160
```

```
actcctggct tgcagggaat gccaggagag agaggtggac ctggaggtcc cggtccgaag     2220
ggtgataaag gggagccagg atcatccggt gttgacggcg cacctggtaa agacggacca     2280
aggggaccaa cgggtccaat cggaccacca ggacccgctg gccagccagg agataaaggc     2340
gagtccggag cacccggtgt tcctggtata gctggaccca ggggtggtcc cggtgaaaga     2400
ggtgaacagg gcccaccggg tcccgccggt ttccctggcg cccctggtca aaatggagaa     2460
ccaggtgcaa agggcgagag aggagcccca ggagaaaagg gtgagggagg accacccggt     2520
gctgccggtc cagctggggg ttcaggtcct gctggaccac caggtccaca gggcgttaaa     2580
ggtgagagag gaagtccagg tggtcctgga gctgctggat cccaggtgg ccgtggacct     2640 cctggtcccc ctggatcgaa tggtaatcct ggtccgccag gtagttcggg tgctcctggg     2700
aaggacggtc cacctggccc cccaggtagt aacggtgcac ctggtagtcc aggtatatcc     2760
ggacctaaag gagattccgg tccaccaggc gaaagagggg ccccaggccc acagggtcca     2820
ccaggagccc ccggtcctct gggtattgct ggtcttactg gtgcacgtgg actggccggt     2880 ccaccccggaa tgcctggagc aagaggttca cctggaccac aaggtattaa aggagagaac     2940
ggtaaacctg gaccttccgg tcaaaacgga gagcggggac ccccaggccc caaggtctg     3000 ccaggactag ctggtaccgc aggggaacca ggaagagatg gaaatccagg ttcagacgga     3060
ctacccggta gagatggtgc accgggggcc aagggcgaca ggggtgagaa tggatctcct     3120
ggtgcgccag gggcaccagg ccacccaggt cccccaggtc ctgtgggccc tgctggaaag     3180
tcaggtgaca ggggagagac aggcccggct ggtccatctg gcgcacccgg accagctggt     3240
tccagaggcc cacctggtcc gcaaggccct agaggtgaca aggagagac tggagaacga     3300 ggtgctatgg gtatcaaggg tcatagaggt tttccgggta atcccggcgc cccaggttct     3360
cctggtccag ctggccatca aggtgcagtc ggatcgcccg gccagccgg tcccaggggc     3420 cctgttggtc catccggtcc tccaggaaag gatggtgctt ctggacaccc aggacctatc     3480
ggacctccgg gtcctagagg taatagagga gaacgtggat ccgagggtag tcctggtcac     3540
cctggtcaac ctggcccacc agggcctcca ggtgcacccg gtccatgttg tggtgcaggc     3600
ggtgtggctg caattgctgg tgtgggtgct gaaaaggccg gcggtttcgc tccatattat     3660
ggtgatgaac cgattgattt taagatcaat actgacgaaa tcatgacttc cttaaagtcc     3720
gttaatggtc aaattgagtc tctaatctcc ccagatggtt cacgtaaaaa tcctgctaga     3780
aattgtagag atttgaagtt ttgtcacccc gagttgcagt ccggtgagta ctgggtggac     3840
cccaatcaag gttgtaagtt agacgctatt aaagtttact gcaatatgga gacaggagaa     3900
acttgcatca gcgcttctcc attgactatc ccacaaaaaa attggtggac tgactctgga     3960
gctgagaaaa agcatgtatg gttcggggaa tcgatggaag gtggtttcca attcagctac     4020
ggtaaccctg aacttcctga agatgttctt gacgttcaat ggcattct gagattgttg     4080 tccagtcgtg caagccaaaa cattacatac cattgcaaaa attccatcgc atatatggat     4140
catgctagcg gaaatgtgaa aaaggcattg aagctgatgg gatcaaatga aggtgaattt     4200
aaagcagagg gtaattctaa gtttacttac actgtattgg aggatggttg tacgaagcat     4260
acaggtgaat ggggtaaaac agtgtttcaa tatcaaaccc gcaaagcagt tagattgcca     4320
atcgtcgata tcgcaccata cgacattgga ggaccagatc aagagttcgg agctgacatc     4380
ggtccggtgt gtttcctttg ataa                                            4404
```

<210> SEQ ID NO 11
<211> LENGTH: 1463

<212> TYPE: PRT
<213> ORGANISM: Artificial Sequence
<220> FEATURE:
<223> OTHER INFORMATION: Synthetic peptide: collagen alpha-1(I) chain
       precursor (Bos taurus), NCBI reference sequence NP_001029211.1

<400> SEQUENCE: 11

Met Phe Ser Phe Val Asp Leu Arg Leu Leu Leu Leu Ala Ala Thr
1               5                   10                  15

Ala Leu Leu Thr His Gly Gln Glu Gly Gln Glu Glu Gly Gln Glu
            20                  25                  30

Glu Asp Ile Pro Pro Val Thr Cys Val Gln Asn Gly Leu Arg Tyr His
            35                  40                  45

Asp Arg Asp Val Trp Lys Pro Val Pro Cys Gln Ile Cys Val Cys Asp
        50                  55                  60

Asn Gly Asn Val Leu Cys Asp Asp Val Ile Cys Asp Glu Leu Lys Asp
65                  70                  75                  80

Cys Pro Asn Ala Lys Val Pro Thr Asp Glu Cys Cys Pro Val Cys Pro
                85                  90                  95

Glu Gly Gln Glu Ser Pro Thr Asp Gln Glu Thr Thr Gly Val Glu Gly
            100                 105                 110

Pro Lys Gly Asp Thr Gly Pro Arg Gly Pro Arg Gly Pro Ala Gly Pro
            115                 120                 125

Pro Gly Arg Asp Gly Ile Pro Gly Gln Pro Gly Leu Pro Gly Pro Pro
        130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Ile Ser Val
                165                 170                 175

Pro Gly Pro Met Gly Pro Ser Gly Pro Arg Gly Leu Pro Gly Pro Pro
            180                 185                 190

Gly Ala Pro Gly Pro Gln Gly Phe Gln Gly Pro Pro Gly Glu Pro Gly
            195                 200                 205

Glu Pro Gly Ala Ser Gly Pro Met Gly Pro Arg Gly Pro Pro Gly Pro
210                 215                 220

Pro Gly Lys Asn Gly Asp Asp Gly Glu Ala Gly Lys Pro Gly Arg Pro
225                 230                 235                 240

Gly Glu Arg Gly Pro Pro Gly Pro Gln Gly Ala Arg Gly Leu Pro Gly
                245                 250                 255

Thr Ala Gly Leu Pro Gly Met Lys Gly His Arg Gly Phe Ser Gly Leu
            260                 265                 270

Asp Gly Ala Lys Gly Asp Ala Gly Pro Ala Gly Pro Lys Gly Glu Pro
        275                 280                 285

Gly Ser Pro Gly Glu Asn Gly Ala Pro Gly Gln Met Gly Pro Arg Gly
            290                 295                 300

Leu Pro Gly Glu Arg Gly Arg Pro Gly Ala Pro Gly Pro Ala Gly Ala
305                 310                 315                 320

Arg Gly Asn Asp Gly Ala Thr Gly Ala Ala Gly Pro Pro Gly Pro Thr
                325                 330                 335

Gly Pro Ala Gly Pro Pro Gly Phe Pro Gly Ala Val Gly Ala Lys Gly
            340                 345                 350

Glu Gly Gly Pro Gln Gly Pro Arg Gly Ser Glu Gly Pro Gln Gly Val
        355                 360                 365

Arg Gly Glu Pro Gly Pro Pro Gly Pro Ala Gly Ala Ala Gly Pro Ala
            370                 375                 380

```
Gly Asn Pro Gly Ala Asp Gln Pro Gly Ala Lys Gly Ala Asn Gly
385                 390                 395                 400

Ala Pro Gly Ile Ala Gly Ala Pro Gly Phe Pro Gly Ala Arg Gly Pro
            405                 410                 415

Ser Gly Pro Gln Gly Pro Ser Gly Pro Pro Gly Pro Lys Gly Asn Ser
            420                 425                 430

Gly Glu Pro Gly Ala Pro Gly Ser Lys Gly Asp Thr Gly Ala Lys Gly
            435                 440                 445

Glu Pro Gly Pro Thr Gly Ile Gln Gly Pro Pro Gly Pro Ala Gly Glu
    450                 455                 460

Glu Gly Lys Arg Gly Ala Arg Gly Glu Pro Gly Pro Ala Gly Leu Pro
465                 470                 475                 480

Gly Pro Pro Gly Glu Arg Gly Gly Pro Gly Ser Arg Gly Phe Pro Gly
                485                 490                 495

Ala Asp Gly Val Ala Gly Pro Lys Gly Pro Ala Gly Glu Arg Gly Ala
            500                 505                 510

Pro Gly Pro Ala Gly Pro Lys Gly Ser Pro Gly Glu Ala Gly Arg Pro
    515                 520                 525

Gly Glu Ala Gly Leu Pro Gly Ala Lys Gly Leu Thr Gly Ser Pro Gly
530                 535                 540

Ser Pro Gly Pro Asp Gly Lys Thr Gly Pro Pro Gly Pro Ala Gly Gln
545                 550                 555                 560

Asp Gly Arg Pro Gly Pro Pro Gly Pro Pro Gly Ala Arg Gly Gln Ala
            565                 570                 575

Gly Val Met Gly Phe Pro Gly Pro Lys Gly Ala Ala Gly Glu Pro Gly
            580                 585                 590

Lys Ala Gly Glu Arg Gly Val Pro Gly Pro Pro Gly Ala Val Gly Pro
    595                 600                 605

Ala Gly Lys Asp Gly Glu Ala Gly Ala Gln Gly Pro Pro Gly Pro Ala
        610                 615                 620

Gly Pro Ala Gly Glu Arg Gly Glu Gln Gly Pro Ala Gly Ser Pro Gly
625                 630                 635                 640

Phe Gln Gly Leu Pro Gly Pro Ala Gly Pro Pro Gly Glu Ala Gly Lys
            645                 650                 655

Pro Gly Glu Gln Gly Val Pro Gly Asp Leu Gly Ala Pro Gly Pro Ser
            660                 665                 670

Gly Ala Arg Gly Glu Arg Gly Phe Pro Gly Glu Arg Gly Val Gln Gly
            675                 680                 685

Pro Pro Gly Pro Ala Gly Pro Arg Gly Ala Asn Gly Ala Pro Gly Asn
    690                 695                 700

Asp Gly Ala Lys Gly Asp Ala Gly Ala Pro Gly Ala Pro Gly Ser Gln
705                 710                 715                 720

Gly Ala Pro Gly Leu Gln Gly Met Pro Gly Glu Arg Gly Ala Ala Gly
            725                 730                 735

Leu Pro Gly Pro Lys Gly Asp Arg Gly Asp Ala Gly Pro Lys Gly Ala
            740                 745                 750

Asp Gly Ala Pro Gly Lys Asp Gly Val Arg Gly Leu Thr Gly Pro Ile
            755                 760                 765

Gly Pro Pro Gly Pro Ala Gly Ala Pro Gly Asp Lys Gly Glu Ala Gly
    770                 775                 780

Pro Ser Gly Pro Ala Gly Pro Thr Gly Ala Arg Gly Ala Pro Gly Asp
785                 790                 795                 800
```

```
Arg Gly Glu Pro Gly Pro Pro Gly Pro Ala Gly Phe Ala Gly Pro Pro
            805                 810                 815

Gly Ala Asp Gly Gln Pro Gly Ala Lys Gly Glu Pro Gly Asp Ala Gly
        820                 825                 830

Ala Lys Gly Asp Ala Gly Pro Pro Gly Pro Ala Gly Pro Ala Gly Pro
    835                 840                 845

Pro Gly Pro Ile Gly Asn Val Gly Ala Pro Gly Pro Lys Gly Ala Arg
850                 855                 860

Gly Ser Ala Gly Pro Pro Gly Ala Thr Gly Phe Pro Gly Ala Ala Gly
865                 870                 875                 880

Arg Val Gly Pro Pro Gly Pro Ser Gly Asn Ala Gly Pro Pro Gly Pro
            885                 890                 895

Pro Gly Pro Ala Gly Lys Glu Gly Ser Lys Gly Pro Arg Gly Glu Thr
        900                 905                 910

Gly Pro Ala Gly Arg Pro Gly Glu Val Gly Pro Pro Gly Pro Pro Gly
    915                 920                 925

Pro Ala Gly Glu Lys Gly Ala Pro Gly Ala Asp Gly Pro Ala Gly Ala
930                 935                 940

Pro Gly Thr Pro Gly Pro Gln Gly Ile Ala Gly Gln Arg Gly Val Val
945                 950                 955                 960

Gly Leu Pro Gly Gln Arg Gly Glu Arg Gly Phe Pro Gly Leu Pro Gly
            965                 970                 975

Pro Ser Gly Glu Pro Gly Lys Gln Gly Pro Ser Gly Ala Ser Gly Glu
        980                 985                 990

Arg Gly Pro Pro Gly Pro Met Gly Pro Pro Gly Leu Ala Gly Pro Pro
    995                 1000                1005

Gly Glu Ser Gly Arg Glu Gly Ala Pro Gly Ala Glu Gly Ser Pro
    1010                1015                1020

Gly Arg Asp Gly Ser Pro Gly Ala Lys Gly Asp Arg Gly Glu Thr
    1025                1030                1035

Gly Pro Ala Gly Pro Pro Gly Ala Pro Gly Ala Pro Gly Ala Pro
    1040                1045                1050

Gly Pro Val Gly Pro Ala Gly Lys Ser Gly Asp Arg Gly Glu Thr
    1055                1060                1065

Gly Pro Ala Gly Pro Ala Gly Pro Ile Gly Pro Val Gly Ala Arg
    1070                1075                1080

Gly Pro Ala Gly Pro Gln Gly Pro Arg Gly Asp Lys Gly Glu Thr
    1085                1090                1095

Gly Glu Gln Gly Asp Arg Gly Ile Lys Gly His Arg Gly Phe Ser
    1100                1105                1110

Gly Leu Gln Gly Pro Pro Gly Pro Pro Gly Ser Pro Gly Glu Gln
    1115                1120                1125

Gly Pro Ser Gly Ala Ser Gly Pro Ala Gly Pro Arg Gly Pro Pro
    1130                1135                1140

Gly Ser Ala Gly Ser Pro Gly Lys Asp Gly Leu Asn Gly Leu Pro
    1145                1150                1155

Gly Pro Ile Gly Pro Pro Gly Pro Arg Gly Arg Thr Gly Asp Ala
    1160                1165                1170

Gly Pro Ala Gly Pro Pro Gly Pro Pro Gly Pro Pro Gly Pro Pro
    1175                1180                1185

Gly Pro Pro Ser Gly Gly Tyr Asp Leu Ser Phe Leu Pro Gln Pro
    1190                1195                1200

Pro Gln Glu Lys Ala His Asp Gly Gly Arg Tyr Tyr Arg Ala Asp
```

1205                1210                1215

Asp Ala Asn Val Val Arg Asp Arg Asp Leu Glu Val Asp Thr Thr
    1220                1225                1230

Leu Lys Ser Leu Ser Gln Gln Ile Glu Asn Ile Arg Ser Pro Glu
    1235                1240                1245

Gly Ser Arg Lys Asn Pro Ala Arg Thr Cys Arg Asp Leu Lys Met
    1250                1255                1260

Cys His Ser Asp Trp Lys Ser Gly Glu Tyr Trp Ile Asp Pro Asn
    1265                1270                1275

Gln Gly Cys Asn Leu Asp Ala Ile Lys Val Phe Cys Asn Met Glu
    1280                1285                1290

Thr Gly Glu Thr Cys Val Tyr Pro Thr Gln Pro Ser Val Ala Gln
    1295                1300                1305

Lys Asn Trp Tyr Ile Ser Lys Asn Pro Lys Glu Lys Arg His Val
    1310                1315                1320

Trp Tyr Gly Glu Ser Met Thr Gly Gly Phe Gln Phe Glu Tyr Gly
    1325                1330                1335

Gly Gln Gly Ser Asp Pro Ala Asp Val Ala Ile Gln Leu Thr Phe
    1340                1345                1350

Leu Arg Leu Met Ser Thr Glu Ala Ser Gln Asn Ile Thr Tyr His
    1355                1360                1365

Cys Lys Asn Ser Val Ala Tyr Met Asp Gln Gln Thr Gly Asn Leu
    1370                1375                1380

Lys Lys Ala Leu Leu Leu Gln Gly Ser Asn Glu Ile Glu Ile Arg
    1385                1390                1395

Ala Glu Gly Asn Ser Arg Phe Thr Tyr Ser Val Thr Tyr Asp Gly
    1400                1405                1410

Cys Thr Ser His Thr Gly Ala Trp Gly Lys Thr Val Ile Glu Tyr
    1415                1420                1425

Lys Thr Thr Lys Thr Ser Arg Leu Pro Ile Ile Asp Val Ala Pro
    1430                1435                1440

Leu Asp Val Gly Ala Pro Asp Gln Glu Phe Gly Phe Asp Val Gly
    1445                1450                1455

Pro Ala Cys Phe Leu
    1460

<210> SEQ ID NO 12
<211> LENGTH: 1364
<212> TYPE: PRT
<213> ORGANISM: Artificial Sequence
<220> FEATURE:
<223> OTHER INFORMATION: Synthetic peptide: collagen alpha-2(I) chain
      precursor (Bos taurus), NCBI reference sequence: NP_776945.1

<400> SEQUENCE: 12

Met Leu Ser Phe Val Asp Thr Arg Thr Leu Leu Leu Leu Ala Val Thr
1               5                   10                  15

Ser Cys Leu Ala Thr Cys Gln Ser Leu Gln Glu Ala Thr Ala Arg Lys
                20                  25                  30

Gly Pro Ser Gly Asp Arg Gly Pro Arg Gly Glu Arg Gly Pro Pro Gly
            35                  40                  45

Pro Pro Gly Arg Asp Gly Asp Asp Gly Ile Pro Gly Pro Pro Gly Pro
        50                  55                  60

Pro Gly Pro Pro Gly Pro Pro Gly Leu Gly Gly Asn Phe Ala Ala Gln
65                  70                  75                  80

```
Phe Asp Ala Lys Gly Gly Pro Gly Pro Met Gly Leu Met Gly Pro
                85                  90                  95

Arg Gly Pro Pro Gly Ala Ser Gly Ala Pro Gly Pro Gln Gly Phe Gln
            100                 105                 110

Gly Pro Pro Gly Glu Pro Gly Glu Pro Gly Gln Thr Gly Pro Ala Gly
        115                 120                 125

Ala Arg Gly Pro Pro Gly Pro Pro Gly Lys Ala Gly Glu Asp Gly His
    130                 135                 140

Pro Gly Lys Pro Gly Arg Pro Gly Glu Arg Gly Val Val Gly Pro Gln
145                 150                 155                 160

Gly Ala Arg Gly Phe Pro Gly Thr Pro Gly Leu Pro Gly Phe Lys Gly
                165                 170                 175

Ile Arg Gly His Asn Gly Leu Asp Gly Leu Lys Gly Gln Pro Gly Ala
                180                 185                 190

Pro Gly Val Lys Gly Glu Pro Gly Ala Pro Gly Glu Asn Gly Thr Pro
            195                 200                 205

Gly Gln Thr Gly Ala Arg Gly Leu Pro Gly Glu Arg Gly Arg Val Gly
        210                 215                 220

Ala Pro Gly Pro Ala Gly Ala Arg Gly Ser Asp Gly Ser Val Gly Pro
225                 230                 235                 240

Val Gly Pro Ala Gly Pro Ile Gly Ser Ala Gly Pro Pro Gly Phe Pro
                245                 250                 255

Gly Ala Pro Gly Pro Lys Gly Glu Leu Gly Pro Val Gly Asn Pro Gly
            260                 265                 270

Pro Ala Gly Pro Ala Gly Pro Arg Gly Glu Val Gly Leu Pro Gly Leu
        275                 280                 285

Ser Gly Pro Val Gly Pro Pro Gly Asn Pro Gly Ala Asn Gly Leu Pro
    290                 295                 300

Gly Ala Lys Gly Ala Ala Gly Leu Pro Gly Val Ala Gly Ala Pro Gly
305                 310                 315                 320

Leu Pro Gly Pro Arg Gly Ile Pro Gly Pro Val Gly Ala Ala Gly Ala
                325                 330                 335

Thr Gly Ala Arg Gly Leu Val Gly Glu Pro Gly Pro Ala Gly Ser Lys
            340                 345                 350

Gly Glu Ser Gly Asn Lys Gly Glu Pro Gly Ala Val Gly Gln Pro Gly
        355                 360                 365

Pro Pro Gly Pro Ser Gly Glu Glu Gly Lys Arg Gly Ser Thr Gly Glu
    370                 375                 380

Ile Gly Pro Ala Gly Pro Pro Gly Pro Pro Gly Leu Arg Gly Asn Pro
385                 390                 395                 400

Gly Ser Arg Gly Leu Pro Gly Ala Asp Gly Arg Ala Gly Val Met Gly
                405                 410                 415

Pro Ala Gly Ser Arg Gly Ala Thr Gly Pro Ala Gly Val Arg Gly Pro
            420                 425                 430

Asn Gly Asp Ser Gly Arg Pro Gly Glu Pro Gly Leu Met Gly Pro Arg
        435                 440                 445

Gly Phe Pro Gly Ser Pro Gly Asn Ile Gly Pro Ala Gly Lys Glu Gly
    450                 455                 460

Pro Val Gly Leu Pro Gly Ile Asp Gly Arg Pro Gly Pro Ile Gly Pro
465                 470                 475                 480

Ala Gly Ala Arg Gly Glu Pro Gly Asn Ile Gly Phe Pro Gly Pro Lys
                485                 490                 495

Gly Pro Ser Gly Asp Pro Gly Lys Ala Gly Glu Lys Gly His Ala Gly
```

```
                500             505             510
Leu Ala Gly Ala Arg Gly Ala Pro Gly Pro Asp Gly Asn Asn Gly Ala
            515             520             525
Gln Gly Pro Pro Gly Leu Gln Gly Val Gln Gly Gly Lys Gly Glu Gln
        530             535             540
Gly Pro Ala Gly Pro Pro Gly Phe Gln Gly Leu Pro Gly Pro Ala Gly
545             550             555             560
Thr Ala Gly Glu Ala Gly Lys Pro Gly Glu Arg Gly Ile Pro Gly Glu
            565             570             575
Phe Gly Leu Pro Gly Pro Ala Gly Ala Arg Gly Glu Arg Gly Pro Pro
        580             585             590
Gly Glu Ser Gly Ala Ala Gly Pro Thr Gly Pro Ile Gly Ser Arg Gly
            595             600             605
Pro Ser Gly Pro Pro Gly Pro Asp Gly Asn Lys Gly Glu Pro Gly Val
        610             615             620
Val Gly Ala Pro Gly Thr Ala Gly Pro Ser Gly Pro Ser Gly Leu Pro
625             630             635             640
Gly Glu Arg Gly Ala Ala Gly Ile Pro Gly Gly Lys Gly Glu Lys Gly
            645             650             655
Glu Thr Gly Leu Arg Gly Asp Ile Gly Ser Pro Gly Arg Asp Gly Ala
        660             665             670
Arg Gly Ala Pro Gly Ala Ile Gly Ala Pro Gly Pro Ala Gly Ala Asn
            675             680             685
Gly Asp Arg Gly Glu Ala Gly Pro Ala Gly Pro Ala Gly Pro Ala Gly
        690             695             700
Pro Arg Gly Ser Pro Gly Glu Arg Gly Glu Val Gly Pro Ala Gly Pro
705             710             715             720
Asn Gly Phe Ala Gly Pro Ala Gly Ala Ala Gly Gln Pro Gly Ala Lys
            725             730             735
Gly Glu Arg Gly Thr Lys Gly Pro Lys Gly Glu Asn Gly Pro Val Gly
        740             745             750
Pro Thr Gly Pro Val Gly Ala Ala Gly Pro Ser Gly Pro Asn Gly Pro
            755             760             765
Pro Gly Pro Ala Gly Ser Arg Gly Asp Gly Gly Pro Pro Gly Ala Thr
        770             775             780
Gly Phe Pro Gly Ala Ala Gly Arg Thr Gly Pro Pro Gly Pro Ser Gly
785             790             795             800
Ile Ser Gly Pro Pro Gly Pro Pro Gly Pro Ala Gly Lys Glu Gly Leu
            805             810             815
Arg Gly Pro Arg Gly Asp Gln Gly Pro Val Gly Arg Ser Gly Glu Thr
        820             825             830
Gly Ala Ser Gly Pro Pro Gly Phe Val Gly Glu Lys Gly Pro Ser Gly
            835             840             845
Glu Pro Gly Thr Ala Gly Pro Pro Gly Thr Pro Gly Pro Gln Gly Leu
        850             855             860
Leu Gly Ala Pro Gly Phe Leu Gly Leu Pro Gly Ser Arg Gly Glu Arg
865             870             875             880
Gly Leu Pro Gly Val Ala Gly Ser Val Gly Glu Pro Gly Pro Leu Gly
            885             890             895
Ile Ala Gly Pro Pro Gly Ala Arg Gly Pro Pro Gly Asn Val Gly Asn
        900             905             910
Pro Gly Val Asn Gly Ala Pro Gly Glu Ala Gly Arg Asp Gly Asn Pro
            915             920             925
```

```
Gly Asn Asp Gly Pro Pro Gly Arg Asp Gly Gln Pro Gly His Lys Gly
    930                 935                 940

Glu Arg Gly Tyr Pro Gly Asn Ala Gly Pro Val Gly Ala Ala Gly Ala
945                 950                 955                 960

Pro Gly Pro Gln Gly Pro Val Gly Pro Val Gly Lys His Gly Asn Arg
                965                 970                 975

Gly Glu Pro Gly Pro Ala Gly Ala Val Gly Pro Ala Gly Ala Val Gly
            980                 985                 990

Pro Arg Gly Pro Ser Gly Pro Gln Gly Ile Arg Gly Asp Lys Gly Glu
        995                 1000                1005

Pro Gly Asp Lys Gly Pro Arg Gly Leu Pro Gly Leu Lys Gly His
    1010                1015                1020

Asn Gly Leu Gln Gly Leu Pro Gly Leu Ala Gly His His Gly Asp
    1025                1030                1035

Gln Gly Ala Pro Gly Ala Val Gly Pro Ala Gly Pro Arg Gly Pro
    1040                1045                1050

Ala Gly Pro Ser Gly Pro Ala Gly Lys Asp Gly Arg Ile Gly Gln
    1055                1060                1065

Pro Gly Ala Val Gly Pro Ala Gly Ile Arg Gly Ser Gln Gly Ser
    1070                1075                1080

Gln Gly Pro Ala Gly Pro Gly Pro Pro Gly Pro Pro Gly Pro
    1085                1090                1095

Pro Gly Pro Ser Gly Gly Gly Tyr Glu Phe Gly Phe Asp Gly Asp
    1100                1105                1110

Phe Tyr Arg Ala Asp Gln Pro Arg Ser Pro Thr Ser Leu Arg Pro
    1115                1120                1125

Lys Asp Tyr Glu Val Asp Ala Thr Leu Lys Ser Leu Asn Asn Gln
    1130                1135                1140

Ile Glu Thr Leu Leu Thr Pro Glu Gly Ser Arg Lys Asn Pro Ala
    1145                1150                1155

Arg Thr Cys Arg Asp Leu Arg Leu Ser His Pro Glu Trp Ser Ser
    1160                1165                1170

Gly Tyr Tyr Trp Ile Asp Pro Asn Gln Gly Cys Thr Met Asp Ala
    1175                1180                1185

Ile Lys Val Tyr Cys Asp Phe Ser Thr Gly Glu Thr Cys Ile Arg
    1190                1195                1200

Ala Gln Pro Glu Asp Ile Pro Val Lys Asn Trp Tyr Arg Asn Ser
    1205                1210                1215

Lys Ala Lys Lys His Val Trp Val Gly Glu Thr Ile Asn Gly Gly
    1220                1225                1230

Thr Gln Phe Glu Tyr Asn Val Glu Gly Val Thr Thr Lys Glu Met
    1235                1240                1245

Ala Thr Gln Leu Ala Phe Met Arg Leu Leu Ala Asn His Ala Ser
    1250                1255                1260

Gln Asn Ile Thr Tyr His Cys Lys Asn Ser Ile Ala Tyr Met Asp
    1265                1270                1275

Glu Glu Thr Gly Asn Leu Lys Lys Ala Val Ile Leu Gln Gly Ser
    1280                1285                1290

Asn Asp Val Glu Leu Val Ala Glu Gly Asn Ser Arg Phe Thr Tyr
    1295                1300                1305

Thr Val Leu Val Asp Gly Cys Ser Lys Lys Thr Asn Glu Trp Gln
    1310                1315                1320
```

```
Lys Thr Ile Ile Glu Tyr Lys Thr Asn Lys Pro Ser Arg Leu Pro
    1325                1330                1335

Ile Leu Asp Ile Ala Pro Leu Asp Ile Gly Gly Ala Asp Gln Glu
    1340                1345                1350

Ile Arg Leu Asn Ile Gly Pro Val Cys Phe Lys
    1355                1360

<210> SEQ ID NO 13
<211> LENGTH: 1466
<212> TYPE: PRT
<213> ORGANISM: Artificial Sequence
<220> FEATURE:
<223> OTHER INFORMATION: Synthetic peptide: collagen alpha-1(III) chain
      precursor (Bos taurus), NCBI reference sequence: NP_001070299.1

<400> SEQUENCE: 13

Met Met Ser Phe Val Gln Lys Gly Thr Trp Leu Leu Phe Ala Leu Leu
1               5                   10                  15

His Pro Thr Val Ile Leu Ala Gln Gln Glu Ala Val Asp Gly Gly Cys
            20                  25                  30

Ser His Leu Gly Gln Ser Tyr Ala Asp Arg Asp Val Trp Lys Pro Glu
        35                  40                  45

Pro Cys Gln Ile Cys Val Cys Asp Ser Gly Ser Val Leu Cys Asp Asp
    50                  55                  60

Ile Ile Cys Asp Asp Gln Glu Leu Asp Cys Pro Asn Pro Glu Ile Pro
65                  70                  75                  80

Phe Gly Glu Cys Cys Ala Val Cys Pro Gln Pro Pro Thr Ala Pro Thr
                85                  90                  95

Arg Pro Pro Asn Gly Gln Gly Pro Gln Gly Pro Lys Gly Asp Pro Gly
            100                 105                 110

Pro Pro Gly Ile Pro Gly Arg Asn Gly Asp Pro Gly Pro Pro Gly Ser
        115                 120                 125

Pro Gly Ser Pro Gly Ser Pro Gly Pro Pro Gly Ile Cys Glu Ser Cys
    130                 135                 140

Pro Thr Gly Gly Gln Asn Tyr Ser Pro Gln Tyr Glu Ala Tyr Asp Val
145                 150                 155                 160

Lys Ser Gly Val Ala Gly Gly Gly Ile Ala Gly Tyr Pro Gly Pro Ala
                165                 170                 175

Gly Pro Pro Gly Pro Pro Gly Pro Pro Gly Thr Ser Gly His Pro Gly
            180                 185                 190

Ala Pro Gly Ala Pro Gly Tyr Gln Gly Pro Pro Gly Glu Pro Gly Gln
        195                 200                 205

Ala Gly Pro Ala Gly Pro Pro Gly Pro Pro Gly Ala Ile Gly Pro Ser
    210                 215                 220

Gly Pro Ala Gly Lys Asp Gly Glu Ser Gly Arg Pro Gly Arg Pro Gly
225                 230                 235                 240

Glu Arg Gly Phe Pro Gly Pro Pro Gly Met Lys Gly Pro Ala Gly Met
                245                 250                 255

Pro Gly Phe Pro Gly Met Lys Gly His Arg Gly Phe Asp Gly Arg Asn
            260                 265                 270

Gly Glu Lys Gly Glu Thr Gly Ala Pro Gly Leu Lys Gly Glu Asn Gly
        275                 280                 285

Val Pro Gly Glu Asn Gly Ala Pro Gly Pro Met Gly Pro Arg Gly Ala
    290                 295                 300

Pro Gly Glu Arg Gly Arg Pro Gly Leu Pro Gly Ala Ala Gly Ala Arg
305                 310                 315                 320
```

```
Gly Asn Asp Gly Ala Arg Gly Ser Asp Gly Gln Pro Gly Pro Pro Gly
                325                 330                 335

Pro Pro Gly Thr Ala Gly Phe Pro Gly Ser Pro Gly Ala Lys Gly Glu
            340                 345                 350

Val Gly Pro Ala Gly Ser Pro Gly Ser Ser Gly Ala Pro Gly Gln Arg
        355                 360                 365

Gly Glu Pro Gly Pro Gln Gly His Ala Gly Ala Pro Gly Pro Pro Gly
    370                 375                 380

Pro Pro Gly Ser Asn Gly Ser Pro Gly Gly Lys Gly Glu Met Gly Pro
385                 390                 395                 400

Ala Gly Ile Pro Gly Ala Pro Gly Leu Ile Gly Ala Arg Gly Pro Pro
                405                 410                 415

Gly Pro Pro Gly Thr Asn Gly Val Pro Gly Gln Arg Gly Ala Ala Gly
            420                 425                 430

Glu Pro Gly Lys Asn Gly Ala Lys Gly Asp Pro Gly Pro Arg Gly Glu
        435                 440                 445

Arg Gly Glu Ala Gly Ser Pro Gly Ile Ala Gly Pro Lys Gly Glu Asp
    450                 455                 460

Gly Lys Asp Gly Ser Pro Gly Glu Pro Gly Ala Asn Gly Leu Pro Gly
465                 470                 475                 480

Ala Ala Gly Glu Arg Gly Val Pro Gly Phe Arg Gly Pro Ala Gly Ala
                485                 490                 495

Asn Gly Leu Pro Gly Glu Lys Gly Pro Pro Gly Asp Arg Gly Gly Pro
            500                 505                 510

Gly Pro Ala Gly Pro Arg Gly Val Ala Gly Glu Pro Gly Arg Asp Gly
        515                 520                 525

Leu Pro Gly Gly Pro Gly Leu Arg Gly Ile Pro Gly Ser Pro Gly Gly
    530                 535                 540

Pro Gly Ser Asp Gly Lys Pro Gly Pro Pro Gly Ser Gln Gly Glu Thr
545                 550                 555                 560

Gly Arg Pro Gly Pro Pro Gly Ser Pro Gly Pro Arg Gly Gln Pro Gly
                565                 570                 575

Val Met Gly Phe Pro Gly Pro Lys Gly Asn Asp Gly Ala Pro Gly Lys
            580                 585                 590

Asn Gly Glu Arg Gly Gly Pro Gly Gly Pro Gly Pro Gln Gly Pro Ala
        595                 600                 605

Gly Lys Asn Gly Glu Thr Gly Pro Gln Gly Pro Pro Gly Pro Thr Gly
    610                 615                 620

Pro Ser Gly Asp Lys Gly Asp Thr Gly Pro Pro Gly Pro Gln Gly Leu
625                 630                 635                 640

Gln Gly Leu Pro Gly Thr Ser Gly Pro Pro Gly Glu Asn Gly Lys Pro
                645                 650                 655

Gly Glu Pro Gly Pro Lys Gly Glu Ala Gly Ala Pro Gly Ile Pro Gly
            660                 665                 670

Gly Lys Gly Asp Ser Gly Ala Pro Gly Glu Arg Gly Pro Pro Gly Ala
        675                 680                 685

Gly Gly Pro Pro Gly Pro Arg Gly Gly Ala Gly Pro Pro Gly Pro Glu
    690                 695                 700

Gly Gly Lys Gly Ala Ala Gly Pro Pro Gly Pro Pro Gly Ser Ala Gly
705                 710                 715                 720

Thr Pro Gly Leu Gln Gly Met Pro Gly Glu Arg Gly Gly Pro Gly Gly
                725                 730                 735
```

```
Pro Gly Pro Lys Gly Asp Lys Gly Glu Pro Gly Ser Ser Gly Val Asp
            740                 745                 750

Gly Ala Pro Gly Lys Asp Gly Pro Arg Gly Pro Thr Gly Pro Ile Gly
            755                 760                 765

Pro Pro Gly Pro Ala Gly Gln Pro Gly Asp Lys Gly Glu Ser Gly Ala
            770                 775                 780

Pro Gly Val Pro Gly Ile Ala Gly Pro Arg Gly Gly Pro Gly Glu Arg
785                 790                 795                 800

Gly Glu Gln Gly Pro Pro Gly Pro Ala Gly Phe Pro Gly Ala Pro Gly
                805                 810                 815

Gln Asn Gly Glu Pro Gly Ala Lys Gly Glu Arg Gly Ala Pro Gly Glu
            820                 825                 830

Lys Gly Glu Gly Gly Pro Pro Gly Ala Ala Gly Pro Ala Gly Gly Ser
            835                 840                 845

Gly Pro Ala Gly Pro Pro Gly Pro Gln Gly Val Lys Gly Glu Arg Gly
            850                 855                 860

Ser Pro Gly Gly Pro Gly Ala Ala Gly Phe Pro Gly Gly Arg Gly Pro
865                 870                 875                 880

Pro Gly Pro Pro Gly Ser Asn Gly Asn Pro Gly Pro Pro Gly Ser Ser
                885                 890                 895

Gly Ala Pro Gly Lys Asp Gly Pro Pro Gly Pro Pro Gly Ser Asn Gly
            900                 905                 910

Ala Pro Gly Ser Pro Gly Ile Ser Gly Pro Lys Gly Asp Ser Gly Pro
            915                 920                 925

Pro Gly Glu Arg Gly Ala Pro Gly Pro Gln Gly Pro Pro Gly Ala Pro
            930                 935                 940

Gly Pro Leu Gly Ile Ala Gly Leu Thr Gly Ala Arg Gly Leu Ala Gly
945                 950                 955                 960

Pro Pro Gly Met Pro Gly Ala Arg Gly Ser Pro Gly Pro Gln Gly Ile
                965                 970                 975

Lys Gly Glu Asn Gly Lys Pro Gly Pro Ser Gly Gln Asn Gly Glu Arg
            980                 985                 990

Gly Pro Pro Gly Pro Gln Gly Leu Pro Gly Leu Ala Gly Thr Ala Gly
            995                 1000                1005

Glu Pro Gly Arg Asp Gly Asn Pro Gly Ser Asp Gly Leu Pro Gly
        1010            1015            1020

Arg Asp Gly Ala Pro Gly Ala Lys Gly Asp Arg Gly Glu Asn Gly
        1025            1030            1035

Ser Pro Gly Ala Pro Gly Ala Pro Gly His Pro Gly Pro Pro Gly
        1040            1045            1050

Pro Val Gly Pro Ala Gly Lys Ser Gly Asp Arg Gly Glu Thr Gly
        1055            1060            1065

Pro Ala Gly Pro Ser Gly Ala Pro Gly Pro Ala Gly Ser Arg Gly
        1070            1075            1080

Pro Pro Gly Pro Gln Gly Pro Arg Gly Asp Lys Gly Glu Thr Gly
        1085            1090            1095

Glu Arg Gly Ala Met Gly Ile Lys Gly His Arg Gly Phe Pro Gly
        1100            1105            1110

Asn Pro Gly Ala Pro Gly Ser Pro Gly Pro Ala Gly His Gln Gly
        1115            1120            1125

Ala Val Gly Ser Pro Gly Pro Ala Gly Pro Arg Gly Pro Val Gly
        1130            1135            1140

Pro Ser Gly Pro Pro Gly Lys Asp Gly Ala Ser Gly His Pro Gly
```

Pro Ile Gly Pro Pro Gly Pro Arg Gly Asn Arg Gly Glu Arg Gly
            1160                1165                1170

Ser Glu Gly Ser Pro Gly His Pro Gly Gln Pro Gly Pro Pro Gly
    1175                1180                1185

Pro Pro Gly Ala Pro Gly Pro Cys Cys Gly Ala Gly Gly Val Ala
        1190                1195                1200

Ala Ile Ala Gly Val Gly Ala Glu Lys Ala Gly Gly Phe Ala Pro
    1205                1210                1215

Tyr Tyr Gly Asp Glu Pro Ile Asp Phe Lys Ile Asn Thr Asp Glu
    1220                1225                1230

Ile Met Thr Ser Leu Lys Ser Val Asn Gly Gln Ile Glu Ser Leu
    1235                1240                1245

Ile Ser Pro Asp Gly Ser Arg Lys Asn Pro Ala Arg Asn Cys Arg
    1250                1255                1260

Asp Leu Lys Phe Cys His Pro Glu Leu Gln Ser Gly Glu Tyr Trp
    1265                1270                1275

Val Asp Pro Asn Gln Gly Cys Lys Leu Asp Ala Ile Lys Val Tyr
    1280                1285                1290

Cys Asn Met Glu Thr Gly Glu Thr Cys Ile Ser Ala Ser Pro Leu
    1295                1300                1305

Thr Ile Pro Gln Lys Asn Trp Trp Thr Asp Ser Gly Ala Glu Lys
    1310                1315                1320

Lys His Val Trp Phe Gly Glu Ser Met Glu Gly Gly Phe Gln Phe
    1325                1330                1335

Ser Tyr Gly Asn Pro Glu Leu Pro Glu Asp Val Leu Asp Val Gln
    1340                1345                1350

Leu Ala Phe Leu Arg Leu Leu Ser Ser Arg Ala Ser Gln Asn Ile
    1355                1360                1365

Thr Tyr His Cys Lys Asn Ser Ile Ala Tyr Met Asp His Ala Ser
    1370                1375                1380

Gly Asn Val Lys Lys Ala Leu Lys Leu Met Gly Ser Asn Glu Gly
    1385                1390                1395

Glu Phe Lys Ala Glu Gly Asn Ser Lys Phe Thr Tyr Thr Val Leu
    1400                1405                1410

Glu Asp Gly Cys Thr Lys His Thr Gly Glu Trp Gly Lys Thr Val
    1415                1420                1425

Phe Gln Tyr Gln Thr Arg Lys Ala Val Arg Leu Pro Ile Val Asp
    1430                1435                1440

Ile Ala Pro Tyr Asp Ile Gly Gly Pro Asp Gln Glu Phe Gly Ala
    1445                1450                1455

Asp Ile Gly Pro Val Cys Phe Leu
    1460                1465

<210> SEQ ID NO 14
<211> LENGTH: 403
<212> TYPE: PRT
<213> ORGANISM: Artificial Sequence
<220> FEATURE:
<223> OTHER INFORMATION: Synthetic peptide: bifunctional arginine
      demethylase and lysyl-hydroxylase JMJD6 (Bos taurus), NCBI
      reference sequence: NP_001029492.2

<400> SEQUENCE: 14

Met Asn His Lys Ser Lys Lys Arg Ile Arg Glu Ala Lys Arg Ser Ala
1               5                   10                  15

Arg Pro Glu Leu Lys Asp Ser Leu Asp Trp Thr Arg His Asn Tyr Phe
            20                  25                  30

Glu Ser Phe Pro Leu Asn Pro Ala Val Ala Asp Asn Val Glu Arg
        35                  40                  45

Ala Asp Ala Leu Gln Leu Ser Val Glu Glu Phe Val Glu Arg Tyr Glu
 50                  55                  60

Arg Pro Tyr Lys Pro Val Val Leu Leu Asn Ala Gln Glu Gly Trp Ser
 65                  70                  75                  80

Ala Gln Glu Lys Trp Thr Leu Glu Arg Leu Lys Arg Lys Tyr Arg Asn
                 85                  90                  95

Gln Lys Phe Lys Cys Gly Glu Asp Asn Asp Gly Tyr Ser Val Lys Met
            100                 105                 110

Lys Met Lys Tyr Tyr Ile Glu Tyr Met Glu Ser Thr Arg Asp Asp Ser
        115                 120                 125

Pro Leu Tyr Ile Phe Asp Ser Ser Tyr Gly Glu His Pro Lys Arg Arg
130                 135                 140

Lys Leu Leu Glu Asp Tyr Lys Val Pro Lys Phe Phe Thr Asp Asp Leu
145                 150                 155                 160

Phe Gln Tyr Ala Gly Glu Lys Arg Arg Pro Pro Tyr Arg Trp Phe Val
                165                 170                 175

Met Gly Pro Pro Arg Ser Gly Thr Gly Ile His Ile Asp Pro Leu Gly
            180                 185                 190

Thr Ser Ala Trp Asn Ala Leu Val Gln Gly His Lys Arg Trp Cys Leu
        195                 200                 205

Phe Pro Thr Ser Thr Pro Arg Glu Leu Ile Lys Val Thr Arg Glu Glu
210                 215                 220

Gly Gly Asn Gln Gln Asp Glu Ala Ile Thr Trp Phe Asn Ile Ile Tyr
225                 230                 235                 240

Pro Arg Thr Gln Leu Pro Thr Trp Pro Pro Glu Phe Lys Pro Leu Glu
                245                 250                 255

Ile Leu Gln Lys Pro Gly Glu Thr Val Phe Val Pro Gly Gly Trp Trp
            260                 265                 270

His Val Val Leu Asn Leu Asp Thr Thr Ile Ala Ile Thr Gln Asn Phe
        275                 280                 285

Ala Ser Ser Thr Asn Phe Pro Val Val Trp His Lys Thr Val Arg Gly
290                 295                 300

Arg Pro Lys Leu Ser Arg Lys Trp Tyr Arg Ile Leu Lys Gln Glu His
305                 310                 315                 320

Pro Glu Leu Ala Val Leu Ala Asp Ser Val Asp Leu Gln Glu Ser Thr
                325                 330                 335

Gly Ile Ala Ser Asp Ser Ser Asp Ser Ser Ser Ser Ser Ser Ser Ser
            340                 345                 350

Ser Ser Ser Asp Ser Asp Ser Glu Cys Glu Ser Gly Ser Glu Gly Glu
        355                 360                 365

Gly Thr Met His Arg Arg Lys Lys Arg Arg Thr Cys Gly Met Val Gly
370                 375                 380

Asn Gly Asp Thr Thr Ser Gln Asp Asp Cys Val Ser Lys Glu Arg Ser
385                 390                 395                 400

Ser Ser Arg

<210> SEQ ID NO 15
<211> LENGTH: 1605
<212> TYPE: DNA

<213> ORGANISM: Artificial Sequence
<220> FEATURE:
<223> OTHER INFORMATION: Synthetic nucleotide: bovine P4HA cDNA native

<400> SEQUENCE: 15

```
atgatctggt atattttagt tgtagggatt ctacttcccc agtctttggc ccatccaggc      60
ttttttactt ctattggtca gatgactgat ttgattcata ctgaaaaaga tctggtgact     120
tccctgaaag actatataaa ggcagaagag acaaaattag aacaaataaa aaatgggca      180
gagaaattag atcgattaac cagcacagcg acaaagatc cagaaggatt tgttggacac     240
cctgtaaatg cattcaaatt aatgaaacgt ctgaacactg agtggagtga gttggagaat     300
ctggtcctta aggatatgtc agatggtttt atctctaacc taaccattca gagacagtac     360
ttccctaatg atgaagatca ggttggggca gccaaagctc tgttgcgtct acaggacacc     420
tacaatttgg atacagatac catctcaaag ggtgatcttc aggagtaaaa acacaaatct     480
tttctaacag ttgaggactg ttttgagttg ggcaaagtgg cctacacaga agcagattat     540
taccatacag agctgtggat ggaacaagca ctgaggcagc tggatgaagg cgaggtttct     600
accgttgata aagtctctgt tctggattat ttgagctatg cagtatacca gcaggagac      660
ctggataagg cgcttttgct cacaaagaag cttcttgaac tagatcctga acatcagaga     720
gctaacggta acttaaaata ctttgagtat ataatggcta agaaaaaga tgccaataag      780
tcttcttcag atgaccaatc tgatcagaaa accacactga gaagaaagg tgctgctgtg      840
gattacctgc agagagaca gaagtacgaa atgctgtgcc gtggggaggg tatcaaaatg      900
actcctcgga gacagaaaaa actcttctgt cgctaccatg atggaaaccg gaatcctaaa     960
tttatcctgg ctccagccaa acaggaggat gagtgggaca gcctcgtat tatccgcttc    1020
catgatatta tttctgatgc agaaattgaa gtcgttaaag atctagcaaa accaaggctg    1080
aggcgagcca ccatttcaaa cccaataaca ggagacttgg agacggtaca ttacagaatt    1140
agcaaaagtg cctggctgtc tggctatgaa aaccctgtgg tgtcacgaat taatatgaga    1200
atccaagatc tgacaggact agatgtctcc acagcagagg aattacaggt agcaaattat    1260
ggagttggag acagtatga accccatttt gattttgcac ggaaagatga gccagatgct    1320
ttcaaagagc tggggacagg aaatagaatt gctacatggc tgttttatat gagtgatgtg    1380
ttagcaggag gagccactgt ttttcctgaa gtaggagcta gtgtttggcc caaaaaggga    1440
actgctgttt tctggtataa tctgtttgcc agtggagaag gagattatag tacacggcat    1500
gcagcctgtc cagtgctggt tggaaacaaa tgggtatcca ataaatggct ccatgaacgt    1560
ggacaggaat ttcgaagacc atgcaccttg tcagaattgg aatga                   1605
```

<210> SEQ ID NO 16
<211> LENGTH: 1533
<212> TYPE: DNA
<213> ORGANISM: Artificial Sequence
<220> FEATURE:
<223> OTHER INFORMATION: Synthetic nucleotide: bovine P4HB (PDI)
    sequence, native with own signal peptide

<400> SEQUENCE: 16

```
atgctgcgcc gcgctctgct ctgcctggcc ctgaccgcgc tattccgcgc gggtgccggc      60
gccccgacg aggaggacca cgtcctggtg ctccataagg caacttcga cgaggcgctg      120
gcggcccaca gtaccctgct ggtggagttc tacgccccat ggtgcggcca ctgcaaggct     180
ctggcccgg agtatgccaa agcagctggg aagctgaagg cagaaggttc tgagatcaga     240
```

-continued

```
ctggccaagg tggatgccac tgaagagtct gacctggccc agcagtatgg tgtccgaggc      300
taccccacca tcaagttctt caagaatgga gacacagctt ccccaaaga gtacacagct      360
ggccgagaag cggatgatat cgtgaactgg ctgaagaagc gcacgggccc cgctgccagc      420
acgctgtccg acggggctgc tgcagaggcc ttggtggagt ccagtgaggt ggccgtcatt      480
ggcttcttca aggacatgga gtcggactcc gcaaagcagt tcttgttggc agcagaggcc      540
attgatgaca tccccttcgg gatcacatct aacagcgatg tgttctccaa ataccagctg      600
gacaaggatg gggttgtcct ctttaagaag tttgacgaag gccggaacaa ctttgagggg      660
gaggtcacca agaaaaagct tctggacttc atcaagcaca accagttgcc cctggtcatt      720
gagttcaccg agcagacagc cccgaagatc ttcggagggg aaatcaagac tcacatcctg      780
ctgttcctgc cgaaaagcgt gtctgactat gagggcaagc tgagcaactt caaaaaagcg      840
gctgagagct tcaagggcaa gatcctgttt atcttcatcg acagcgacca cactgacaac      900
cagcgcatcc tggaattctt cggcctaaag aaagaggagt gccggccgt gcgcctcatc      960
acgctggagg aggagatgac caaatataag ccagagtcag atgagctgac ggcagagaag     1020
atcaccgagt tctgccaccg cttcctggag ggcaagatta gccccacct gatgagccag     1080
gagctgcctg acgactggga caagcagcct gtcaaagtgc tggttgggaa gaactttgaa     1140
gaggttgctt ttgatgagaa aaagaacgtc tttgtagagt tctatgcccc gtggtgcggt     1200
cactgcaagc agctggcccc catctgggat aagctgggag acgtacaa ggaccacgag      1260
aacatagtca tcgccaagat ggactccacg gccaacgagg tggaggcggt gaaagtgcac     1320
agcttcccca cgctcaagtt cttccccgcc agcgccgaca ggacggtcat cgactacaat     1380
ggggagcgga cactggatgg ttttaagaag ttcctggaga gtggtggcca ggatggggcc     1440
ggagatgatg acgatctaga agatcttgaa gaagcagaag agcctgatct ggaggaagat     1500
gatgatcaaa aagctgtgaa agatgaactg taa                                  1533
```

<210> SEQ ID NO 17
<211> LENGTH: 1323
<212> TYPE: DNA
<213> ORGANISM: Artificial Sequence
<220> FEATURE:
<223> OTHER INFORMATION: Synthetic nucleotide: L-gulono, 1,4-lactone oxidase

<400> SEQUENCE: 17

```
atggtgcacg gctacaaggg cgtccagttt caaaactggg ctaagacgta tggatgttcc       60
ccagaggttt attaccagcc tacgtcagtc gaagaggtga gagaagtact ggcattggca      120
agggaacaaa agaaaaagt gaaggtcgtg gtggcggac atagtccatc gacattgca      180
tgcactgacg gatttatgat ccatatggga aagatgaata gagtcttgca agtagataaa      240
gaaaaaaagc agattaccgt tgaagctggt atcctgctgg ctgatctgca tccccagctg      300
gatgaacatg tcttgctat gtctaatcta ggcgccgtat ccgacgttac agttgctggt      360
gtgattggta gtggcaccca caacacggga ataaaacacg gaatactagc caccaagta      420
gttgctctta ccttaatgac ggccgatggt gaagtcctgg agtgtagtga gtctagaaac      480
gccgacgtct ttcaagctgc ccgtgtgcat cttggttgct tgggcatcat cctaacagtc      540
acccttcaat gcgtccctca gtttcatcta caagaaactt ccttcccaag taccttaaag      600
gaggtcctag ataatttgga ttcacacctg aagagatcag agtatttcag gttcctgtgg      660
tttccacata cagagaacgt ttccatcatc tatcaagacc atacaaataa agcaccctcc      720
```

| | |
|---|---|
| agtgcttcta actggttttg ggattatgca atcggttttt atctacttga attttttactg | 780 |
| tggacttcta cctacctacc ttgtttggtg ggttggataa accgtttctt tttttggatg | 840 |
| cttttcaatt gcaagaaaga gagttccaac ctatcccaca agatcttcac ttatgaatgc | 900 |
| cgttttaagc aacacgtgca agattgggca atcccaagag aaaagaccaa ggaggctctt | 960 |
| ttggagctaa aagcaatgct tgaggcacac cccaaggtag tggcccacta ccctgtagag | 1020 |
| gtcaggttca ccaggggcga tgatatattg ctgtcacctt gcttccagcg tgattcctgc | 1080 |
| tacatgaaca tcattatgta caggccctac ggcaaagacg tgccaagact agattactgg | 1140 |
| cttgcttacg agacgattat gaagaaattt ggaggtagac cccattgggc caaggctcac | 1200 |
| aactgtactc agaaggattt cgaggaaatg tatccaacct tccataaatt ttgcgacata | 1260 |
| agggaaaaac ttgaccctac aggcatgttc ctaaattctt accttgaaaa ggtctttttat | 1320 |
| taa | 1323 |

<210> SEQ ID NO 18
<211> LENGTH: 1134
<212> TYPE: DNA
<213> ORGANISM: Artificial Sequence
<220> FEATURE:
<223> OTHER INFORMATION: Synthetic nucleotide: GDP-Mannose-3,5-
      epimerase, codon optimized for Pichia

<400> SEQUENCE: 18

| | |
|---|---|
| atgggcacca ccaatggtac agattatggc gcatatactt acaaggaatt ggaaagagag | 60 |
| cagtactggc cctctgagaa tctgaagatt tccataactg gtgcaggcgg atttatagca | 120 |
| tcccatattg caaggagatt aaaacacgag ggacactatg taatagcatc tgactggaaa | 180 |
| aagaacgagc acatgactga ggacatgttt tgcgacgaat tcatcttgt tgacttaagg | 240 |
| gtcatggaaa attgccttaa agttactgag ggcgtagacc acgtctttaa ccttgccgcc | 300 |
| gacatgggcg gtatgggatt catccagtcc aatcattccg tgatcatgta caacaatacg | 360 |
| atgatcagtt tcaacatgat tgaagctgct agaatcaatg gaatcaagag attcttttac | 420 |
| gcatcttcag catgtatcta tccagaattt aagcaacttg aaaccactaa tgttagtctt | 480 |
| aaggaatccg acgcttggcc cgcagaacct caagatgcat atggtttgga gaaactggca | 540 |
| accgaagagc tatgcaaaca ttacaacaag gactttggta tcgagtgcag gattggcaga | 600 |
| ttccacaaca tatacggccc tttcggaact tggaaaggtg gcagagaaaa ggcccctgct | 660 |
| gctttctgta ggaaagcaca aacctccaca gataggtttg agatgtgggg cgatggccta | 720 |
| cagacaaggt cttttacttt cattgacgaa tgtgtcgaag gagttttgcg tttaactaag | 780 |
| agtgatttta gggagcctgt caatataggga tccgatgaga tggtgtccat gaacgagatg | 840 |
| gcagagatgt ttttatcttt tgaggagaaa aagctgccca tccatcatat tcccggtccc | 900 |
| gagggtgtca gaggcagaaa tagtgataat aacctaatca aggaaaaact tggttgggca | 960 |
| ccaaatatga gattgaaaga aggccttaga attacttact tctggataaa agaacaaatt | 1020 |
| gaaaaggaaa aggccaaggg tagtgatgtt agtctatacg gatcatctaa ggtcgttgga | 1080 |
| acgcaggccc cagtccaact gggaagtctt agagcagctg atggaaaaga ataa | 1134 |

<210> SEQ ID NO 19
<211> LENGTH: 1329
<212> TYPE: DNA
<213> ORGANISM: Artificial Sequence
<220> FEATURE:
<223> OTHER INFORMATION: Synthetic nucleotide: GDP-L-galactose
      phosphorylase

<400> SEQUENCE: 19

```
atgctgaaga tcaagagggt ccctactgtg gtgtcaaact accaaaaaga tgacggcgcc    60
gaagatcctg tcggatgtgg tagaaactgt cttggcgcat gttgcctgaa tggagcccgt   120
ctacctttat atgcctgtaa aaatttggta aaatcaggag aaaaattagt cattagtcac   180
gaggctatcg agccacccgt agcttttctt gagtcattgg ttctgggcga gtgggaggat   240
aggtttcaga gaggactgtt ccgttacgac gtcacggcat gcgagacaaa agtgataccc   300
ggaaaatatg gattcgttgc ccaactgaac gaaggcagac atctaaagaa gcgtccaacc   360
gaatttaggg tggataaagt attacaatct tttgatggct caaatttaa ttttactaaa    420
gttggacagg aagaactgct gtttcagttt gaagccggtg aagacgcaca ggtacagttt   480
tttccatgca tgccaataga tccagaaaat tcaccctctg tggtcgcaat aaatgtttcc   540
ccaatagaat atggacacgt tttacttatt cctagggtgt tggactgcct gccacaaagg   600
atcgaccaca agagtctttt gctggctgta catatggcag ctgaagctgc aaatccctac   660
ttccgtcttg gatacaattc tttgggtgcc tttgccacga tcaatcattt gcattttcaa   720
gcctactacc tggcaatgcc attcccatta gagaaagctc ctactaaaaa gattacgacc   780
accgtttcag gagtgaaaat atccgaactg ttaagttatc ccgtaagatc cctgctgttt   840
gaaggaggta gttccatgca agaattaagt gatacagtca gtgactgttg cgtgtgtcta   900
caaaataaca acataccatt taacatacta atctccgact gtggcaggca aatatttta    960
atgcctcaat gttatgccga aaacaggcc ttaggagagg tgtccctga agtgctagaa    1020
actcaggtga acccagccgt ttgggagatt tccggtcaca tggtccttaa aagaaaagaa  1080
gactacgaag gtgcctctga ggacaacgct tggcgtctac tagctgaggc tagtctaagt  1140
gaagaaagat tcaaggaagt tactgctcta gcattcgagg ccatcggctg ttccaatcaa  1200
gaggaagacc ttgaaggcac tatagtccac caacaaaaca gttctggaaa cgtgaaccaa  1260
aaatcaaaca gaacacacgg cggaccaatc accaatggta cggctgcaga gtgtttagtt  1320
ttacaataa                                                          1329
```

<210> SEQ ID NO 20
<211> LENGTH: 816
<212> TYPE: DNA
<213> ORGANISM: Artificial Sequence
<220> FEATURE:
<223> OTHER INFORMATION: Synthetic nucleotide: Inositol-phosphate phosphatase

<400> SEQUENCE: 20

```
atggccgaca atgattctct tgaccagttt ctggccgccg ccatcgacgc cgcaaaaaag    60
gcaggacaga ttattcgtaa gggattttat gaaaccaagc acgtcgagca taaaggtcag   120
gtcgatctag tgactgaaac ggataagggc tgtgaagaac tggtgttcaa tcatttaaaa   180
cagctattcc ccaatcataa gttcattggc gaagagacaa ctgctgcatt tggtgtaacg   240
gagctaactg atgagccaac ctggatcgta gatcccttag atggcaccac taatttcgta   300
catggttttc cttttgtgtg cgtatcaata ggtttaacca tcgtaaagt acctgtcgta    360
ggcgtcgttt acaatcccat tatggaagag cttttttacag gcgtccaagg aaaaggcgct   420
ttcttaaacg gaaaaaggat taagtttct gcccagtcag agctattgac tgctctactt    480
gtcaccgagg caggtacaaa acgtgataaa gctactctgg atgatacaac caatcgtata   540
aactccctat tgactaaagt aaggagtctt cgtatgtcag gtagttgtgc cttagatttg   600
```

```
tgtggcgtag cctgcggaag ggtcgacatc ttctacgagt tgggtttcgg aggaccctgg      660
gacattgccg ccggaatagt gatcgtcaag gaagctggag gactaatctt cgatcctagt      720
ggtaaggatc tggacataac gtcacaaagg atcgcagcca gtaacgcatc cttaaaagag      780
ctatttgcag aagctctgag attgactgga gcctaa                                816

<210> SEQ ID NO 21
<211> LENGTH: 2746
<212> TYPE: DNA
<213> ORGANISM: Artificial Sequence
<220> FEATURE:
<223> OTHER INFORMATION: Synthetic nucleotide: GDP-L-Gal phosphorylase
      from Arabidopsis thaliana

<400> SEQUENCE: 21
ctggttcact catctcctat ctatttaaag cccattcgat atcctaaaac actgtatcat       60 caaaaacac ctcaaagaat tattcattca ggcatcttct caaatttttg tttgtgaaaa       120
aaacccacat caaaagatct ctcatttatt cgtttcgttt ctgctgtttt gagtgtcggg      180
ttcgttttag ctgtaatctt ttttttccggc gttcgatttg aaaaaatccg gggaacaggt     240
gatcggaatc acggctatac acgggatatc acggggtgtt agctcacatg tccatattgt     300
ccgacagaag ggttgtttaa tcgaaactaa tcctttgccg cacggaggac gtggagctct     360
gccgtctgaa ggcggcagcc cttccgatct cctcttctc gccggtggcg gttccagctt      420
taacttcttt tcctttaggt tttaggagtt agggtttgtt agtgtttttt ccttcttctt     480
tttttggtgc tcttgaatcg cttttttctt ggggaagtt ttttcttttg ctcttcgaaa     540
tttgtctttt ttgagaatgt tgaaaatcaa aagagttccg accgttgttt cgaactacca     600
gaaggacgat ggagcggagg atcccgtcgg ctgtggacgg aattgcctcg gcgcttgttg     660
ccttaacggt acgttttgga aacctgaatc gtctttttta atcatgttta aattttatca     720 ctttttttt attcaccta tgatgtgttt gttcagggc taggcttcca ttgtatgcat       780
gtaagaatct ggtaaaatcc ggagagaagc ttgtaatcag tcatgaggct atagagcctc     840
ctgtagcttt tctcgagtcc cttgttctcg gagaggtaaa tcatagacca ctgatttga     900 tattctgata atggtttctg tagcttggaa gagtctaatc agtattctta tgtttagtgg     960
gaggataggt tccaaagagg acttttcgc tatgatgtca ctgcctgcga accaaagta     1020 attgtctttc ttaccttgtt tgacaatcta gttatgttgg gttgtttgtt gctgaggaat    1080
ccgagatatg ttttacattg ttcttaagat tgtttctctt gatgttatag ttatcccgg    1140 ggaagtatgg tttcgttgct cagcttaacg agggtcgtca cttgaagaag aggccaactg    1200
agttccgtgt agataaggtg ttgcagtctt ttgatggcag caaattcaac ttcactaaag    1260
ttggccaaga agagttgctc ttccagtttg aagctggtga agatgcccaa gttcagttct    1320
tcccttgcat gcctattgac cctgagaatt ctcccagtgt tgttgccatc aatgtaaaga    1380
ctcttgtgca gagagcttgg tttttctctt cttcctttta ttggtttcgc tagcaaaaga    1440
ttaattcttt attgttgttt ttaacaggtt agtccgatag agtatggcca tgtgctgctg    1500
attcctcgtg tcttgactg cttgcctcaa aggatcgatc acaaaagcct tttgcttgca    1560
gttcacatgg ctgctgaggc tgctaatcca tacttcagac tcggttacaa cagcttgggt    1620
gcttttgcca ctatcaatca tctccactt caggtatatc caaaagtgat ccaagcataa    1680
ccttttcacc cttgctcatc taagatgttt gttctgattg ttttggtggt gattgttttt    1740
ggaaacaggc ttattacttg gccatgcctt tcccactgga gaaagctcct accaagaaga   1800
```

-continued

```
taactaccac tgttagtggt gtcaaaatct cagagcttct aagttaccct gtgagaagtc    1860
ttctctttga aggtggaagc tctatgcaag aactatctga tactgtttca gactgctgtg    1920
tttgccttca aaacaacaac attcctttca acattctcat ctctgattgt ggaaggcaga    1980
tcttcttaat gccacaggta tataactaca ccgttggatg aatacatgtt ttgaattact    2040
taatcaaaag tgaataacag tttgaatgta aaaattgcag tgttacgcag agaaacaggc    2100
tctaggtgaa gtgagcccgg aggtattgga acacaagtg  aacccagccg tgtgggagat    2160
aagtggtcac atggtactga agaggaaaga ggattacgaa ggtgcttcag aggataacgc    2220
gtggaggctc cttgcggaag cttctctgtc ggaggaaagg tttaaggagg ttactgctct    2280
cgcctttgaa gccataggtt gtagtaacca agaggaggat cttgaaggaa ccatagttca    2340
tcagcaaaac tctagtggca atgttaacca gaaaagcaac agaacccatg gaggtccgat    2400
cacaaatggg acggccgccg agtgccttgt ccttcagtga acaatatggt gacttggtgg    2460
tttgtatgta taattaaaag cctaaataag caaactctct ttgtagttgc atttgaagct    2520
tcttggttta tgtatgatgg ttgtgggcat tttgtgccta gacttctggt tcttttgtttt    2580 ttgttatgag ttggtgttta tgaattatat atgttcttca ctaatatgat tattatttgt    2640
atagatttga ttattcaaag gatatgtctt aagaagggt tcaggttcag ccaactaatt    2700
acttgtaacc aagtctttct accatcaaca accatgttaa gattca                   2746
```

<210> SEQ ID NO 22
<211> LENGTH: 442
<212> TYPE: PRT
<213> ORGANISM: Artificial Sequence
<220> FEATURE:
<223> OTHER INFORMATION: Synthetic peptide: GDP-L-Gal phosphorylase from
      Arabidopsis thaliana

<400> SEQUENCE: 22

```
Met Leu Lys Ile Lys Arg Val Pro Thr Val Val Ser Asn Tyr Gln Lys
1               5                   10                  15

Asp Asp Gly Ala Glu Asp Pro Val Gly Cys Gly Arg Asn Cys Leu Gly
                20                  25                  30

Ala Cys Cys Leu Asn Gly Ala Arg Leu Pro Leu Tyr Ala Cys Lys Asn
            35                  40                  45

Leu Val Lys Ser Gly Glu Lys Leu Val Ile Ser His Glu Ala Ile Glu
        50                  55                  60

Pro Pro Val Ala Phe Leu Glu Ser Leu Val Leu Gly Glu Trp Glu Asp
    65                  70                  75                  80

Arg Phe Gln Arg Gly Leu Phe Arg Tyr Asp Val Thr Ala Cys Glu Thr
                85                  90                  95

Lys Val Ile Pro Gly Lys Tyr Gly Phe Val Ala Gln Leu Asn Glu Gly
                100                 105                 110

Arg His Leu Lys Lys Arg Pro Thr Glu Phe Arg Val Asp Lys Val Leu
            115                 120                 125

Gln Ser Phe Asp Gly Ser Lys Phe Asn Phe Thr Lys Val Gly Gln Glu
        130                 135                 140

Glu Leu Leu Phe Gln Phe Glu Ala Gly Glu Asp Ala Gln Val Gln Phe
    145                 150                 155                 160

Phe Pro Cys Met Pro Ile Asp Pro Glu Asn Ser Pro Ser Val Val Ala
                165                 170                 175

Ile Asn Val Ser Pro Ile Glu Tyr Gly His Val Leu Leu Ile Pro Arg
            180                 185                 190
```

Val Leu Asp Cys Leu Pro Gln Arg Ile Asp His Lys Ser Leu Leu Leu
            195                 200                 205

Ala Val His Met Ala Ala Glu Ala Ala Asn Pro Tyr Phe Arg Leu Gly
        210                 215                 220

Tyr Asn Ser Leu Gly Ala Phe Ala Thr Ile Asn His Leu His Phe Gln
225                 230                 235                 240

Ala Tyr Tyr Leu Ala Met Pro Phe Pro Leu Glu Lys Ala Pro Thr Lys
                245                 250                 255

Lys Ile Thr Thr Thr Val Ser Gly Val Lys Ile Ser Glu Leu Leu Ser
                260                 265                 270

Tyr Pro Val Arg Ser Leu Leu Phe Glu Gly Ser Ser Met Gln Glu
            275                 280                 285

Leu Ser Asp Thr Val Ser Asp Cys Cys Val Cys Leu Gln Asn Asn Asn
        290                 295                 300

Ile Pro Phe Asn Ile Leu Ile Ser Asp Cys Gly Arg Gln Ile Phe Leu
305                 310                 315                 320

Met Pro Gln Cys Tyr Ala Glu Lys Gln Ala Leu Gly Glu Val Ser Pro
                325                 330                 335

Glu Val Leu Glu Thr Gln Val Asn Pro Ala Val Trp Glu Ile Ser Gly
            340                 345                 350

His Met Val Leu Lys Arg Lys Glu Asp Tyr Glu Gly Ala Ser Glu Asp
        355                 360                 365

Asn Ala Trp Arg Leu Leu Ala Glu Ala Ser Leu Ser Glu Glu Arg Phe
    370                 375                 380

Lys Glu Val Thr Ala Leu Ala Phe Glu Ala Ile Gly Cys Ser Asn Gln
385                 390                 395                 400

Glu Glu Asp Leu Glu Gly Thr Ile Val His Gln Gln Asn Ser Ser Gly
                405                 410                 415

Asn Val Asn Gln Lys Ser Asn Arg Thr His Gly Gly Pro Ile Thr Asn
            420                 425                 430

Gly Thr Ala Ala Glu Cys Leu Val Leu Gln
        435                 440

<210> SEQ ID NO 23
<211> LENGTH: 1000
<212> TYPE: DNA
<213> ORGANISM: Artificial Sequence
<220> FEATURE:
<223> OTHER INFORMATION: Synthetic nucleotide: Inositol-phosphate
      phosphatase

<400> SEQUENCE: 23
gcctaaccac aaaaaccgta acttttggtt ttctctgaaa cacatcccaa agtaaagaaa      60
gcatcactct tttcgtcttc tctcgaaaat ggcggacaat gattctctag atcagttttt     120
ggctgccgcc attgatgccg ctaaaaaagc tggacagatc attcgtaaag gttttacga     180 gactaaacat gttgaacaca aaggccaggt ggatttggtg acagagactg ataaaggatg     240
tgaagaactt gtgtttaatc atctcaagca gctctttccc aatcacaagt tcataggaga     300
agaaactaca gctgcatttg gtgtgacaga actaactgac gaaccaactt ggattgttga     360
tcctcttgat ggaacaacca atttcgttca cgggttccct ttcgtgtgtg tttccattgg     420
acttacgatt ggaaaagtcc ctgttgttgg agttgtttat aatcctatta tggaagagct     480
attcaccggt gtccaaggga aaggagcatt cttgaatgaa agcgaatcaa agtgtcagc     540 tcaaagcgaa cttttaaccg ctttgctcgt gacagaggcg ggtactaaac gagataaagc     600

```
tacattagac gatacaacca acagaatcaa cagtttgcta accaaggtca ggtcccttag      660
gatgagtggt tcgtgtgcac tggacctctg tggcgttgcg tgtggaaggg ttgatatctt      720
ctacgagctc ggtttcggtg gtccatggga cattgcagca ggaattgtta tcgtgaaaga      780
agctggtgga ctcatctttg atccatccgg taaagatttg gacataacat cgcagaggat      840
cgcggcttca aacgcttctc tcaaggagtt attcgctgag gcgttgcggc ttacaggggc      900
atgaagtcat ctgttattat tttacaatat ggtctcaacc ttatatgatc aaactcaatt      960
caaaaactta acattattga atatttcttt tcggtagaaa                           1000
```

<210> SEQ ID NO 24
<211> LENGTH: 271
<212> TYPE: PRT
<213> ORGANISM: Artificial Sequence
<220> FEATURE:
<223> OTHER INFORMATION: Synthetic peptide: Inositol-phosphate
     phosphatase

<400> SEQUENCE: 24

```
Met Ala Asp Asn Asp Ser Leu Asp Gln Phe Leu Ala Ala Ala Ile Asp
1               5                   10                  15

Ala Ala Lys Lys Ala Gly Gln Ile Ile Arg Lys Gly Phe Tyr Glu Thr
            20                  25                  30

Lys His Val Glu His Lys Gly Gln Val Asp Leu Val Thr Glu Thr Asp
        35                  40                  45

Lys Gly Cys Glu Glu Leu Val Phe Asn His Leu Lys Gln Leu Phe Pro
    50                  55                  60

Asn His Lys Phe Ile Gly Glu Glu Thr Thr Ala Ala Phe Gly Val Thr
65                  70                  75                  80

Glu Leu Thr Asp Glu Pro Thr Trp Ile Val Asp Pro Leu Asp Gly Thr
                85                  90                  95

Thr Asn Phe Val His Gly Phe Pro Phe Val Cys Val Ser Ile Gly Leu
            100                 105                 110

Thr Ile Gly Lys Val Pro Val Val Gly Val Val Tyr Asn Pro Ile Met
        115                 120                 125

Glu Glu Leu Phe Thr Gly Val Gln Gly Lys Gly Ala Phe Leu Asn Gly
    130                 135                 140

Lys Arg Ile Lys Val Ser Ala Gln Ser Glu Leu Leu Thr Ala Leu Leu
145                 150                 155                 160

Val Thr Glu Ala Gly Thr Lys Arg Asp Lys Ala Thr Leu Asp Asp Thr
                165                 170                 175

Thr Asn Arg Ile Asn Ser Leu Leu Thr Lys Val Arg Ser Leu Arg Met
            180                 185                 190

Ser Gly Ser Cys Ala Leu Asp Leu Cys Gly Val Ala Cys Gly Arg Val
        195                 200                 205

Asp Ile Phe Tyr Glu Leu Gly Phe Gly Gly Pro Trp Asp Ile Ala Ala
    210                 215                 220

Gly Ile Val Ile Val Lys Glu Ala Gly Gly Leu Ile Phe Asp Pro Ser
225                 230                 235                 240

Gly Lys Asp Leu Asp Ile Thr Ser Gln Arg Ile Ala Ala Ser Asn Ala
                245                 250                 255

Ser Leu Lys Glu Leu Phe Ala Glu Ala Leu Arg Leu Thr Gly Ala
            260                 265                 270
```

<210> SEQ ID NO 25

```
<211> LENGTH: 377
<212> TYPE: PRT
<213> ORGANISM: Artificial Sequence
<220> FEATURE:
<223> OTHER INFORMATION: Synthetic peptide: GDP-Mannose-3,5-epimerase

<400> SEQUENCE: 25

Met Gly Thr Thr Asn Gly Thr Asp Tyr Gly Ala Tyr Thr Tyr Lys Glu
 1               5                  10                  15

Leu Glu Arg Glu Gln Tyr Trp Pro Ser Glu Asn Leu Lys Ile Ser Ile
             20                  25                  30

Thr Gly Ala Gly Gly Phe Ile Ala Ser His Ile Ala Arg Arg Leu Lys
         35                  40                  45

His Glu Gly His Tyr Val Ile Ala Ser Asp Trp Lys Lys Asn Glu His
     50                  55                  60

Met Thr Glu Asp Met Phe Cys Asp Glu Phe His Leu Val Asp Leu Arg
 65                  70                  75                  80

Val Met Glu Asn Cys Leu Lys Val Thr Glu Gly Val Asp His Val Phe
                 85                  90                  95

Asn Leu Ala Ala Asp Met Gly Gly Met Gly Phe Ile Gln Ser Asn His
            100                 105                 110

Ser Val Ile Met Tyr Asn Asn Thr Met Ile Ser Phe Asn Met Ile Glu
        115                 120                 125

Ala Ala Arg Ile Asn Gly Ile Lys Arg Phe Phe Tyr Ala Ser Ser Ala
    130                 135                 140

Cys Ile Tyr Pro Glu Phe Lys Gln Leu Glu Thr Thr Asn Val Ser Leu
145                 150                 155                 160

Lys Glu Ser Asp Ala Trp Pro Ala Glu Pro Gln Asp Ala Tyr Gly Leu
                165                 170                 175

Glu Lys Leu Ala Thr Glu Glu Leu Cys Lys His Tyr Asn Lys Asp Phe
            180                 185                 190

Gly Ile Glu Cys Arg Ile Gly Arg Phe His Asn Ile Tyr Gly Pro Phe
        195                 200                 205

Gly Thr Trp Lys Gly Gly Arg Glu Lys Ala Pro Ala Ala Phe Cys Arg
    210                 215                 220

Lys Ala Gln Thr Ser Thr Asp Arg Phe Glu Met Trp Gly Asp Gly Leu
225                 230                 235                 240

Gln Thr Arg Ser Phe Thr Phe Ile Asp Glu Cys Val Glu Gly Val Leu
                245                 250                 255

Arg Leu Thr Lys Ser Asp Phe Arg Glu Pro Val Asn Ile Gly Ser Asp
            260                 265                 270

Glu Met Val Ser Met Asn Glu Met Ala Glu Met Val Leu Ser Phe Glu
        275                 280                 285

Glu Lys Lys Leu Pro Ile His His Ile Pro Gly Pro Glu Gly Val Arg
    290                 295                 300

Gly Arg Asn Ser Asp Asn Asn Leu Ile Lys Glu Lys Leu Gly Trp Ala
305                 310                 315                 320

Pro Asn Met Arg Leu Lys Glu Gly Leu Arg Ile Thr Tyr Phe Trp Ile
                325                 330                 335

Lys Glu Gln Ile Glu Lys Glu Lys Ala Lys Gly Ser Val Ser Leu
            340                 345                 350

Tyr Gly Ser Ser Lys Val Val Gly Thr Gln Ala Pro Val Gln Leu Gly
        355                 360                 365

Ser Leu Arg Ala Ala Asp Gly Lys Glu
    370                 375
```

<210> SEQ ID NO 26
<211> LENGTH: 610
<212> TYPE: PRT
<213> ORGANISM: Artificial Sequence
<220> FEATURE:
<223> OTHER INFORMATION: Synthetic peptide: L-gulono-1,4-lactone oxidase

<400> SEQUENCE: 26

```
Met Leu Arg Ser Leu Leu Arg Arg Ser Val Gly His Ser Leu Gly
1               5                   10                  15

Thr Leu Ser Pro Ser Ser Thr Ile Arg Ser Phe Ser Pro His
            20                  25                  30

Arg Thr Leu Cys Thr Thr Gly Gln Thr Leu Thr Pro Pro Pro Pro
            35                  40                  45

Pro Pro Arg Pro Pro Pro Pro Ala Thr Ala Ser Glu Ala Gln
    50                  55                  60

Phe Arg Lys Tyr Ala Gly Tyr Ala Ala Leu Ala Ile Phe Ser Gly Val
65                  70                  75                  80

Ala Thr Tyr Phe Ser Phe Pro Phe Pro Glu Asn Ala Lys His Lys Lys
                85                  90                  95

Ala Gln Ile Phe Arg Tyr Ala Pro Leu Pro Glu Asp Leu His Thr Val
                100                 105                 110

Ser Asn Trp Ser Gly Thr His Glu Val Gln Thr Arg Asn Phe Asn Gln
                115                 120                 125

Pro Glu Asn Leu Ala Asp Leu Glu Ala Leu Val Lys Glu Ser His Glu
    130                 135                 140

Lys Lys Leu Arg Ile Arg Pro Val Gly Ser Gly Leu Ser Pro Asn Gly
145                 150                 155                 160

Ile Gly Leu Ser Arg Ser Gly Met Val Asn Leu Ala Leu Met Asp Lys
                165                 170                 175

Val Leu Glu Val Asp Lys Glu Lys Lys Arg Val Thr Val Gln Ala Gly
                180                 185                 190

Ile Arg Val Gln Gln Leu Val Asp Ala Ile Lys Asp Tyr Gly Leu Thr
                195                 200                 205

Leu Gln Asn Phe Ala Ser Ile Arg Glu Gln Gln Ile Gly Gly Ile Ile
    210                 215                 220

Gln Val Gly Ala His Gly Thr Gly Ala Arg Leu Pro Pro Ile Asp Glu
225                 230                 235                 240

Gln Val Ile Ser Met Lys Leu Val Thr Pro Ala Lys Gly Thr Ile Glu
                245                 250                 255

Leu Ser Arg Glu Lys Asp Pro Glu Leu Phe His Leu Ala Arg Cys Gly
                260                 265                 270

Leu Gly Gly Leu Gly Val Val Ala Glu Val Thr Leu Gln Cys Val Ala
                275                 280                 285

Arg His Glu Leu Val Glu His Thr Tyr Val Ser Asn Leu Gln Glu Ile
    290                 295                 300

Lys Lys Asn His Lys Lys Leu Leu Ser Ala Asn Lys His Val Lys Tyr
305                 310                 315                 320

Leu Tyr Ile Pro Tyr Thr Asp Thr Val Val Val Thr Cys Asn Pro
                325                 330                 335

Val Ser Lys Trp Ser Gly Pro Pro Lys Asp Lys Pro Lys Tyr Thr Thr
                340                 345                 350

Asp Glu Ala Val Gln His Val Arg Asp Leu Tyr Arg Glu Ser Ile Val
                355                 360                 365
```

```
Lys Tyr Arg Val Gln Asp Ser Gly Lys Lys Ser Pro Asp Ser Ser Glu
        370                 375                 380

Pro Asp Ile Gln Glu Leu Ser Phe Thr Glu Leu Arg Asp Lys Leu Leu
385                 390                 395                 400

Ala Leu Asp Pro Leu Asn Asp Val His Val Ala Lys Val Asn Gln Ala
                405                 410                 415

Glu Ala Glu Phe Trp Lys Lys Ser Gly Tyr Arg Val Gly Trp Ser
            420                 425                 430

Asp Glu Ile Leu Gly Phe Asp Cys Gly Gln Gln Trp Val Ser Glu
            435                 440                 445

Ser Cys Phe Pro Ala Gly Thr Leu Ala Asn Pro Ser Met Lys Asp Leu
        450                 455                 460

Glu Tyr Ile Glu Glu Leu Lys Lys Leu Ile Glu Lys Glu Ala Ile Pro
465                 470                 475                 480

Ala Pro Ala Pro Ile Glu Gln Arg Trp Thr Ala Arg Ser Lys Ser Pro
                485                 490                 495

Ile Ser Pro Ala Phe Ser Thr Ser Glu Asp Asp Ile Phe Ser Trp Val
            500                 505                 510

Gly Ile Ile Met Tyr Leu Pro Thr Ala Asp Pro Arg Gln Arg Lys Asp
            515                 520                 525

Ile Thr Asp Glu Phe Phe His Tyr Arg His Leu Thr Gln Lys Gln Leu
        530                 535                 540

Trp Asp Gln Phe Ser Ala Tyr Glu His Trp Ala Lys Ile Glu Ile Pro
545                 550                 555                 560

Lys Asp Lys Glu Glu Leu Glu Ala Leu Gln Ala Arg Ile Arg Lys Arg
                565                 570                 575

Phe Pro Val Asp Ala Tyr Asn Lys Ala Arg Arg Glu Leu Asp Pro Asn
            580                 585                 590

Arg Ile Leu Ser Asn Asn Met Val Gly Lys Leu Phe Pro Val Ser Thr
            595                 600                 605

Thr Ala
    610

<210> SEQ ID NO 27
<211> LENGTH: 19
<212> TYPE: PRT
<213> ORGANISM: Artificial Sequence
<220> FEATURE:
<223> OTHER INFORMATION: Synthetic peptide

<400> SEQUENCE: 27

Lys Ser Pro Ile Ser Pro Ala Phe Ser Thr Ser Glu Asp Asp Ile Phe
1               5                   10                  15

Ser Trp Val

<210> SEQ ID NO 28
<211> LENGTH: 19
<212> TYPE: PRT
<213> ORGANISM: Artificial Sequence
<220> FEATURE:
<223> OTHER INFORMATION: Synthetic peptide

<400> SEQUENCE: 28

Trp Tyr Asn His Val Pro Pro Asp Ser Arg Pro Ser Pro Glu Lys Gly
1               5                   10                  15

His His Arg
```

```
<210> SEQ ID NO 29
<211> LENGTH: 362
<212> TYPE: PRT
<213> ORGANISM: Artificial Sequence
<220> FEATURE:
<223> OTHER INFORMATION: Synthetic peptide: D-glucuronokinase

<400> SEQUENCE: 29

Met Asp Pro Asn Ser Thr Val Ser Gly Asp Gly Gln Ala Thr Ala Ala
1               5                   10                  15

Ile Glu His Arg Ser Phe Ala Arg Ile Gly Phe Leu Gly Asn Pro Ser
            20                  25                  30

Asp Val Tyr Phe Gly Arg Thr Ile Ser Leu Thr Ile Gly Asn Phe Trp
        35                  40                  45

Ala Ser Val Lys Leu Glu Pro Ser Glu His Leu Val Ile Lys Pro His
    50                  55                  60

Pro Phe His Asp Leu Val Gln Phe Thr Ser Leu Asp His Leu Leu Asn
65                  70                  75                  80

Arg Leu Gln Asn Glu Gly Tyr Tyr Gly Gly Val Arg Leu Leu Met Ala
                85                  90                  95

Ile Cys Lys Val Phe Arg Asn Tyr Cys Lys Glu Asn Asp Ile Gln Leu
            100                 105                 110

His Gln Ala Asn Phe Ser Leu Ser Tyr Asp Thr Asn Ile Pro Arg Gln
        115                 120                 125

Thr Gly Leu Ser Gly Ser Ser Ala Ile Val Ser Ala Ala Leu Asn Cys
    130                 135                 140

Leu Leu Asp Phe Tyr Asn Val Arg His Leu Ile Lys Val Gln Val Arg
145                 150                 155                 160

Pro Asn Ile Val Leu Ser Ala Glu Lys Glu Leu Gly Ile Val Ala Gly
                165                 170                 175

Leu Gln Asp Arg Val Ala Gln Val Tyr Gly Gly Leu Val His Met Asp
            180                 185                 190

Phe Ser Lys Glu His Met Asp Lys Leu Gly His Gly Ile Tyr Thr Pro
        195                 200                 205

Met Asp Ile Ser Leu Leu Pro Pro Leu His Leu Ile Tyr Ala Glu Asn
    210                 215                 220

Pro Ser Asp Ser Gly Lys Val His Ser Met Val Arg Gln Arg Trp Leu
225                 230                 235                 240

Asp Gly Asp Glu Phe Ile Ile Ser Ser Met Lys Glu Val Gly Ser Leu
                245                 250                 255

Ala Glu Glu Gly Arg Thr Ala Leu Leu Asn Lys Asp His Ser Lys Leu
            260                 265                 270

Val Glu Leu Met Asn Leu Asn Phe Asp Ile Arg Arg Arg Met Phe Gly
        275                 280                 285

Asp Glu Cys Leu Gly Ala Met Asn Ile Glu Met Val Glu Val Ala Arg
    290                 295                 300

Arg Val Gly Ala Ala Ser Lys Phe Thr Gly Ser Gly Gly Ala Val Val
305                 310                 315                 320

Val Phe Cys Pro Glu Gly Pro Ser Gln Val Lys Leu Leu Glu Glu Glu
                325                 330                 335

Cys Arg Lys Ala Gly Phe Thr Leu Gln Pro Val Lys Ile Ala Pro Ser
            340                 345                 350

Cys Leu Asn Asp Ser Asp Ile Gln Thr Leu
        355                 360
```

<210> SEQ ID NO 30
<211> LENGTH: 480
<212> TYPE: PRT
<213> ORGANISM: Artificial Sequence
<220> FEATURE:
<223> OTHER INFORMATION: Synthetic peptide: UDP-D-glucose dehydrogenase

<400> SEQUENCE: 30

```
Met Val Lys Ile Cys Cys Ile Gly Ala Gly Tyr Val Gly Gly Pro Thr
1               5                   10                  15

Met Ala Val Ile Ala Leu Lys Cys Pro Asp Ile Glu Val Ala Val Val
                20                  25                  30

Asp Ile Ser Val Pro Arg Ile Asn Ala Trp Asn Ser Asp Gln Leu Pro
            35                  40                  45

Ile Tyr Glu Pro Gly Leu Asp Asp Ile Val Lys Gln Cys Arg Gly Lys
        50                  55                  60

Asn Leu Phe Phe Ser Thr Asp Val Glu Lys His Val Arg Glu Ala Asp
65                  70                  75                  80

Ile Val Phe Val Ser Val Asn Thr Pro Thr Lys Thr Thr Gly Leu Gly
                85                  90                  95

Ala Gly Lys Ala Ala Asp Leu Thr Tyr Trp Glu Ser Ala Ala Arg Met
            100                 105                 110

Ile Ala Asp Val Ser Val Ser Asp Lys Ile Val Val Glu Lys Ser Thr
        115                 120                 125

Val Pro Val Lys Thr Ala Glu Ala Ile Glu Lys Ile Leu Met His Asn
130                 135                 140

Ser Lys Gly Ile Lys Phe Gln Ile Leu Ser Asn Pro Glu Phe Leu Ala
145                 150                 155                 160

Glu Gly Thr Ala Ile Ala Asp Leu Phe Asn Pro Asp Arg Val Leu Ile
                165                 170                 175

Gly Gly Arg Glu Thr Pro Glu Gly Phe Lys Ala Val Gln Thr Leu Lys
            180                 185                 190

Glu Val Tyr Ala Asn Trp Val Pro Glu Gly Gln Ile Ile Thr Thr Asn
        195                 200                 205

Leu Trp Ser Ala Glu Leu Ser Lys Leu Ala Ala Asn Ala Phe Leu Ala
    210                 215                 220

Gln Arg Ile Ser Ser Val Asn Ala Met Ser Ala Leu Cys Glu Ser Thr
225                 230                 235                 240

Gly Ala Asp Val Thr Gln Val Ser Tyr Ala Val Gly Thr Asp Ser Arg
                245                 250                 255

Ile Gly Ser Lys Phe Leu Asn Ala Ser Val Gly Phe Gly Gly Ser Cys
            260                 265                 270

Phe Gln Lys Asp Ile Leu Asn Leu Val Tyr Ile Cys Gln Cys Asn Gly
        275                 280                 285

Leu Pro Glu Val Ala Glu Tyr Trp Lys Gln Val Ile Lys Ile Asn Asp
    290                 295                 300

Tyr Gln Lys Asn Arg Phe Val Asn Arg Ile Val Ser Ser Met Phe Asn
305                 310                 315                 320

Thr Val Ser Asn Lys Lys Val Ala Ile Leu Gly Phe Ala Phe Lys Lys
                325                 330                 335

Asp Thr Gly Asp Thr Arg Glu Thr Pro Ala Ile Asp Val Cys Lys Gly
            340                 345                 350

Leu Leu Gly Asp Lys Ala Gln Ile Ser Ile Tyr Asp Pro Gln Val Thr
        355                 360                 365
```

-continued

```
Glu Glu Gln Ile Gln Arg Asp Leu Ser Met Lys Lys Phe Asp Trp Asp
    370                 375             380

His Pro Leu His Leu Gln Pro Met Ser Pro Thr Thr Val Lys Gln Val
385                 390                 395                 400

Ser Val Thr Trp Asp Ala Tyr Glu Ala Thr Lys Asp Ala His Ala Val
                405                 410                 415

Cys Val Leu Thr Glu Trp Asp Glu Phe Lys Ser Leu Asp Tyr Gln Lys
                420                 425                 430

Ile Phe Asp Asn Met Gln Lys Pro Ala Phe Ile Phe Asp Gly Arg Asn
            435                 440                 445

Ile Met Asn Val Asn Lys Leu Arg Glu Ile Gly Phe Ile Val Tyr Ser
    450                 455                 460

Ile Gly Lys Pro Leu Asp Pro Trp Leu Lys Asp Met Pro Ala Phe Val
465                 470                 475                 480
```